(12) United States Patent
Baron et al.

(10) Patent No.: US 10,323,083 B2
(45) Date of Patent: Jun. 18, 2019

(54) AGENTS THAT SPECIFICALLY BIND MATRILIN-3 AND THEIR USE

(71) Applicant: The United States of America, as represented by the Secretary, Department of Health and Human Services, Washington, DC (US)

(72) Inventors: Jeffrey Baron, Bethesda, MD (US); Crystal Sao Fong Cheung, Bethesda, MD (US); Julian Chun Kin Lui, Bethesda, MD (US); Dimiter Dimitrov, Frederick, MD (US); Zhongyu Zhu, Frederick, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 124 days.

(21) Appl. No.: 15/111,773

(22) PCT Filed: Jan. 14, 2015

(86) PCT No.: PCT/US2015/011433
§ 371 (c)(1),
(2) Date: Jul. 14, 2016

(87) PCT Pub. No.: WO2015/108998
PCT Pub. Date: Jul. 23, 2015

(65) Prior Publication Data
US 2016/0340418 A1  Nov. 24, 2016

Related U.S. Application Data

(60) Provisional application No. 61/927,904, filed on Jan. 15, 2014.

(51) Int. Cl.
| | | |
|---|---|---|
| *A61K 39/395* | (2006.01) | |
| *C07K 16/18* | (2006.01) | |
| *A61K 47/68* | (2017.01) | |
| *A61K 39/00* | (2006.01) | |
| *C07K 14/78* | (2006.01) | |

(52) U.S. Cl.
CPC .......... *C07K 16/18* (2013.01); *A61K 47/6811* (2017.08); *A61K 47/6843* (2017.08); *A61K 2039/505* (2013.01); *C07K 14/78* (2013.01)

(58) Field of Classification Search
None
See application file for complete search history.

(56) References Cited

U.S. PATENT DOCUMENTS

| | | | | |
|---|---|---|---|---|
| 2009/0169562 A1* | 7/2009 | Throsby | ............. | C07K 16/1267 424/142.1 |
| 2013/0323249 A1* | 12/2013 | Zhou | .................. | C07K 16/2818 424/135.1 |

FOREIGN PATENT DOCUMENTS

WO  WO 2004/089990  10/2004

OTHER PUBLICATIONS

Agoston, et al. "C-type natriuretic peptide regulates endochondral bone growth through p38 MAP kinase-dependent and-independent pathways." *BMC Developmental Biology* 7, No. 1 (2007): 1.
Akiyama, et al. "Interactions between Sox9 and β-catenin control chondrocyte differentiation." *Genes & Development* 18, No. 9 (2004): 1072-1087.
Amizuka, et al. "Parathyroid hormone-related peptide-depleted mice show abnormal epiphyseal cartilage development and altered endochondral bone formation." *The Journal of Cell Biology* 126, No. 6 (1994): 1611-1623.
Andrade, et al. "Wnt gene expression in the post-natal growth plate: regulation with chondrocyte differentiation." *Bone* 40, No. 5 (2007): 1361-1369.
Chau, et al. "Organization of the Indian hedgehog—parathyroid hormone-related protein system in the postnatal growth plate." *Journal of Molecular Endocrinology* 47, No. 1 (2011): 99-107.
Cheung, et al. "Identification of chondrocyte-binding peptides by phage display." *Journal of Orthopaedic Research* 31, No. 7 (2013): 1053-1058.
De Luca, et al. "Regulation of Growth Plate Chondrogenesis by Bone Morphogenetic Protein-2 1." *Endocrinology* 142, No. 1 (2001): 430-436.
Hartmann, et al. "Dual roles of Wnt signaling during chondrogenesis in the chicken limb." *Development* 127, No. 14 (2000): 3141-3159.
Hughes, et al. "Human single-chain variable fragment that specifically targets arthritic cartilage." *Arthritis & Rheumatism* 62, No. 4 (2010): 1007-1016.
Igaki, et al. "Effects of intravenously administered C-type natriuretic peptide in humans: comparison with atrial natriuretic peptide." *Hypertension Research* 21, No. 1 (1998): 7-13.
Klatt, et al. "Matrilin-3 activates the expression of osteoarthritis-associated genes in primary human chondrocytes." *FEBS letters* 583, No. 22 (2009): 3611-3617.
Klatt, et al. "Molecular structure and tissue distribution of matrilin-3, a filament-forming extracellular matrix protein expressed during skeletal development." *Journal of Biological Chemistry* 275, No. 6 (2000): 3999-4006.
Klatt, et al. "The matrilins: modulators of extracellular matrix assembly." *The International Journal of Biochemistry & Cell Biology* 43, No. 3 (2011): 320-330.
Kobayashi, et al. "BMP signaling stimulates cellular differentiation at multiple steps during cartilage development." *Proceedings of the National Academy of Sciences of the United States of America* 102, No. 50 (2005): 18023-18027.

(Continued)

*Primary Examiner* — Christine J Saoud
(74) *Attorney, Agent, or Firm* — Klarquist Sparkman, LLP

(57) ABSTRACT

Monoclonal antibodies and antibody fragments that specifically bind to matrilin-3, conjugates including these molecules, and nucleic acid molecules encoding the antibodies, antigen binding fragments and conjugates, are disclosed. Also disclosed are compositions including the disclosed antibodies, antigen binding fragments, conjugates, and nucleic acid molecules. Methods of treating or inhibiting a cartilage disorder in a subject, as well as methods of increasing chondrogenesis in cartilage tissue are further provided. The methods can be used, for example, for treating or inhibiting a growth plate disorder in a subject, such as a skeletal dysplasia or short stature.

98 Claims, 11 Drawing Sheets
Specification includes a Sequence Listing.

(56) References Cited

OTHER PUBLICATIONS

Kobayashi, et al. "Indian hedgehog stimulates periarticular chondrocyte differentiation to regulate growth plate length independently of PTHrP." *The Journal of Clinical Investigation* 115, No. 7 (2005): 1734-1742.

Krejci, et al. "Interaction of fibroblast growth factor and C-natriuretic peptide signaling in regulation of chondrocyte proliferation and extracellular matrix homeostasis." *Journal of Cell Science* 118, No. 21 (2005): 5089-5100.

Kronenberg. "PTHrP and skeletal development." *Annals of the New York Academy of Sciences* 1068, No. 1 (2006): 1-13.

Long, et al. "Genetic manipulation of hedgehog signaling in the endochondral skeleton reveals a direct role in the regulation of chondrocyte proliferation." *Development* 128, No. 24 (2001): 5099-5108.

Long, et al. "Independent regulation of skeletal growth by Ihh and IGF signaling." *Developmental Biology* 298, No. 1 (2006): 327-333.

Maeda, et al. "Indian Hedgehog produced by postnatal chondrocytes is essential for maintaining a growth plate and trabecular bone." *Proceedings of the National Academy of Sciences* 104, No. 15 (2007): 6382-6387.

Mak, et al. "Indian hedgehog signals independently of PTHrP to promote chondrocyte hypertrophy." *Development* 135, No. 11 (2008): 1947-1956.

Mericq, et al. "Regulation of fetal rat bone growth by C-type natriuretic peptide and cGMP." *Pediatric Research* 47, No. 2 (2000): 189-189.

Millán, et al. "Enzyme replacement therapy for murine hypophosphatasia." *Journal of Bone and Mineral Research* 23, No. 6 (2008): 777-787.

Nilsson, et al. "Gradients in bone morphogenetic protein-related gene expression across the growth plate." *Journal of Endocrinology* 193, No. 1 (2007): 75-84.

Olney, et al. "Amino-terminal propeptide of C-type natriuretic peptide and linear growth in children: effects of puberty, testosterone, and growth hormone." *The Journal of Clinical Endocrinology & Metabolism* 92, No. 11 (2007): 4294-4298.

Olney, et al. "Heterozygous mutations in natriuretic peptide receptor-B (NPR2) are associated with short stature." *The Journal of Clinical Endocrinology & Metabolism* 91, No. 4 (2006): 1229-4232.

Pi, et al. "Targeted delivery of non-viral vectors to cartilage in vivo using a chondrocyte-homing peptide identified by phage display," *Biomaterials* 32, No. 26 (2011): 6324-6332.

Rothenfluh, et al. "Biofunctional polymer nanoparticles for intra-articular targeting and retention in cartilage." *Nature Materials* 7, No. 3 (2008): 248-254.

Shakibaei, et al. "Igf-I extends the chondrogenic potential of human articular chondrocytes in vitro: molecular association between Sox9 and Erk1/2." *Biochemical Pharmacology* 72, No. 11 (2006): 1382-1395.

Teixeira, et al. "Nitric oxide, C-type natriuretic peptide and cGMP as regulators of endochondral ossification." *Developmental Biology* 319, No. 2 (2008): 171-178.

Vincourt, et al. "Matrilin-3 switches from anti-to pro-anabolic upon integration to the extracellular matrix." *Matrix Biology* 31, No. 5 (2012): 290-298.

Wagener, et al. "Primary structure of matrilin-3, a new member of a family of extracellular matrix proteins related to cartilage matrix protein (matrilin-1) and von Willebrand factor 1." *FEBS letters* 413, No. 1 (1997): 129-134.

Walsh, et al. "IGF-1 increases invasive potential of MCF 7 breast cancer cells and induces activation of latent TGF-β1 resulting in epithelial to mesenchymal transition." *Cell Communication and Signaling* 9, No. 1 (2011): 1.

Woods, et al. "C-type natriuretic peptide regulates cellular condensation and glycosaminoglycan synthesis during chondrogenesis." *Endocrinology* 148, No. 10 (2007): 5030-5041.

Wu, et al. "Nuclear factor-κB (NF-κB) p65 interacts with Stat5b in growth plate chondrocytes and mediates the effects of growth hormone on chondrogenesis and on the expression of insulin-like growth factor-1 and bone morphogenetic protein-2." *Journal of Biological Chemistry* 286, No. 28 (2011): 24726-24734.

Yadav, et al. "Dose response of bone-targeted enzyme replacement for murine hypophosphatasia." *Bone* 49, No. 2 (2011): 250-256.

Yang, et al. "Wnt5a and Wnt5b exhibit distinct activities in coordinating chondrocyte proliferation and differentiation." *Development* 130, No. 5 (2003): 1003-1015.

Yasoda, et al. "Overexpression of CNP in chondrocytes rescues achondroplasia through a MAPK-dependent pathway." *Nature Medicine* 10, No. 1 (2004): 80-86.

Yokogawa, et al. "Selective delivery of estradiol to bone by aspartic acid oligopeptide and its effects on ovariectomized mice." *Endocrinology* 142, No. 3 (2001): 1228-1233.

Yoon, et al. "Bmpr1a and Bmpr1b have overlapping functions and are essential for chondrogenesis in vivo." *Proceedings of the National Academy of Sciences of the United States of America* 102, No. 14 (2005): 5062-5067.

Yoon, et al. "BMPs regulate multiple aspects of growth-plate chondrogenesis through opposing actions on FGF pathways." *Development* 133, No. 23 (2006): 4667-4678.

Zhang, et al. "Role of estrogen receptor (ER) α in insulin-like growth factor (IGF)-I-induced responses in MCF-7 breast cancer cells." *Journal of Molecular Endocrinology* 35, No. 3 (2005): 433-447.

\* cited by examiner

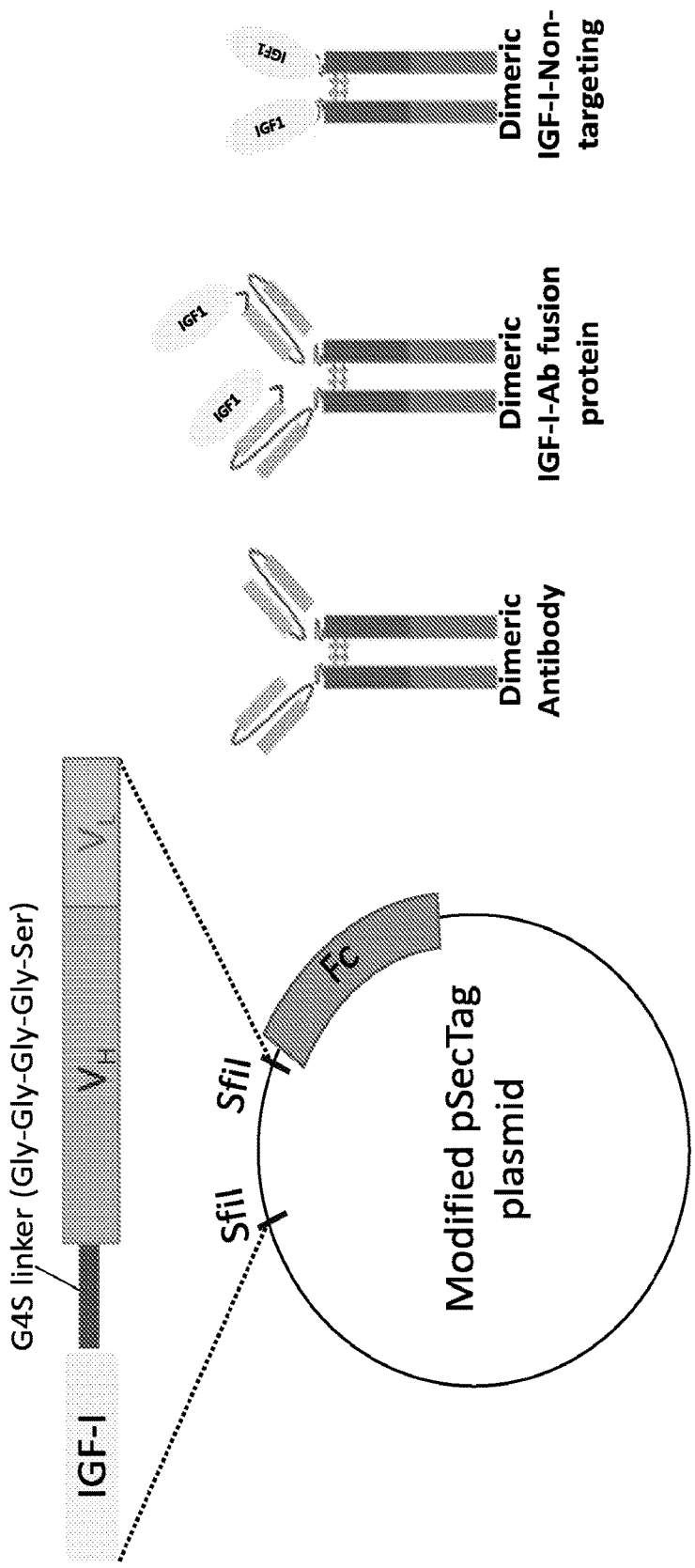

SEQUENCE LISTING

<160> NUMBER OF SEQ ID NOS: 53

<210> SEQ ID NO 1
<211> LENGTH: 117
<212> TYPE: PRT
<213> ORGANISM: Artificial Sequence
<220> FEATURE:
<223> OTHER INFORMATION: antibody heavy chain variable region

<400> SEQUENCE: 1

```
Glu Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Gly Tyr Trp Phe Asp Pro Trp Gly Gln Gly Thr Leu
            100                 105                 110

Val Thr Val Ser Ser
        115
```

<210> SEQ ID NO 2
<211> LENGTH: 108
<212> TYPE: PRT
<213> ORGANISM: Artificial Sequence
<220> FEATURE:
<223> OTHER INFORMATION: antibody light chain variable region

<400> SEQUENCE: 2

```
Asp Val Gln Leu Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
```

```
                35                  40                  45
Tyr Asp Ala Ser Asn Leu Glu Thr Gly Val Pro Ser Arg Phe Ser Gly
         50                  55                  60
Ser Gly Ser Gly Thr Asp Phe Thr Phe Thr Ile Ser Ser Leu Gln Pro
 65                  70                  75                  80
Glu Asp Ile Ala Thr Tyr Tyr Cys Gln Gln Tyr Asp Asn Leu Pro Leu
                 85                  90                  95
Thr Phe Gly Gly Gly Thr Lys Leu Glu Ile Lys Arg
            100                 105

<210> SEQ ID NO 3
<211> LENGTH: 120
<212> TYPE: PRT
<213> ORGANISM: Artificial Sequence
<220> FEATURE:
<223> OTHER INFORMATION: antibody heavy chain variable region

<400> SEQUENCE: 3

Gln Val Gln Leu Gln Gln Ser Gly Pro Gly Leu Val Lys Pro Ser Gln
 1               5                  10                  15
Thr Leu Ser Leu Thr Cys Ala Ile Ser Gly Asp Ser Val Ser Ser Asn
             20                  25                  30
Ser Ala Ala Trp Asn Trp Ile Arg Gln Ser Pro Ser Arg Gly Leu Glu
         35                  40                  45
Trp Leu Gly Arg Thr Tyr Tyr Gly Ser Lys Trp Tyr Asn Asp Tyr Ala
     50                  55                  60
Pro Ser Val Lys Ser Arg Ile Ser Ile Asn Pro Asp Thr Ser Lys Asn
 65                  70                  75                  80
Gln Phe Ser Leu Gln Leu Asn Ser Val Thr Pro Glu Asp Thr Ala Val
                 85                  90                  95
Tyr Tyr Cys Thr Arg Gly Ile Trp Asn Ala Phe Asp Ile Trp Gly Gln
            100                 105                 110
Gly Thr Met Val Thr Val Ser Ser
        115                 120

<210> SEQ ID NO 4
<211> LENGTH: 108
<212> TYPE: PRT
<213> ORGANISM: Artificial Sequence
<220> FEATURE:
<223> OTHER INFORMATION: antibody light chain variable region

<400> SEQUENCE: 4

Ser Ser Glu Leu Thr Gln Asp Pro Ala Val Ser Val Ala Leu Gly Gln
 1               5                  10                  15
Thr Val Arg Ile Thr Cys Gln Gly Asp Ser Leu Arg Ser Tyr Tyr Ala
             20                  25                  30
Ser Trp Tyr Gln Gln Lys Pro Gly Gln Ala Pro Leu Leu Val Ile Tyr
         35                  40                  45
Asp Arg Asp Asn Arg Pro Ser Gly Ile Pro Asp Arg Phe Ser Gly Ser
     50                  55                  60
Ser Ser Gly Asn Thr Ala Ser Leu Thr Ile Thr Gly Ala Gln Ala Glu
 65                  70                  75                  80
Asp Glu Ala Asp Tyr Tyr Cys Gln Ser Tyr Asp Thr Ser Leu Ser Trp
                 85                  90                  95
Val Phe Gly Gly Gly Thr Gln Leu Thr Val Leu Gly
            100                 105
```

<210> SEQ ID NO 5
<211> LENGTH: 119
<212> TYPE: PRT
<213> ORGANISM: Artificial Sequence
<220> FEATURE:
<223> OTHER INFORMATION: antibody heavy chain variable region

<400> SEQUENCE: 5

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Gly Ser Gly Ser His Ala Phe Asp Ile Trp Gly Gln Gly
            100                 105                 110

Thr Thr Val Thr Val Ser Ser
        115
```

<210> SEQ ID NO 6
<211> LENGTH: 111
<212> TYPE: PRT
<213> ORGANISM: Artificial Sequence
<220> FEATURE:
<223> OTHER INFORMATION: antibody light chain variable region

<400> SEQUENCE: 6

```
Ser Tyr Glu Leu Thr Gln Pro Pro Ser Thr Ser Gly Thr Pro Gly Gln
1               5                   10                  15

Arg Val Ala Ile Ser Cys Ser Gly Ala Ser Ser Asn Ile Gly Ser Asn
            20                  25                  30

Ala Val Ser Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Trp Val Phe Gly Gly Gly Thr Gln Leu Thr Val Leu Gly
            100                 105                 110
```

<210> SEQ ID NO 7
<211> LENGTH: 708
<212> TYPE: DNA
<213> ORGANISM: Artificial Sequence
<220> FEATURE:
<223> OTHER INFORMATION: scFv sequence

<400> SEQUENCE: 7

```
ctggtgcagt ctggggctga ggtgaagaag cctggggcct cagtgaaggt ctcctgcaag      60
gcttctggag gcaccttcag cagctatgct atcagctggg tgcgacaggc ccctggacaa     120
```

| | |
|---|---|
| gggcttgagt ggatgggagg gatcatccct atctttggta cagcaaacta cgcacagaag | 180 |
| ttccagggca gagtcacgat taccgcggac aaatccacga gcacagccta catggagctg | 240 |
| agcagcctga gatctgagga cacggccgtg tattactgtg cgagaggcca agggtattgg | 300 |
| ttcgacccct ggggccaggg aaccctggtc accgtctcct caggaggtgg cgggtctggt | 360 |
| ggaggcgcta gcagtggtgg cggatccgac gtccagttga cccagtctcc atcctccctg | 420 |
| tctgcatctg taggagacag agtcaccatc acttgccagg cgagtcagga cattagcaac | 480 |
| tatttaaatt ggtatcagca gaaaccaggg aaagccccta agctcctgat ctacgatgca | 540 |
| tccaatttgg aaacaggggt cccatcaagg ttcagtggaa gtggatctgg gacagatttt | 600 |
| actttcacca tcagcagcct gcagcctgaa gatattgcaa catattactg tcaacagtat | 660 |
| gataatctcc cgctcacttt cggcggaggg accaagctgg agatcaaa | 708 |

<210> SEQ ID NO 8
<211> LENGTH: 726
<212> TYPE: DNA
<213> ORGANISM: Artificial Sequence
<220> FEATURE:
<223> OTHER INFORMATION: scFv sequence

<400> SEQUENCE: 8

| | |
|---|---|
| caggtacagc tgcagcagtc aggtccagga ctggtgaagc cctcgcagac cctctcactc | 60 |
| acctgtgcca tctccgggga cagtgtctct agcaacagtg ctgcttggaa ctggatcagg | 120 |
| cagtccccat cgagaggcct tgagtggctg ggaaggacat actacgggtc caagtggtat | 180 |
| aatgattatg cgccatctgt gaaaagtcga ataagtatca cccagacac atccaagaac | 240 |
| cagttctccc tgcaactgaa ctctgtgact cccgaagaca cggctgtgta ttactgtaca | 300 |
| agggtattt ggaatgcttt tgatatctgg ggccaaggga caatggtcac cgtctcttca | 360 |
| ggaggtggcg gtctggtgg aggcgctagc ggtggtggcg atcctcttc tgagctgact | 420 |
| caggacccctg ctgtgtctgt ggccttggga cagacagtca ggatcacatg ccaaggagac | 480 |
| agcctcagaa gctattatgc aagctggtac cagcagaagc caggacaggc ccctttactt | 540 |
| gtcatctatg atagggacaa ccggccctca gggatcccag accgattctc tggctccagc | 600 |
| tcaggaaaca cagcttcctt gaccatcact ggggctcagg cggaagatga ggctgattat | 660 |
| tactgccagt cctatgacac cagcctgagt tgggtgttcg gcggaggcac ccagctgacc | 720 |
| gtcctc | 726 |

<210> SEQ ID NO 9
<211> LENGTH: 732
<212> TYPE: DNA
<213> ORGANISM: Artificial Sequence
<220> FEATURE:
<223> OTHER INFORMATION: scFv sequence

<400> SEQUENCE: 9

| | |
|---|---|
| gaggtccagc tggtgcagtc tggggctgag gtgaagaagc ctgggtcctc ggtgaaggtc | 60 |
| tcctgcaagg cttctggagg caccttcagc agctatgcta tcagctgggt gcgacaggcc | 120 |
| cctggacaag gcttgagtg gatgggaagg atcatccta tccttggtat agcaaactac | 180 |
| gcacagaagt tccagggcag agtcacgatt accgcggaca aatccacgag cacagcctac | 240 |
| atggagctga gcagcctgag atctgaggac acggccgtgt attactgtgc gagatggggt | 300 |
| agtgggagcc atgcttttga tatctggggc caagggacca cggtcaccgt ctcctcagga | 360 |
| ggtggcgggt ctggtggagg cgctagcagt ggtggcggat cctcctatga gctgactcag | 420 |

```
ccaccctcga cgtctgggac ccccgggcag agggtcgcca tctcttgttc tggggccagt    480
tccaatatcg gaagtaatgc tgttagctgg taccagcagc tcccaggaac ggccccccaaa   540 ctcctcatct atagcaataa tcaacggccc tcagggtgtcc ctgaccgatt ctctggctcc   600
aagtctggca cctcagcctc cctggccatc agtgggctcc ggtccgagga tgaggctgat   660
tattactgtg cagcatggga tgacagcctc aatggctggg tgttcggcgg agggacccag   720
ctcaccgttt ta                                                        732
```

<210> SEQ ID NO 10
<211> LENGTH: 236
<212> TYPE: PRT
<213> ORGANISM: Artificial Sequence
<220> FEATURE:
<223> OTHER INFORMATION: scFv sequence
<400> SEQUENCE: 10

```
Leu Val Gln Ser Gly Ala Glu Val Lys Lys Pro Gly Ala Ser Val Lys
1               5                   10                  15

Val Ser Cys Lys Ala Ser Gly Gly Thr Phe Ser Ser Tyr Ala Ile Ser
            20                  25                  30

Trp Val Arg Gln Ala Pro Gly Gln Gly Leu Glu Trp Met Gly Gly Ile
        35                  40                  45

Ile Pro Ile Phe Gly Thr Ala Asn Tyr Ala Gln Lys Phe Gln Gly Arg
    50                  55                  60

Val Thr Ile Thr Ala Asp Lys Ser Thr Ser Thr Ala Tyr Met Glu Leu
65                  70                  75                  80

Ser Ser Leu Arg Ser Glu Asp Thr Ala Val Tyr Tyr Cys Ala Arg Gly
                85                  90                  95

Gln Gly Tyr Trp Phe Asp Pro Trp Gly Gln Gly Thr Leu Val Thr Val
            100                 105                 110

Ser Ser Gly Gly Gly Gly Ser Gly Gly Gly Ala Ser Ser Gly Gly Gly
        115                 120                 125

Ser Asp Val Gln Leu Thr Gln Ser Pro Ser Ser Leu Ser Ala Ser Val
    130                 135                 140

Gly Asp Arg Val Thr Ile Thr Cys Gln Ala Ser Gln Asp Ile Ser Asn
145                 150                 155                 160

Tyr Leu Asn Trp Tyr Gln Gln Lys Pro Gly Lys Ala Pro Lys Leu Leu
                165                 170                 175

Ile Tyr Asp Ala Ser Asn Leu Glu Thr Gly Val Pro Ser Arg Phe Ser
            180                 185                 190

Gly Ser Gly Ser Gly Thr Asp Phe Thr Phe Thr Ile Ser Ser Leu Gln
        195                 200                 205

Pro Glu Asp Ile Ala Thr Tyr Tyr Cys Gln Gln Tyr Asp Asn Leu Pro
    210                 215                 220

Leu Thr Phe Gly Gly Gly Thr Lys Leu Glu Ile Lys
225                 230                 235
```

<210> SEQ ID NO 11
<211> LENGTH: 239
<212> TYPE: PRT
<213> ORGANISM: Artificial Sequence
<220> FEATURE:
<223> OTHER INFORMATION: scFv sequence
<400> SEQUENCE: 11

```
Leu Gln Gln Ser Gly Pro Gly Leu Val Lys Pro Ser Gln Thr Leu Ser
```

```
                1               5                  10                 15
Leu Thr Cys Ala Ile Ser Gly Asp Ser Val Ser Ser Asn Ser Ala Ala
                20                 25                 30

Trp Asn Trp Ile Arg Gln Ser Pro Ser Arg Gly Leu Glu Trp Leu Gly
            35                 40                 45

Arg Thr Tyr Tyr Gly Ser Lys Trp Tyr Asn Asp Tyr Ala Pro Ser Val
        50                 55                 60

Lys Ser Arg Ile Ser Ile Asn Pro Asp Thr Ser Lys Asn Gln Phe Ser
65                 70                 75                 80

Leu Gln Leu Asn Ser Val Thr Pro Glu Asp Thr Ala Val Tyr Tyr Cys
                85                 90                 95

Thr Arg Gly Ile Trp Asn Ala Phe Asp Ile Trp Gly Gln Gly Thr Met
                100                105                110

Val Thr Val Ser Ser Gly Gly Gly Ser Gly Gly Ala Ser Gly
            115                120                125

Gly Gly Gly Ser Ser Glu Leu Thr Gln Asp Pro Ala Val Ser Val
130                135                140

Ala Leu Gly Gln Thr Val Arg Ile Thr Cys Gln Gly Asp Ser Leu Arg
145                150                155                160

Ser Tyr Tyr Ala Ser Trp Tyr Gln Gln Lys Pro Gly Gln Ala Pro Leu
                165                170                175

Leu Val Ile Tyr Asp Arg Asp Asn Arg Pro Ser Gly Ile Pro Asp Arg
                180                185                190

Phe Ser Gly Ser Ser Ser Gly Asn Thr Ala Ser Leu Thr Ile Thr Gly
            195                200                205

Ala Gln Ala Glu Asp Glu Ala Asp Tyr Tyr Cys Gln Ser Tyr Asp Thr
        210                215                220

Ser Leu Ser Trp Val Phe Gly Gly Gly Thr Gln Leu Thr Val Leu
225                230                235

<210> SEQ ID NO 12
<211> LENGTH: 241
<212> TYPE: PRT
<213> ORGANISM: Artificial Sequence
<220> FEATURE:
<223> OTHER INFORMATION: scFv sequence

<400> SEQUENCE: 12

Leu Val Gln Ser Gly Ala Glu Val Lys Lys Pro Gly Ser Ser Val Lys
1               5                  10                 15

Val Ser Cys Lys Ala Ser Gly Gly Thr Phe Ser Ser Tyr Ala Ile Ser
                20                 25                 30

Trp Val Arg Gln Ala Pro Gly Gln Gly Leu Glu Trp Met Gly Arg Ile
            35                 40                 45

Ile Pro Ile Leu Gly Ile Ala Asn Tyr Ala Gln Lys Phe Gln Gly Arg
        50                 55                 60

Val Thr Ile Thr Ala Asp Lys Ser Thr Ser Thr Ala Tyr Met Glu Leu
65                 70                 75                 80

Ser Ser Leu Arg Ser Glu Asp Thr Ala Val Tyr Tyr Cys Ala Arg Trp
                85                 90                 95

Gly Ser Gly Ser His Ala Phe Asp Ile Trp Gly Gln Gly Thr Thr Val
                100                105                110

Thr Val Ser Ser Gly Gly Gly Gly Ser Gly Gly Gly Ala Ser Ser Gly
            115                120                125

Gly Gly Ser Ser Tyr Glu Leu Thr Gln Pro Pro Ser Thr Ser Gly Thr
```

```
                130                 135                 140
Pro Gly Gln Arg Val Ala Ile Ser Cys Ser Gly Ala Ser Ser Asn Ile
145                 150                 155                 160

Gly Ser Asn Ala Val Ser Trp Tyr Gln Gln Leu Pro Gly Thr Ala Pro
                165                 170                 175

Lys Leu Leu Ile Tyr Ser Asn Asn Gln Arg Pro Ser Gly Val Pro Asp
                180                 185                 190

Arg Phe Ser Gly Ser Lys Ser Gly Thr Ser Ala Ser Leu Ala Ile Ser
                195                 200                 205

Gly Leu Arg Ser Glu Asp Glu Ala Asp Tyr Tyr Cys Ala Ala Trp Asp
                210                 215                 220

Asp Ser Leu Asn Gly Trp Val Phe Gly Gly Gly Thr Gln Leu Thr Val
225                 230                 235                 240

Leu
```

<210> SEQ ID NO 13
<211> LENGTH: 1465
<212> TYPE: DNA
<213> ORGANISM: Artificial Sequence
<220> FEATURE:
<223> OTHER INFORMATION: scFv-Fc sequence

<400> SEQUENCE: 13

```
ctggtgcagt ctggggctga ggtgaagaag cctggggcct cagtgaaggt ctcctgcaag      60
gcttctggag gcaccttcag cagctatgct atcagctggg tgcgacaggc ccctggacaa     120
gggcttgagt ggatgggagg gatcatccct atctttggta cagcaaacta cgcacagaag     180
ttccagggca gagtcacgat taccgcggac aaatccacga gcacagccta catggagctg     240
agcagcctga gatctgagga cacggccgtg tattactgtg cgagaggcca agggtattgg     300
ttcgacccct ggggccaggg aaccctggtc accgtctcct caggaggtgg cgggtctggt     360
ggaggcgcta gcagtggtgg cggatccgac gtccagttga cccagtctcc atcctccctg     420
tctgcatctg taggagacag agtcaccatc acttgccagg cgagtcagga cattagcaac     480
tatttaaatt ggtatcagca gaaaccaggg aaagccccta agctcctgat ctacgatgca     540
tccaatttgg aaacaggggt cccatcaagg ttcagtggaa gtggatctgg gacagatttt     600
actttcacca tcagcagcct gcagcctgaa gatattgcaa catattactg tcaacagtat     660
gataatctcc cgctcacttt cggcggaggg accaagctgg agatcaaacg tggccaggcc     720
ggccaagggc ccgacaaaac tcacacatgc ccaccgtgcc cagcacctga actcctgggg     780
ggaccgtcag tcttcctctt ccccccaaaa cccaaggaca cctcatgat ctcccggacc     840
cctgaggtca catgcgtggt ggtggacgtg agccacgaag accctgaggt caagttcaac     900
tggtacgtgg acggcgtgga ggtgcataat gccaagacaa agccgcggga ggagcagtac     960
aacagcacgt accgtgtggt cagcgtcctc accgtcctgc accaggactg gctgaatggc    1020
aaggagtaca agtgcaaggt ctccaacaaa gccctcccag cccccatcga gaaaaccatc    1080
tccaaagcca aagggcagcc ccgagaacca caggtgtaca ccctgccccc atcccgggat    1140
gagctgacca agaaccaggt cagcctgacc tgcctggtca aaggcttcta tcccagcgac    1200
atcgccgtgg agtgggagag caatgggcag ccggagaaca actacaagac cacgcctccc    1260
gtgctggact ccgacggctc cttcttcctc tacagcaagc tcaccgtgga caagagcagg    1320
tggcagcagg ggaacgtctt ctcatgctcc gtgatgcatg aggctctgca caaccactac    1380
acgcagaaga gcctctccct gtctcggggt aaagcggccg ctcgaggact aaacgacatc    1440
```
ttcgaggctc agaaaatcga atgca                                          1465

<210> SEQ ID NO 14
<211> LENGTH: 1482
<212> TYPE: DNA
<213> ORGANISM: Artificial Sequence
<220> FEATURE:
<223> OTHER INFORMATION: scFv-Fc sequence

<400> SEQUENCE: 14
caggtacagc tgcagcagtc aggtccagga ctggtgaagc cctcgcagac cctctcactc     60
acctgtgcca tctccgggga cagtgtctct agcaacagtg ctgcttggaa ctggatcagg    120
cagtccccat cgagaggcct tgagtggctg ggaaggacat actacgggtc aagtggtat     180
aatgattatg cgccatctgt gaaaagtcga ataagtatca acccagacac atccaagaac    240
cagttctccc tgcaactgaa ctctgtgact cccgaagaca cggctgtgta ttactgtaca    300
aggggtattt ggaatgcttt tgatatctgg ggccaaggga caatggtcac cgtctcttca    360
ggaggtggcg gtctggtgg aggcgctagc ggtggtggcg gatcctcttc tgagctgact    420
caggaccctg ctgtgtctgt ggccttggga cagacagtca ggatcacatg ccaaggagac    480
agcctcagaa gctattatgc aagctggtac cagcagaagc caggacaggc ccctttactt    540
gtcatctatg atagggacaa ccggccctca gggatcccag accgattctc tggctccagc    600
tcaggaaaca cagcttcctt gaccatcact ggggctcagg cggaagatga ggctgattat    660
tactgccagt cctatgacac cagcctgagt tgggtgttcg gcggaggcac ccagctgacc    720
gtcctcggtg gccaggccgg ccaagggccc gacaaaactc acacatgccc accgtgccca    780
gcacctgaac tcctgggggg accgtcagtc ttcctcttcc cccaaaaccc aaggacacc    840
ctcatgatct cccggacccc tgaggtcaca tgcgtggtgg tggacgtgag ccacgaagac    900
cctgaggtca agttcaactg gtacgtggac ggcgtggagg tgcataatgc caagacaaag    960
ccgcgggagg agcagtacaa cagcacgtac cgtgtggtca gcgtcctcac cgtcctgcac   1020
caggactggc tgaatggcaa ggagtacaag tgcaaggtct ccaacaaagc cctcccagcc   1080
cccatcgaga aaaccatctc caaagccaaa gggcagcccc gagaaccaca ggtgtacacc   1140
ctgcccccat cccgggatga gctgaccaag aaccaggtca gcctgactgc ctggtcaaag   1200
gcttctatcc cagcgacatc gccgtggagt gggagcaa tgggcagccg gagaacaact    1260
acaagaccac gcctcccgtg ctggactccg acggctcctt cttcctctac agcaagctca   1320
ccgtggacaa gagcaggtgg cagcagggga acgtcttctc atgctccgtg atgcatgagg   1380
ctctgcacaa ccactacacg cagaagagcc tctccctgtc tccgggtaaa gcggccgctc   1440
gaggactaaa cgacatcttc gaggctcaga aatcgaagg ca                        1482

<210> SEQ ID NO 15
<211> LENGTH: 1489
<212> TYPE: DNA
<213> ORGANISM: Artificial Sequence
<220> FEATURE:
<223> OTHER INFORMATION: scFv-Fc sequence

<400> SEQUENCE: 15
gaggtccagc tggtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag ggcttgagtg gatgggaagg atcatcccta tccttggtat agcaaactac    180

```
gcacagaagt tccagggcag agtcacgatt accgcggaca atccacgag cacagcctac    240 atggagctga gcagcctgag atctgaggac acggccgtgt attactgtgc gagatggggt    300
agtgggagcc atgcttttga tatctggggc caagggacca cggtcaccgt ctcctcagga    360
ggtggcgggt ctggtggagg cgctagcagt ggtggcggat cctcctatga gctgactcag    420
ccaccctcga cgtctgggac cccgggcag agggtcgcca tctcttgttc tggggccagt    480
tccaatatcg gaagtaatgc tgttagctgg taccagcagc tcccaggaac ggcccccaaa    540
ctcctcatct atagcaataa tcaacggccc tcaggggtcc ctgaccgatt ctctggctcc    600
aagtctggca cctcagcctc cctggccatc agtgggctcc ggtccgagga tgaggctgat    660
tattactgtg cagcatggga tgacagcctc aatggctggg tgttcggcgg agggacccag    720
ctcaccgttt taggtggcca ggccggccaa gggcccgaca aaactcacac atgcccaccg    780
tgcccagcac ctgaactcct gggggaccg tcagtcttcc tcttccccc caaacccaag    840 gacaccctca tgatctcccg gacccctgag gtcacatgcg tggtggtgga cgtgagccac    900
gaagaccctg aggtcaagtt caactggtac gtggacggcg tggaggtgca taatgccaag    960
acaaagccgc gggaggagca gtacaacagc acgtaccgtg tggtcagcgt cctcaccgtc   1020
ctgcaccagg actggctgaa tggcaaggag tacaagtgca aggtctccaa caaagccctc   1080
ccagccccca tcgagaaaac catctccaaa gccaaagggc agccccgaga accacaggtg   1140
tacaccctgc ccccatcccg ggatgagctg accaagaacc aggtcagcct gacctgcctg   1200
gtcaaaggct tctatcccag cgacatcgcc gtggagtggg agagcaatgg gcagccggag   1260
aacaactaca agaccacgcc tcccgtgctg gactccgacg gctccttctt cctctacagc   1320
aagctcaccg tggacaagag caggtggcag caggggaacg tcttctcatg ctccgtgatg   1380
catgaggctc tgcacaacca ctacacgcag aagagcctct ccctgtctcc gggtaaagcg   1440
gccgctcgag gactaaacga catcttcgag gctcagaaaa tcgaaggca               1489
```

<210> SEQ ID NO 16
<211> LENGTH: 486
<212> TYPE: PRT
<213> ORGANISM: homo sapiens

<400> SEQUENCE: 16

```
Met Pro Arg Pro Ala Pro Ala Arg Arg Leu Pro Gly Leu Leu Leu Leu
1               5                   10                  15

Leu Trp Pro Leu Leu Leu Leu Pro Ser Ala Ala Pro Asp Pro Val Ala
            20                  25                  30

Arg Pro Gly Phe Arg Arg Leu Glu Thr Arg Gly Pro Gly Gly Ser Pro
        35                  40                  45

Gly Arg Arg Pro Ser Pro Ala Ala Pro Asp Gly Ala Pro Ala Ser Gly
    50                  55                  60

Thr Ser Glu Pro Gly Arg Ala Arg Gly Ala Gly Val Cys Lys Ser Arg
65                  70                  75                  80

Pro Leu Asp Leu Val Phe Ile Ile Asp Ser Ser Arg Ser Val Arg Pro
                85                  90                  95

Leu Glu Phe Thr Lys Val Lys Thr Phe Val Ser Arg Ile Ile Asp Thr
            100                 105                 110

Leu Asp Ile Gly Pro Ala Asp Thr Arg Val Ala Val Val Asn Tyr Ala
        115                 120                 125

Ser Thr Val Lys Ile Glu Phe Gln Leu Gln Ala Tyr Thr Asp Lys Gln
    130                 135                 140
```

Ser Leu Lys Gln Ala Val Gly Arg Ile Thr Pro Leu Ser Thr Gly Thr
145                 150                 155                 160

Met Ser Gly Leu Ala Ile Gln Thr Ala Met Asp Glu Ala Phe Thr Val
            165                 170                 175

Glu Ala Gly Ala Arg Glu Pro Ser Ser Asn Ile Pro Lys Val Ala Ile
        180                 185                 190

Ile Val Thr Asp Gly Arg Pro Gln Asp Gln Val Asn Glu Val Ala Ala
    195                 200                 205

Arg Ala Gln Ala Ser Gly Ile Glu Leu Tyr Ala Val Gly Val Asp Arg
210                 215                 220

Ala Asp Met Ala Ser Leu Lys Met Met Ala Ser Glu Pro Leu Glu Glu
225                 230                 235                 240

His Val Phe Tyr Val Glu Thr Tyr Gly Val Ile Glu Lys Leu Ser Ser
                245                 250                 255

Arg Phe Gln Glu Thr Phe Cys Ala Leu Asp Pro Cys Val Leu Gly Thr
            260                 265                 270

His Gln Cys Gln His Val Cys Ile Ser Asp Gly Glu Gly Lys His His
        275                 280                 285

Cys Glu Cys Ser Gln Gly Tyr Thr Leu Asn Ala Asp Lys Lys Thr Cys
    290                 295                 300

Ser Ala Leu Asp Arg Cys Ala Leu Asn Thr His Gly Cys Glu His Ile
305                 310                 315                 320

Cys Val Asn Asp Arg Ser Gly Ser Tyr His Cys Glu Cys Tyr Glu Gly
                325                 330                 335

Tyr Thr Leu Asn Glu Asp Arg Lys Thr Cys Ser Ala Gln Asp Lys Cys
            340                 345                 350

Ala Leu Gly Thr His Gly Cys Gln His Ile Cys Val Asn Asp Arg Thr
        355                 360                 365

Gly Ser His His Cys Glu Cys Tyr Glu Gly Tyr Thr Leu Asn Ala Asp
    370                 375                 380

Lys Lys Thr Cys Ser Val Arg Asp Lys Cys Ala Leu Gly Ser His Gly
385                 390                 395                 400

Cys Gln His Ile Cys Val Ser Asp Gly Ala Ala Ser Tyr His Cys Asp
                405                 410                 415

Cys Tyr Pro Gly Tyr Thr Leu Asn Glu Asp Lys Lys Thr Cys Ser Ala
            420                 425                 430

Thr Glu Glu Ala Arg Arg Leu Val Ser Thr Glu Asp Ala Cys Gly Cys
        435                 440                 445

Glu Ala Thr Leu Ala Phe Gln Asp Lys Val Ser Ser Tyr Leu Gln Arg
    450                 455                 460

Leu Asn Thr Lys Leu Asp Asp Ile Leu Glu Lys Leu Lys Ile Asn Glu
465                 470                 475                 480

Tyr Gly Gln Ile His Arg
                485

<210> SEQ ID NO 17
<211> LENGTH: 2600
<212> TYPE: DNA
<213> ORGANISM: homo sapiens

<400> SEQUENCE: 17
aaatccgagc ctcgcgtggg ctcctggccc ccgacggaca ccaccaggcc cacggagccc      60
accatgccgc gccggccccc cgcgcgccgc ctcccgggac tcctcctgct gctctggccg     120
ctgctgctgc tgccctccgc cgcccccgac cccgtggccc gcccgggctt ccggaggctg     180

```
gagacccgag gtcccggggg cagccctgga cgccgcccct ctcctgcggc tcccgacggc    240
gcgcccgctt ccgggaccag cgagcctggc cgcgcccgcg gtgcaggtgt ttgcaagagc    300
agacccttgg acctggtgtt tatcattgat agttctcgta gcgtacggcc cctggaattc    360
accaaagtga aaacttttgt ctcccggata atcgacactc tggacattgg gccagccgac    420
acgcgggtgg cagtggtgaa ctatgctagc actgtgaaga tcgagttcca actccaggcc    480
tacacagata agcagtccct gaagcaggcc gtgggtcgaa tcacacccct gtcaacaggc    540
accatgtcag gcctagccat ccagacagca atggacgaag ccttcacagt ggaggcaggg    600
gctcgagagc cctcttctaa catccctaag gtggccatca ttgttacaga tgggaggccc    660
caggaccagg tgaatgaggt ggcggctcgg gcccaagcat ctggtattga gctctatgct    720
gtgggcgtgg accgggcaga catggcgtcc ctcaagatga tggccagtga gccctagag    780 gagcatgttt tctacgtgga gacctatggg gtcattgaga aactttcctc tagattccag    840
gaaaccttct gtgcgctgga cccctgtgtg cttggaacac accagtgcca gcacgtctgc    900
atcagtgatg gggaaggcaa gcaccactgt gagtgtagcc aaggatacac cttgaatgcc    960
gacaagaaaa cgtgttcagc tcttgatagg tgtgctctta cacccacgg atgtgagcac   1020 atctgtgtga atgacagaag tggctcttat cattgtgagt gctatgaagg ttataccttg   1080
aatgaagaca ggaaaacttg ttcagctcaa gataaatgtg ctttgggtac ccatgggtgt   1140
cagcacattt gtgtgaatga cagaacaggg tcccatcatt gtgaatgcta tgagggctac   1200
actctgaatg cagataaaaa aacatgttca gtccgtgaca agtgtgccct aggctctcat   1260
ggttgccagc acatttgtgt gagtgatggg gccgcatcct accactgtga ttgctatcct   1320
ggctacacct taaatgagga caagaaaaca tgttcagcca ctgaggaagc acgaagactt   1380
gtttccactg aagatgcttg tggatgtgaa gctacactgg cattccagga caaggtcagc   1440
tcgtatcttc aaagactgaa cactaaactt gatgacattt tggagaagtt gaaaataaat   1500
gaatatggac aaatacatcg ttaaattgct ccaatttctc acctgaaaat gtggacagct   1560
tggtgtactt aatactcatg cattcttttg cacacctgtt attgccaatg ttcctgctaa   1620
taatttgcca ttatctgtat taatgcttga atattactgg ataaattgta tgaagatctt   1680
ctgcagaatc agcatgattc ttccaaggaa atacatatgc agatacttat taagagcaaa   1740
ctttagtgtc tctaagttat gactgtgaaa tgattggtag gaaatagaat gaaagttta    1800 gtgtttcttt atctactaat tgagccattt aattttaaa tgtttatatt agataaccat   1860
attcacaatg gaaactttag gtctagtttc ttttgatagt atttataata taaatcaatc   1920
ttattactga gagtgcaaat tgtacaaggt atttacacat acaacttcat ataactgaga   1980
tgaatgtaat tttgaactgt ttaacacttt ttgttttttg cttatttgt tggagtatta    2040 ttgaagatgt gatcaataga ttgtaataca catatctaaa aatagttaac acagatcaag   2100
tgaacattac attgccattt ttaattcatt ctggtctttg aaagaaatgt actactaaag   2160
agcactagtt gtgaatttag ggtgttaaac ttttaccaa gtacaaaaat cccaaattca    2220
ctttattatt ttgcttcagg atccaagtga caaagttata tatttataaa attgctataa   2280
atcgacaaaa tctaatgttg tcttttttaat gttagtgatc cacctgcctc agcctcccaa   2340
agtgctggga ttacaggctt gaaagtctaa ctttttttta cttatatatt tgatacatat   2400
aattcttttg gctttgaaac ttgcaacttt gagaacaaaa cagtccttta aattttgcac   2460
tgctcaattc tgttttttcgt ttgcattgtc tttaatataa taaaagttat tacctttaca   2520
```

-continued

```
tattatcatg tctattttg atgactcatc aatttgtct attaaagata tttctttaaa    2580
ttaaaaaaaa aaaaaaaaaa                                               2600
```

<210> SEQ ID NO 18
<211> LENGTH: 217
<212> TYPE: PRT
<213> ORGANISM: homo sapiens

<400> SEQUENCE: 18

```
Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215
```

<210> SEQ ID NO 19
<211> LENGTH: 191
<212> TYPE: PRT
<213> ORGANISM: homo sapiens

<400> SEQUENCE: 19

```
Phe Pro Thr Ile Pro Leu Ser Arg Leu Phe Asp Asn Ala Met Leu Arg
 1               5                  10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95
```

-continued

Phe Ala Asn Ser Leu Val Tyr Gly Ala Ser Asp Ser Asn Val Tyr Asp
               100                 105                 110

Leu Leu Lys Asp Leu Glu Glu Gly Ile Gln Thr Leu Met Gly Arg Leu
           115                 120                 125

Glu Asp Gly Ser Pro Arg Thr Gly Gln Ile Phe Lys Gln Thr Tyr Ser
       130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
               165                 170                 175

Leu Arg Ile Val Gln Cys Arg Ser Val Glu Gly Ser Cys Gly Phe
           180                 185                 190

<210> SEQ ID NO 20
<211> LENGTH: 822
<212> TYPE: DNA
<213> ORGANISM: homo sapiens

<400> SEQUENCE: 20
aggatcccaa ggcccaactc ccgaaccac tcagggtcct gtggacagct cacctagctg    60
caatggctac aggctcccgg acgtccctgc tcctggcttt tggcctgctc tgcctgccct   120
ggcttcaaga gggcagtgcc ttcccaacca ttcccttatc caggcttttt gacaacgcta   180
tgctccgcgc ccatcgtctg caccagctgg cctttgacac ctaccaggag tttgaagaag   240
cctatatccc aaaggaacag aagtattcat tcctgcagaa ccccagacc tccctctgtt    300
tctcagagtc tattccgaca ccctccaaca gggaggaaac acaacagaaa tccaacctag   360
agctgctccg catctccctg ctgctcatcc agtcgtggct ggagcccgtg cagttcctca   420
ggagtgtctt cgccaacagc ctggtgtacg gcgcctctga cagcaacgtc tatgacctcc   480
taaaggacct agaggaaggc atccaaacgc tgatggggag gctggaagat ggcagccccc   540
ggactgggca gatcttcaag cagacctaca gcaagttcga cacaaactca cacaacgatg   600
acgcactact caagaactac ggctgctct actgcttcag gaaggacatg gacaaggtcg   660
agacattcct gcgcatcgtg cagtgccgct ctgtggaggg cagctgtggc ttctagctgc   720
ccgggtggca tccctgtgac ccctccccag tgcctctcct ggccctggaa gttgccactc   780
cagtgcccac cagccttgtc ctaataaaat taagttgcat ca                     822

<210> SEQ ID NO 21
<211> LENGTH: 195
<212> TYPE: PRT
<213> ORGANISM: homo sapiens

<400> SEQUENCE: 21

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
               20                  25                  30

Phe Tyr Leu Ala Leu Cys Leu Leu Thr Phe Thr Ser Ser Ala Thr Ala
           35                  40                  45

Gly Pro Glu Thr Leu Cys Gly Ala Glu Leu Val Asp Ala Leu Gln Phe
       50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys

```
                    85                  90                  95
Phe Arg Ser Cys Asp Leu Arg Arg Leu Glu Met Tyr Cys Ala Pro Leu
            100                 105                 110
Lys Pro Ala Lys Ser Ala Arg Ser Val Arg Ala Gln Arg His Thr Asp
            115                 120                 125
Met Pro Lys Thr Gln Lys Tyr Gln Pro Pro Ser Thr Asn Lys Asn Thr
        130                 135                 140
Lys Ser Gln Arg Arg Lys Gly Trp Pro Lys Thr His Pro Gly Gly Glu
145                 150                 155                 160
Gln Lys Glu Gly Thr Glu Ala Ser Leu Gln Ile Arg Gly Lys Lys
                165                 170                 175
Glu Gln Arg Arg Glu Ile Gly Ser Arg Asn Ala Glu Cys Arg Gly Lys
            180                 185                 190
Lys Gly Lys
        195

<210> SEQ ID NO 22
<211> LENGTH: 70
<212> TYPE: PRT
<213> ORGANISM: homo sapiens

<400> SEQUENCE: 22

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65                  70

<210> SEQ ID NO 23
<211> LENGTH: 725
<212> TYPE: DNA
<213> ORGANISM: homo sapiens

<400> SEQUENCE: 23
cttcagaagc aatgggaaaa atcagcagtc ttccaaccca attatttaag tgctgctttt     60
gtgatttctt gaaggtgaag atgcacacca tgtcctcctc gcatctcttc tacctggcgc    120
tgtgcctgct caccttcacc agctctgcca cggctggacc ggagacgctc tgcggggctg    180
agctggtgga tgctcttcag ttcgtgtgtg agacaggggg cttttatttc aacaagccca    240
cagggtatgg ctccagcagt cggagggcgc ctcagacagg tatcgtggat gagtgctgct    300
tccggagctg tgatctaagg aggctggaga tgtattgcgc acccctcaag cctgccaagt    360
cagctcgctc tgtccgtgcc cagcgccaca ccgacatgcc caagacccag aaggaagtac    420
atttgaagaa cgcaagtaga gggagtgcag gaaacaagaa ctacaggatg taggaagacc    480
ctcctgagga gtgaagagtg acatgccacc gcaggatcct tgctctgca cgagttacct    540
gttaaacttt ggaacaccta ccaaaaaata agtttgataa catttaaaag atgggcgttt    600
ccccaatga aatacacaag taaacattcc aacattgtct ttaggagtga tttgcacctt    660
gcaaaaatgg tcctggagtt ggtagattgc tgttgatctt ttatcaataa tgttctatag    720
aaaag                                                                725
```

<210> SEQ ID NO 24
<211> LENGTH: 411
<212> TYPE: PRT
<213> ORGANISM: homo sapiens

<400> SEQUENCE: 24

```
Met Ser Pro Ala Arg Leu Arg Pro Arg Leu His Phe Cys Leu Val Leu
1               5                   10                  15

Leu Leu Leu Leu Val Val Pro Ala Ala Trp Gly Cys Gly Pro Gly Arg
            20                  25                  30

Val Val Gly Ser Arg Arg Arg Pro Pro Arg Lys Leu Val Pro Leu Ala
        35                  40                  45

Tyr Lys Gln Phe Ser Pro Asn Val Pro Glu Lys Thr Leu Gly Ala Ser
50                  55                  60

Gly Arg Tyr Glu Gly Lys Ile Ala Arg Ser Ser Glu Arg Phe Lys Glu
65                  70                  75                  80

Leu Thr Pro Asn Tyr Asn Pro Asp Ile Ile Phe Lys Asp Glu Glu Asn
                85                  90                  95

Thr Gly Ala Asp Arg Leu Met Thr Gln Arg Cys Lys Asp Arg Leu Asn
            100                 105                 110

Ser Leu Ala Ile Ser Val Met Asn Gln Trp Pro Gly Val Lys Leu Arg
        115                 120                 125

Val Thr Glu Gly Trp Asp Glu Asp Gly His His Ser Glu Glu Ser Leu
130                 135                 140

His Tyr Glu Gly Arg Ala Val Asp Ile Thr Thr Ser Asp Arg Asp Arg
145                 150                 155                 160

Asn Lys Tyr Gly Leu Leu Ala Arg Leu Ala Val Glu Ala Gly Phe Asp
                165                 170                 175

Trp Val Tyr Tyr Glu Ser Lys Ala His Val His Cys Ser Val Lys Ser
            180                 185                 190

Glu His Ser Ala Ala Ala Lys Thr Gly Gly Cys Phe Pro Ala Gly Ala
        195                 200                 205

Gln Val Arg Leu Glu Ser Gly Ala Arg Val Ala Leu Ser Ala Val Arg
210                 215                 220

Pro Gly Asp Arg Val Leu Ala Met Gly Glu Asp Gly Ser Pro Thr Phe
225                 230                 235                 240

Ser Asp Val Leu Ile Phe Leu Asp Arg Glu Pro His Arg Leu Arg Ala
                245                 250                 255

Phe Gln Val Ile Glu Thr Gln Asp Pro Pro Arg Arg Leu Ala Leu Thr
            260                 265                 270

Pro Ala His Leu Leu Phe Thr Ala Asp Asn His Thr Glu Pro Ala Ala
        275                 280                 285

Arg Phe Arg Ala Thr Phe Ala Ser His Val Gln Pro Gly Gln Tyr Val
290                 295                 300

Leu Val Ala Gly Val Pro Gly Leu Gln Pro Ala Arg Val Ala Ala Val
305                 310                 315                 320

Ser Thr His Val Ala Leu Gly Ala Tyr Ala Pro Leu Thr Lys His Gly
                325                 330                 335

Thr Leu Val Val Glu Asp Val Val Ser Cys Phe Ala Ala Val Ala
            340                 345                 350

Asp His His Leu Ala Gln Leu Ala Phe Trp Pro Leu Arg Leu Phe His
        355                 360                 365

Ser Leu Ala Trp Gly Ser Trp Thr Pro Gly Glu Gly Val His Trp Tyr
```

-continued

```
                    370                 375                 380
Pro Gln Leu Leu Tyr Arg Leu Gly Arg Leu Leu Glu Glu Gly Ser
385                 390                 395                 400

Phe His Pro Leu Gly Met Ser Gly Ala Gly Ser
                    405                 410

<210> SEQ ID NO 25
<211> LENGTH: 383
<212> TYPE: PRT
<213> ORGANISM: homo sapiens

<400> SEQUENCE: 25

Gly Pro Gly Arg Val Val Gly Ser Arg Arg Pro Pro Arg Lys Leu
1               5                   10                  15

Val Pro Leu Ala Tyr Lys Gln Phe Ser Pro Asn Val Pro Glu Lys Thr
                20                  25                  30

Leu Gly Ala Ser Gly Arg Tyr Glu Gly Lys Ile Ala Arg Ser Ser Glu
                35                  40                  45

Arg Phe Lys Glu Leu Thr Pro Asn Tyr Asn Pro Asp Ile Ile Phe Lys
50                  55                  60

Asp Glu Glu Asn Thr Gly Ala Asp Arg Leu Met Thr Gln Arg Cys Lys
65                  70                  75                  80

Asp Arg Leu Asn Ser Leu Ala Ile Ser Val Met Asn Gln Trp Pro Gly
                85                  90                  95

Val Lys Leu Arg Val Thr Glu Gly Trp Asp Glu Asp Gly His His Ser
                100                 105                 110

Glu Glu Ser Leu His Tyr Glu Gly Arg Ala Val Asp Ile Thr Thr Ser
                115                 120                 125

Asp Arg Asp Arg Asn Lys Tyr Gly Leu Leu Ala Arg Leu Ala Val Glu
130                 135                 140

Ala Gly Phe Asp Trp Val Tyr Tyr Glu Ser Lys Ala His Val His Cys
145                 150                 155                 160

Ser Val Lys Ser Glu His Ser Ala Ala Lys Thr Gly Gly Cys Phe
                165                 170                 175

Pro Ala Gly Ala Gln Val Arg Leu Glu Ser Gly Ala Arg Val Ala Leu
                180                 185                 190

Ser Ala Val Arg Pro Gly Asp Arg Val Leu Ala Met Gly Glu Asp Gly
                195                 200                 205

Ser Pro Thr Phe Ser Asp Val Leu Ile Phe Leu Asp Arg Glu Pro His
210                 215                 220

Arg Leu Arg Ala Phe Gln Val Ile Glu Thr Gln Asp Pro Pro Arg Arg
225                 230                 235                 240

Leu Ala Leu Thr Pro Ala His Leu Leu Phe Thr Ala Asp Asn His Thr
                245                 250                 255

Glu Pro Ala Ala Arg Phe Arg Ala Thr Phe Ala Ser His Val Gln Pro
                260                 265                 270

Gly Gln Tyr Val Leu Val Ala Gly Val Pro Gly Leu Gln Pro Ala Arg
                275                 280                 285

Val Ala Ala Val Ser Thr His Val Ala Leu Gly Ala Tyr Ala Pro Leu
290                 295                 300

Thr Lys His Gly Thr Leu Val Val Glu Asp Val Val Ala Ser Cys Phe
305                 310                 315                 320

Ala Ala Val Ala Asp His His Leu Ala Gln Leu Ala Phe Trp Pro Leu
                325                 330                 335
```

```
        Arg Leu Phe His Ser Leu Ala Trp Gly Ser Trp Thr Pro Gly Glu Gly
                        340                 345                 350

Val His Trp Tyr Pro Gln Leu Leu Tyr Arg Leu Gly Arg Leu Leu Leu
                    355                 360                 365

Glu Glu Gly Ser Phe His Pro Leu Gly Met Ser Gly Ala Gly Ser
        370                 375                 380

<210> SEQ ID NO 26
<211> LENGTH: 2074
<212> TYPE: DNA
<213> ORGANISM: homo sapiens

<400> SEQUENCE: 26
```

| | | | |
|---|---|---|---|
| atcagcccac caggagacct cgcccgccgc tcccccgggc tccccggcca tgtctcccgc | | | 60 |
| ccggctccgg ccccgactgc acttctgcct ggtcctgttg ctgctgctgg tggtgccggc | | | 120 |
| ggcatggggc tgcgggccgg gtcgggtggt gggcagccgc cggcgaccgc cacgcaaact | | | 180 |
| cgtgccgctc gcctacaagc agttcagccc caatgtgccc gagaagaccc tgggcgccag | | | 240 |
| cggacgctat gaaggcaaga tcgctcgcag ctccgagcgc ttcaaggagc tcaccccaa | | | 300 |
| ttacaatcca gacatcatct tcaaggacga ggagaacaca ggcgccgacc gcctcatgac | | | 360 |
| ccagcgctgc aaggaccgcc tgaactcgct ggctatctcg gtgatgaacc agtggcccgg | | | 420 |
| tgtgaagctg cgggtgaccg agggctggga cgaggacggc caccactcag aggagtccct | | | 480 |
| gcattatgag ggccgcgcgg tggacatcac cacatcagac cgcgaccgca taagtatgg | | | 540 |
| actgctggcg cgcttggcag tggaggccgg ctttgactgg gtgtattacg agtcaaaggc | | | 600 |
| ccacgtgcat tgctccgtca gtccgagca ctcggccgca gccaagacgg cggctgctt | | | 660 |
| ccctgccgga gcccaggtac gcctggagag tggggcgcgt gtggccttgt cagccgtgag | | | 720 |
| gccgggagac cgtgtgctgg ccatggggga ggatgggagc cccaccttca gcgatgtgct | | | 780 |
| cattttcctg gaccgcgagc ctcacaggct gagagcctc caggtcatcg agactcagga | | | 840 |
| cccccacgc cgcctggcac tcacacccgc tcacctgctc tttacggctg acaatcacac | | | 900 |
| ggagccggca gcccgcttcc gggccacatt tgccagccac gtgcagcctg ccagtacgt | | | 960 |
| gctggtggct ggggtgccag gcctgcagcc tgccgcgtg gcagctgtct ctacacacgt | | | 1020 |
| ggccctcggg gcctacgccc cgctcacaaa gcatgggaca ctggtggtgg aggatgtggt | | | 1080 |
| ggcatcctgc ttcgcggccg tggctgacca ccacctggct cagttggcct tctgccccct | | | 1140 |
| gagactcttt cacagcttgg catggggcag ctggaccccg ggggagggtg tgcattggta | | | 1200 |
| cccccagctg ctctaccgcc tggggcgtct cctgctagaa gagggcagct tccacccact | | | 1260 |
| gggcatgtcc ggggcaggga gctgaaagga ctccaccgct gccctcctgg aactgctgta | | | 1320 |
| ctgggtccag aagcctctca gccaggaggg agctggccct ggaagggacc tgagctgggg | | | 1380 |
| gacactggct cctgccatct cctctgccat gaagatacac cattgagact tgactgggca | | | 1440 |
| acaccagcgt cccccacccc cgtcgtggtg tagtcataga gctgcaagct gagctggcga | | | 1500 |
| ggggatggtt gttgaccct ctctcctaga gaccttgagg ctggcacggc gactcccaac | | | 1560 |
| tcagcctgct ctcactacga gttttcatac tctgcctccc ccattgggga gggcccattc | | | 1620 |
| catccatctt aggcccctt gggtgggctt gcgcctcagt tgatgctgct aaattccctg | | | 1680 |
| ggagccagca tggatctggc tggacccgat gctgtccaga actgggaagg ccacaggggt | | | 1740 |
| ggggcagcca tccggccat tctgaggtat gacattcctc cccggccaca ctcctcaaga | | | 1800 |
| cacatccaga gactgttgct gtctgtgggc agagttctgt gttctggcca atgtgaccgt | | | 1860 |

```
agtgccgggg actgggggag gtgggttgga tgtgcttgcc accccccgg ctaagctccc      1920 ccttctgctg aaccatgatc cccaccccct ccgccggtca gtctcccata ccttatttat      1980
tggagtggag ggggaagccc atgggagaat tttggggatg ttttggtctt ttcttccttt      2040
tgtaataaaa attatttaag ttgttagagc caaa                                  2074

<210> SEQ ID NO 27
<211> LENGTH: 730
<212> TYPE: PRT
<213> ORGANISM: homo sapiens

<400> SEQUENCE: 27

Met Pro Gly Val Ala Arg Leu Pro Leu Leu Gly Leu Leu Leu Leu
1               5                   10                  15

Pro Arg Pro Gly Arg Pro Leu Asp Leu Ala Asp Tyr Thr Tyr Asp Leu
                20                  25                  30

Ala Glu Glu Asp Asp Ser Glu Pro Leu Asn Tyr Lys Asp Pro Cys Lys
            35                  40                  45

Ala Ala Ala Phe Leu Gly Asp Ile Ala Leu Asp Glu Glu Asp Leu Arg
        50                  55                  60

Ala Phe Gln Val Gln Gln Ala Val Asp Leu Arg Arg His Thr Ala Arg
65                  70                  75                  80

Lys Ser Ser Ile Lys Ala Ala Val Pro Gly Asn Thr Ser Thr Pro Ser
                85                  90                  95

Cys Gln Ser Thr Asn Gly Gln Pro Gln Arg Gly Ala Cys Gly Arg Trp
            100                 105                 110

Arg Gly Arg Ser Arg Ser Arg Arg Ala Ala Thr Ser Arg Pro Glu Arg
        115                 120                 125

Val Trp Pro Asp Gly Val Ile Pro Phe Val Ile Gly Gly Asn Phe Thr
130                 135                 140

Gly Ser Gln Arg Ala Val Phe Arg Gln Ala Met Arg His Trp Glu Lys
145                 150                 155                 160

His Thr Cys Val Thr Phe Leu Glu Arg Thr Asp Glu Asp Ser Tyr Ile
                165                 170                 175

Val Phe Thr Tyr Arg Pro Cys Gly Cys Cys Ser Tyr Val Gly Arg Arg
            180                 185                 190

Gly Gly Gly Pro Gln Ala Ile Ser Ile Gly Lys Asn Cys Asp Lys Phe
        195                 200                 205

Gly Ile Val Val His Glu Leu Gly His Val Val Gly Phe Trp His Glu
    210                 215                 220

His Thr Arg Pro Asp Arg Asp Arg His Val Ser Ile Val Arg Glu Asn
225                 230                 235                 240

Ile Gln Pro Gly Gln Glu Tyr Asn Phe Leu Lys Met Glu Pro Gln Glu
                245                 250                 255

Val Glu Ser Leu Gly Glu Thr Tyr Asp Phe Asp Ser Ile Met His Tyr
            260                 265                 270

Ala Arg Asn Thr Phe Ser Arg Gly Ile Phe Leu Asp Thr Ile Val Pro
        275                 280                 285

Lys Tyr Glu Val Asn Gly Val Lys Pro Pro Ile Gly Gln Arg Thr Arg
    290                 295                 300

Leu Ser Lys Gly Asp Ile Ala Gln Ala Arg Lys Leu Tyr Lys Cys Pro
305                 310                 315                 320

Ala Cys Gly Glu Thr Leu Gln Asp Ser Thr Gly Asn Phe Ser Ser Pro
                325                 330                 335
```

Glu Tyr Pro Asn Gly Tyr Ser Ala His Met His Cys Val Trp Arg Ile
                340                 345                 350

Ser Val Thr Pro Gly Glu Lys Ile Ile Leu Asn Phe Thr Ser Leu Asp
            355                 360                 365

Leu Tyr Arg Ser Arg Leu Cys Trp Tyr Asp Tyr Val Glu Val Arg Asp
        370                 375                 380

Gly Phe Trp Arg Lys Ala Pro Leu Arg Gly Arg Phe Cys Gly Ser Lys
385                 390                 395                 400

Leu Pro Glu Pro Ile Val Ser Thr Asp Ser Arg Leu Trp Val Glu Phe
                405                 410                 415

Arg Ser Ser Asn Trp Val Gly Lys Gly Phe Phe Ala Val Tyr Glu
            420                 425                 430

Ala Ile Cys Gly Gly Asp Val Lys Lys Asp Tyr Gly His Ile Gln Ser
        435                 440                 445

Pro Asn Tyr Pro Asp Asp Tyr Arg Pro Ser Lys Val Cys Ile Trp Arg
    450                 455                 460

Ile Gln Val Ser Glu Gly Phe His Val Gly Leu Thr Phe Gln Ser Phe
465                 470                 475                 480

Glu Ile Glu Arg His Asp Ser Cys Ala Tyr Asp Tyr Leu Glu Val Arg
                485                 490                 495

Asp Gly His Ser Glu Ser Ser Thr Leu Ile Gly Arg Tyr Cys Gly Tyr
            500                 505                 510

Glu Lys Pro Asp Asp Ile Lys Ser Thr Ser Ser Arg Leu Trp Leu Lys
        515                 520                 525

Phe Val Ser Asp Gly Ser Ile Asn Lys Ala Gly Phe Ala Val Asn Phe
530                 535                 540

Phe Lys Glu Val Asp Glu Cys Ser Arg Pro Asn Arg Gly Gly Cys Glu
545                 550                 555                 560

Gln Arg Cys Leu Asn Thr Leu Gly Ser Tyr Lys Cys Ser Cys Asp Pro
                565                 570                 575

Gly Tyr Glu Leu Ala Pro Asp Lys Arg Arg Cys Glu Ala Ala Cys Gly
            580                 585                 590

Gly Phe Leu Thr Lys Leu Asn Gly Ser Ile Thr Ser Pro Gly Trp Pro
        595                 600                 605

Lys Glu Tyr Pro Pro Asn Lys Asn Cys Ile Trp Gln Leu Val Ala Pro
    610                 615                 620

Thr Gln Tyr Arg Ile Ser Leu Gln Phe Asp Phe Glu Thr Glu Gly
625                 630                 635                 640

Asn Asp Val Cys Lys Tyr Asp Phe Val Glu Val Arg Ser Gly Leu Thr
                645                 650                 655

Ala Asp Ser Lys Leu His Gly Lys Phe Cys Gly Ser Glu Lys Pro Glu
            660                 665                 670

Val Ile Thr Ser Gln Tyr Asn Asn Met Arg Val Glu Phe Lys Ser Asp
        675                 680                 685

Asn Thr Val Ser Lys Lys Gly Phe Lys Ala His Phe Phe Ser Glu Lys
    690                 695                 700

Arg Pro Ala Leu Gln Pro Pro Arg Gly Arg Pro His Gln Leu Lys Phe
705                 710                 715                 720

Arg Val Gln Lys Arg Asn Arg Thr Pro Gln
                725                 730

<210> SEQ ID NO 28
<211> LENGTH: 708
<212> TYPE: PRT

<213> ORGANISM: homo sapiens

<400> SEQUENCE: 28

```
Leu Asp Leu Ala Asp Tyr Thr Tyr Asp Leu Ala Glu Glu Asp Asp Ser
1               5                   10                  15

Glu Pro Leu Asn Tyr Lys Asp Pro Cys Lys Ala Ala Phe Leu Gly
            20                  25                  30

Asp Ile Ala Leu Asp Glu Glu Asp Leu Arg Ala Phe Gln Val Gln Gln
        35                  40                  45

Ala Val Asp Leu Arg Arg His Thr Ala Arg Lys Ser Ser Ile Lys Ala
    50                  55                  60

Ala Val Pro Gly Asn Thr Ser Thr Pro Ser Cys Gln Ser Thr Asn Gly
65                  70                  75                  80

Gln Pro Gln Arg Gly Ala Cys Gly Arg Trp Arg Gly Arg Ser Arg Ser
                85                  90                  95

Arg Arg Ala Ala Thr Ser Arg Pro Glu Arg Val Trp Pro Asp Gly Val
                100                 105                 110

Ile Pro Phe Val Ile Gly Gly Asn Phe Thr Gly Ser Gln Arg Ala Val
            115                 120                 125

Phe Arg Gln Ala Met Arg His Trp Glu Lys His Thr Cys Val Thr Phe
130                 135                 140

Leu Glu Arg Thr Asp Glu Asp Ser Tyr Ile Val Phe Thr Tyr Arg Pro
145                 150                 155                 160

Cys Gly Cys Cys Ser Tyr Val Gly Arg Arg Gly Gly Pro Gln Ala
                165                 170                 175

Ile Ser Ile Gly Lys Asn Cys Asp Lys Phe Gly Ile Val Val His Glu
            180                 185                 190

Leu Gly His Val Val Gly Phe Trp His Glu His Thr Arg Pro Asp Arg
            195                 200                 205

Asp Arg His Val Ser Ile Val Arg Glu Asn Ile Gln Pro Gly Gln Glu
210                 215                 220

Tyr Asn Phe Leu Lys Met Glu Pro Gln Glu Val Glu Ser Leu Gly Glu
225                 230                 235                 240

Thr Tyr Asp Phe Asp Ser Ile Met His Tyr Ala Arg Asn Thr Phe Ser
                245                 250                 255

Arg Gly Ile Phe Leu Asp Thr Ile Val Pro Lys Tyr Glu Val Asn Gly
            260                 265                 270

Val Lys Pro Pro Ile Gly Gln Arg Thr Arg Leu Ser Lys Gly Asp Ile
            275                 280                 285

Ala Gln Ala Arg Lys Leu Tyr Lys Cys Pro Ala Cys Gly Glu Thr Leu
290                 295                 300

Gln Asp Ser Thr Gly Asn Phe Ser Ser Pro Glu Tyr Pro Asn Gly Tyr
305                 310                 315                 320

Ser Ala His Met His Cys Val Trp Arg Ile Ser Val Thr Pro Gly Glu
                325                 330                 335

Lys Ile Ile Leu Asn Phe Thr Ser Leu Asp Leu Tyr Arg Ser Arg Leu
            340                 345                 350

Cys Trp Tyr Asp Tyr Val Glu Val Arg Asp Gly Phe Trp Arg Lys Ala
            355                 360                 365

Pro Leu Arg Gly Arg Phe Cys Gly Ser Lys Leu Pro Glu Pro Ile Val
370                 375                 380

Ser Thr Asp Ser Arg Leu Trp Val Glu Phe Arg Ser Ser Asn Trp
385                 390                 395                 400
```

Val Gly Lys Gly Phe Ala Val Tyr Glu Ala Ile Cys Gly Gly Asp
            405                 410                 415

Val Lys Lys Asp Tyr Gly His Ile Gln Ser Pro Asn Tyr Pro Asp Asp
        420                 425                 430

Tyr Arg Pro Ser Lys Val Cys Ile Trp Arg Ile Gln Val Ser Glu Gly
            435                 440                 445

Phe His Val Gly Leu Thr Phe Gln Ser Phe Glu Ile Glu Arg His Asp
        450                 455                 460

Ser Cys Ala Tyr Asp Tyr Leu Glu Val Arg Asp Gly His Ser Glu Ser
465                 470                 475                 480

Ser Thr Leu Ile Gly Arg Tyr Cys Gly Tyr Glu Lys Pro Asp Asp Ile
            485                 490                 495

Lys Ser Thr Ser Ser Arg Leu Trp Leu Lys Phe Val Ser Asp Gly Ser
            500                 505                 510

Ile Asn Lys Ala Gly Phe Ala Val Asn Phe Phe Lys Glu Val Asp Glu
        515                 520                 525

Cys Ser Arg Pro Asn Arg Gly Gly Cys Glu Gln Arg Cys Leu Asn Thr
530                 535                 540

Leu Gly Ser Tyr Lys Cys Ser Cys Asp Pro Gly Tyr Glu Leu Ala Pro
545                 550                 555                 560

Asp Lys Arg Arg Cys Glu Ala Ala Cys Gly Gly Phe Leu Thr Lys Leu
            565                 570                 575

Asn Gly Ser Ile Thr Ser Pro Gly Trp Pro Lys Glu Tyr Pro Pro Asn
            580                 585                 590

Lys Asn Cys Ile Trp Gln Leu Val Ala Pro Thr Gln Tyr Arg Ile Ser
        595                 600                 605

Leu Gln Phe Asp Phe Phe Glu Thr Glu Gly Asn Asp Val Cys Lys Tyr
610                 615                 620

Asp Phe Val Glu Val Arg Ser Gly Leu Thr Ala Asp Ser Lys Leu His
625                 630                 635                 640

Gly Lys Phe Cys Gly Ser Glu Lys Pro Glu Val Ile Thr Ser Gln Tyr
            645                 650                 655

Asn Asn Met Arg Val Glu Phe Lys Ser Asp Asn Thr Val Ser Lys Lys
        660                 665                 670

Gly Phe Lys Ala His Phe Phe Ser Glu Lys Arg Pro Ala Leu Gln Pro
        675                 680                 685

Pro Arg Gly Arg Pro His Gln Leu Lys Phe Arg Val Gln Lys Arg Asn
        690                 695                 700

Arg Thr Pro Gln
705

<210> SEQ ID NO 29
<211> LENGTH: 2747
<212> TYPE: DNA
<213> ORGANISM: homo sapiens

<400> SEQUENCE: 29
gtcggaggga gggagggagg gagagaaaga aagagagaaa aagaaggaaa gggagaggga    60
gacggctgga gcccgaggac gagcgcggag ccgcggaccg agcggggggc gggagacagg   120
aaggagggag gcgagcagag ggaagggaa gaggtcgggg agcgagggcg ggagcggtcg    180
cggtcgcgat cgagcaagca agcgggcgag aggacgccct ccctggcct ccagtgcgcc    240 gcttccctcg ccgccgcccc gccagcatgc cggcgtggc ccgcctgccg ctgctgctcg    300
ggctgctgct gctcccgcgt cccggccggc cgctggactt ggccgactac acctatgacc   360

```
tggcggagga ggacgactcg gagcccctca actacaaaga cccctgcaag gcggctgcct      420
ttcttgggga cattgccctg gacgaagagg acctgagggc cttccaggta cagcaggctg      480
tggatctcag acggcacaca gctcgtaagt cctccatcaa agctgcagtt ccaggaaaca      540
cttctacccc cagctgccag agcaccaacg ggcagcctca gaggggagcc tgtgggagat      600
ggagaggtag atcccgtagc cggcgggcgg cgacgtcccg accagagcgt gtgtggcccg      660
atggggtcat ccccttttgtc attggggggaa acttcactgg tagccagagg gcagtcttcc    720
ggcaggccat gaggcactgg gagaagcaca cctgtgtcac cttcctggag cgcactgacg      780
aggacagcta tattgtgttc acctatcgac cttgcgggtg ctgctcctac gtgggtcgcc      840
gcggcggggg cccccaggcc atctccatcg gcaagaactg tgacaagttc ggcattgtgg      900
tccacgagct gggccacgtc gtcggcttct ggcacgaaca cactcggcca gaccgggacc      960
gccacgtttc catcgttcgt gagaacatcc agccagggca ggagtataac ttcctgaaga     1020
tggagcctca ggaggtggag tccctggggg agacctatga cttcgacagc atcatgcatt     1080
acgctcggaa cacattctcc aggggcatct tcctggatac cattgtcccc aagtatgagg     1140
tgaacggggt gaaacctccc attggccaaa ggacacggct cagcaagggg gacattgccc     1200
aagcccgcaa gctttacaag tgcccagcct gtggagagac cctgcaagac agcacaggca     1260
acttctcctc ccctgaatac cccaatggct actctgctca catgcactgc gtgtggcgca     1320
tctctgtcac acccggggag aagatcatcc tgaacttcac gtccctggac ctgtaccgca     1380
gccgcctgtg ctggtacgac tatgtggagg tccgagatgg cttctggagg aaggcgcccc     1440
tccgaggccg cttctgcggg tccaaactcc ctgagcctat cgtctccact gacagccgcc     1500
tctgggttga attccgcagc agcagcaatt gggttggaaa gggcttcttt gcagtctacg     1560
aagccatctg cggggggtgat gtgaaaaagg actatggcca cattcaatcg cccaactacc     1620
cagacgatta ccggcccagc aaagtctgca tctggcggat ccaggtgtct gagggcttcc     1680
acgtgggcct cacattccag tcctttgaga ttgagcgcca cgacagctgt gcctacgact     1740
atctggaggt gcgcgacggg cacagtgaga gcagcaccct catcgggcgc tactgtggct     1800
atgagaagcc tgatgacatc aagagcacgt ccagccgcct ctggctcaag ttcgtctctg     1860
acgggtccat taacaaagcg ggctttgccg tcaactttttt caaagaggtg gacgagtgct     1920
ctcggcccaa ccgcggggggc tgtgagcagc ggtgcctcaa cccctgggc agctacaagt     1980 gcagctgtga ccccgggtac gagctggccc cagacaagcg ccgctgtgag gctgcttgtg     2040
gcggattcct caccaagctc aacgctccca tcaccagccc gggctggccc aaggagtacc     2100
cccccaacaa gaactgcatc tggcagctgg tggccccccac ccagtaccgc atctccctgc     2160
agtttgactt ctttgagaca gagggcaatg atgtgtgcaa gtacgacttc gtggaggtgc     2220
gcagtggact cacagctgac tccaagctgc atggcaagtt ctgtggttct gagaagcccg     2280
aggtcatcac ctcccagtac aacaacatgc gcgtggagtt caagtccgac aacaccgtgt     2340
ccaaaaaggg cttcaaggcc cacttcttct cagaaaagag gccagctctg cagcccctc      2400 ggggacgccc ccaccagctc aaattccgag tgcagaaaag aaaccggacc ccccagtgag     2460
gcctgccagg cctcccggac cccttgttac tcaggaacct caccttggac ggaatgggat     2520
gggggcttcg gtgcccacca acccccacc tccactctgc cattccggcc cacctccctc     2580
tggccggaca gaactggtgc tctcttctcc ccactgtgcc cgtccgcgga ccggggaccc     2640
ttccccgtgc cctaccccct cccatttttga tggtgtctgt gacatttcct gttgtgaagt     2700
```
aaaagaggga cccctgcgtc ctgctccttt ctcttgcaga aaaaaaa          2747

<210> SEQ ID NO 30
<211> LENGTH: 126
<212> TYPE: PRT
<213> ORGANISM: homo sapiens

<400> SEQUENCE: 30

Met His Leu Ser Gln Leu Leu Ala Cys Ala Leu Leu Thr Leu Leu
1               5                   10                  15

Ser Leu Arg Pro Ser Glu Ala Lys Pro Gly Ala Pro Lys Val Pro
                20                  25                  30

Arg Thr Pro Pro Ala Glu Glu Leu Ala Glu Pro Gln Ala Ala Gly
                35                  40                  45

Gly Gln Lys Lys Gly Asp Lys Ala Pro Gly Gly Gly Ala Asn Leu
        50                  55                  60

Lys Gly Asp Arg Ser Arg Leu Leu Arg Asp Leu Arg Val Asp Thr Lys
65                  70                  75                  80

Ser Arg Ala Ala Trp Ala Arg Leu Leu Gln Glu His Pro Asn Ala Arg
                85                  90                  95

Lys Tyr Lys Gly Ala Asn Lys Lys Gly Leu Ser Lys Gly Cys Phe Gly
            100                 105                 110

Leu Lys Leu Asp Arg Ile Gly Ser Met Ser Gly Leu Gly Cys
            115                 120                 125

<210> SEQ ID NO 31
<211> LENGTH: 53
<212> TYPE: PRT
<213> ORGANISM: homo sapiens

<400> SEQUENCE: 31

Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Lys Lys Gly
                20                  25                  30

Leu Ser Lys Gly Cys Phe Gly Leu Lys Leu Asp Arg Ile Gly Ser Met
            35                  40                  45

Ser Gly Leu Gly Cys
        50

<210> SEQ ID NO 32
<211> LENGTH: 29
<212> TYPE: PRT
<213> ORGANISM: homo sapiens

<400> SEQUENCE: 32

Tyr Lys Gly Ala Asn Lys Lys Gly Leu Ser Lys Gly Cys Phe Gly Leu
1               5                   10                  15

Lys Leu Asp Arg Ile Gly Ser Met Ser Gly Leu Gly Cys
            20                  25

<210> SEQ ID NO 33
<211> LENGTH: 22
<212> TYPE: PRT
<213> ORGANISM: homo sapiens

<400> SEQUENCE: 33

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 34
<211> LENGTH: 701
<212> TYPE: DNA
<213> ORGANISM: homo sapiens

<400> SEQUENCE: 34

```
cgcatccccc tgctggtctg cccgccgacc tgcgcgccct cgctgccgcc cgtgtgcgcc      60
cctcgacccc agcggcacca tgcatctctc ccagctgctg gcctgcgccc tgctgctcac     120
gctgctctcc ctccggccct ccgaagccaa gcccggggcg ccgccgaagg tcccgcgaac     180
cccgccggca gaggagctgg ccgagccgca ggctgcgggc ggcggtcaga agaagggcga     240
caaggctccc gggggcgggg cgccaatctc aagggcgac cggtcgcgac tgctccggga     300
cctgcgcgtg gacaccaagt cgcgggcagc gtgggctcgc cttctgcaag agcaccccaa     360
cgcgcgcaaa tacaaggag ccaacaagaa gggcttgtcc aagggctgct cggcctcaa      420
gctggaccga atcggctcca tgagcggcct gggatgttag tgcggcgccc cctggcggcg     480
gatcgggaac tggctccgtt gtgctgaggt catctttggt catcagcctc cagcatctgg     540
aaacacctcc aacgcaatgt ggcttttaca tttctttctt tctttctttt ttttcctgg     600
tactgggaat acacaacacc agctgtttta ttattatttg gggaggggt tgtgattta      660
ttatttgttt ttttaaaatg aaaaataaaa agttatatat t                         701
```

<210> SEQ ID NO 35
<211> LENGTH: 370
<212> TYPE: PRT
<213> ORGANISM: homo sapiens

<400> SEQUENCE: 35

Met Gly Leu Trp Ala Leu Leu Pro Gly Trp Val Ser Ala Thr Leu Leu
1               5                   10                  15

Leu Ala Leu Ala Ala Leu Pro Ala Ala Leu Ala Ala Asn Ser Ser Gly
            20                  25                  30

Arg Trp Trp Gly Ile Val Asn Val Ala Ser Ser Thr Asn Leu Leu Thr
        35                  40                  45

Asp Ser Lys Ser Leu Gln Leu Val Leu Glu Pro Ser Leu Gln Leu Leu
    50                  55                  60

Ser Arg Lys Gln Arg Arg Leu Ile Arg Gln Asn Pro Gly Ile Leu His
65                  70                  75                  80

Ser Val Ser Gly Gly Leu Gln Ser Ala Val Arg Glu Cys Lys Trp Gln
                85                  90                  95

Phe Arg Asn Arg Arg Trp Asn Cys Pro Thr Ala Pro Gly Pro His Leu
            100                 105                 110

Phe Gly Lys Ile Val Asn Arg Gly Cys Arg Glu Thr Ala Phe Ile Phe
        115                 120                 125

Ala Ile Thr Ser Ala Gly Val Thr His Ser Val Ala Arg Ser Cys Ser
    130                 135                 140

Glu Gly Ser Ile Glu Ser Cys Thr Cys Asp Tyr Arg Arg Arg Gly Pro
145                 150                 155                 160

Gly Gly Pro Asp Trp His Trp Gly Gly Cys Ser Asp Asn Ile Asp Phe
                165                 170                 175

Gly Arg Leu Phe Gly Arg Glu Phe Val Asp Ser Gly Glu Lys Gly Arg
            180                 185                 190

```
Asp Leu Arg Phe Leu Met Asn Leu His Asn Asn Glu Ala Gly Arg Thr
            195                 200                 205

Thr Val Phe Ser Glu Met Arg Gln Glu Cys Lys Cys His Gly Met Ser
        210                 215                 220

Gly Ser Cys Thr Val Arg Thr Cys Trp Met Arg Leu Pro Thr Leu Arg
225                 230                 235                 240

Ala Val Gly Asp Val Leu Arg Asp Arg Phe Asp Gly Ala Ser Arg Val
                245                 250                 255

Leu Tyr Gly Asn Arg Gly Ser Asn Arg Ala Ser Arg Ala Glu Leu Leu
            260                 265                 270

Arg Leu Glu Pro Glu Asp Pro Ala His Lys Pro Pro Ser Pro His Asp
        275                 280                 285

Leu Val Tyr Phe Glu Lys Ser Pro Asn Phe Cys Thr Tyr Ser Gly Arg
        290                 295                 300

Leu Gly Thr Ala Gly Thr Ala Gly Arg Ala Cys Asn Ser Ser Ser Pro
305                 310                 315                 320

Ala Leu Asp Gly Cys Glu Leu Leu Cys Cys Gly Arg Gly His Arg Thr
                325                 330                 335

Arg Thr Gln Arg Val Thr Glu Arg Cys Asn Cys Thr Phe His Trp Cys
            340                 345                 350

Cys His Val Ser Cys Arg Asn Cys Thr His Thr Arg Val Leu His Glu
        355                 360                 365

Cys Leu
    370

<210> SEQ ID NO 36
<211> LENGTH: 343
<212> TYPE: PRT
<213> ORGANISM: homo sapiens

<400> SEQUENCE: 36

Ala Asn Ser Ser Gly Arg Trp Trp Gly Ile Val Asn Val Ala Ser Ser
1               5                   10                  15

Thr Asn Leu Leu Thr Asp Ser Lys Ser Leu Gln Leu Val Leu Glu Pro
            20                  25                  30

Ser Leu Gln Leu Leu Ser Arg Lys Gln Arg Leu Ile Arg Gln Asn
        35                  40                  45

Pro Gly Ile Leu His Ser Val Ser Gly Gly Leu Gln Ser Ala Val Arg
            50                  55                  60

Glu Cys Lys Trp Gln Phe Arg Asn Arg Arg Trp Asn Cys Pro Thr Ala
65                  70                  75                  80

Pro Gly Pro His Leu Phe Gly Lys Ile Val Asn Arg Gly Cys Arg Glu
                85                  90                  95

Thr Ala Phe Ile Phe Ala Ile Thr Ser Ala Gly Val Thr His Ser Val
            100                 105                 110

Ala Arg Ser Cys Ser Glu Gly Ser Ile Glu Ser Cys Thr Cys Asp Tyr
        115                 120                 125

Arg Arg Arg Gly Pro Gly Gly Pro Asp Trp His Trp Gly Gly Cys Ser
    130                 135                 140

Asp Asn Ile Asp Phe Gly Arg Leu Phe Gly Arg Glu Phe Val Asp Ser
145                 150                 155                 160

Gly Glu Lys Gly Arg Asp Leu Arg Phe Leu Met Asn Leu His Asn Asn
                165                 170                 175

Glu Ala Gly Arg Thr Thr Val Phe Ser Glu Met Arg Gln Glu Cys Lys
            180                 185                 190
```

```
Cys His Gly Met Ser Gly Ser Cys Thr Val Arg Thr Cys Trp Met Arg
        195                 200                 205

Leu Pro Thr Leu Arg Ala Val Gly Asp Val Leu Arg Asp Arg Phe Asp
    210                 215                 220

Gly Ala Ser Arg Val Leu Tyr Gly Asn Arg Gly Ser Asn Arg Ala Ser
225                 230                 235                 240

Arg Ala Glu Leu Leu Arg Leu Glu Pro Glu Asp Pro Ala His Lys Pro
                245                 250                 255

Pro Ser Pro His Asp Leu Val Tyr Phe Glu Lys Ser Pro Asn Phe Cys
                260                 265                 270

Thr Tyr Ser Gly Arg Leu Gly Thr Ala Gly Thr Ala Gly Arg Ala Cys
            275                 280                 285

Asn Ser Ser Ser Pro Ala Leu Asp Gly Cys Glu Leu Leu Cys Cys Gly
        290                 295                 300

Arg Gly His Arg Thr Arg Thr Gln Arg Val Thr Glu Arg Cys Asn Cys
305                 310                 315                 320

Thr Phe His Trp Cys Cys His Val Ser Cys Arg Asn Cys Thr His Thr
                325                 330                 335

Arg Val Leu His Glu Cys Leu
            340
```

```
<210> SEQ ID NO 37
<211> LENGTH: 2284
<212> TYPE: DNA
<213> ORGANISM: homo sapiens

<400> SEQUENCE: 37
```

| | | | | |
|---|---|---|---|---|
| gcggtgccgc | cgccgtggc | cgcctcagcc | caccagccgg | gaccgcgagc catgctgtcc | 60 |
| gccgcccgcc | cccagggttg | ttaaagccag | actgcgaact | ctcgccactg ccgccaccgc | 120 |
| cgcgtcccgt | cccaccgtcg | cgggcaacaa | ccaaagtcgc | cgcaactgca gcacagagcg | 180 |
| ggcaaagcca | ggcaggccat | ggggctctgg | gcgctgttgc | ctggctgggt ttctgctacg | 240 |
| ctgctgctgg | cgctggccgc | tctgcccgca | gccctggctg | ccaacagcag tggccgatgg | 300 |
| tggggtattg | tgaacgtagc | ctcctccacg | aacctgctta | cagactccaa gagtctgcaa | 360 |
| ctggtactcg | agcccagtct | gcagctgttg | agccgcaaac | agcggcgtct gatacgccaa | 420 |
| aatccgggga | tcctgcacag | cgtgagtggg | gggctgcaga | gtgccgtgcg cgagtgcaag | 480 |
| tggcagttcc | ggaatcgccc | ctggaactgt | cccactgctc | cagggcccca cctcttcggc | 540 |
| aagatcgtca | ccgaggctg | tcgagaaacg | gcgtttatct | tcgctatcac ctccgccggg | 600 |
| gtcacccatt | cggtggcgcg | ctcctgctca | gaaggttcca | tcgaatcctg cacgtgtgac | 660 |
| taccggcggc | gcgccccggg | ggccccgac | tggcactggg | ggctgcag cgacaacatt | 720 |
| gacttcggcc | gcctcttcgg | ccgggagttc | gtggactccg | gggagaaggg gcgggacctg | 780 |
| cgcttcctca | tgaaccttca | aacaacgag | gcaggccgta | cgaccgtatt ctccgagatg | 840 |
| cgccaggagt | gcaagtgcca | cgggatgtcc | ggctcatgca | cggtgcgcac gtgctggatg | 900 |
| cggctgccca | cgctgcgcgc | cgtgggcgat | gtgctgcgcg | accgcttcga cggcgcctcg | 960 |
| cgcgtcctgt | acggcaaccg | cggcagcaac | cgcgcttcgc | gggcggagct gctgcgcctg | 1020 |
| gagccggaag | accggcccca | caaaccgccc | tcccccacg | acctcgtcta cttcgagaaa | 1080 |
| tcgcccaact | tctgcacgta | cagcggacgc | ctgggcacag | caggcacggc agggcgcgcc | 1140 |
| tgtaacagct | cgtcgcccgc | gctggacggc | tgcgagctgc | tctgctgcgg cagggccac | 1200 |

```
cgcacgcgca cgcagcgcgt caccgagcgc tgcaactgca ccttccactg gtgctgccac   1260
gtcagctgcc gcaactgcac gcacacgcgc gtactgcacg agtgtctgtg aggcgctgcg   1320
cggactcgcc cccaggaacg ctctcctcga gccctccccc aaacagactc gctagcactc   1380
aagacccggt tattcgccca cccgagtacc tccagtcaca ctcccgcggg ttcatacgca   1440
tcccatctct cccacttcct cctacctggg gactcctcaa accacttgcc tggggcggca   1500
tgaaccctct tgccatcctg atggacctgc cccggaccta cctccctccc tctccgcggg   1560
agaccccttg ttgcactgcc ccctgcttgg ccaggaggtg agagaaggat gggtcccctc   1620
cgccatgggg tcggctcctg atggtgtcat tctgcctgct ccatcgcgcc agcgacctct   1680
ctgcctctct tcttcccctt tgtcctgcgt tttctccggg tcctcctaag tcccttccta   1740
ttctcctgcc atgggtgcag accctgaacc cacacctggg catcagggcc tttctcctcc   1800
ccacctgtag ctgaagcagg aggttacagg gcaaagggc agctgtgatg atgtggaaat   1860
gaggttgggg gaaccagcag aaatgccccc attctcccag tctctgtcgt ggagccattg   1920
aacagctgtg agccatgcct ccctgggcca cctcctaccc cttcctgtcc tgcctcctca   1980
tcagtgtgta ataatttgc actgaaacgt ggatacagag ccacgagttt ggatgttgta   2040
aataaaacta tttattgtgc tgggtcccag cctggtttgc aaagaccacc tccaacccaa   2100
cccaatccct ctccactctt ctctcctttc tccctgcagc cttttctggt ccctcttctc   2160

tcctcagttt ctcaaagatg cgtttgcctc ctggaatcag tatttccttc cactgtagct   2220
attagcggct cctcgccccc accagtgtag catcttcctc tgcagaataa aatctctatt   2280
ttta                                                                 2284

<210> SEQ ID NO 38
<211> LENGTH: 5
<212> TYPE: PRT
<213> ORGANISM: Artificial Sequence
<220> FEATURE:
<223> OTHER INFORMATION: peptide linker

<400> SEQUENCE: 38

Gly Gly Gly Gly Ser
1               5

<210> SEQ ID NO 39
<211> LENGTH: 10
<212> TYPE: PRT
<213> ORGANISM: Artificial Sequence
<220> FEATURE:
<223> OTHER INFORMATION: peptide linker

<400> SEQUENCE: 39

Gly Gly Gly Gly Ser Gly Gly Gly Gly Ser
1               5                   10

<210> SEQ ID NO 40
<211> LENGTH: 15
<212> TYPE: PRT
<213> ORGANISM: Artificial Sequence
<220> FEATURE:
<223> OTHER INFORMATION: peptide linker

<400> SEQUENCE: 40

Gly Gly Gly Gly Ser Gly Gly Gly Gly Ser Gly Gly Gly Gly Ser
1               5                   10                  15

<210> SEQ ID NO 41
```

<211> LENGTH: 544
<212> TYPE: PRT
<213> ORGANISM: Artificial Sequence
<220> FEATURE:
<223> OTHER INFORMATION: scFv-Fc-IGF-1 fusion protein

<400> SEQUENCE: 41

```
Ala Gly Pro Glu Thr Leu Cys Gly Ala Glu Leu Val Asp Ala Leu Gln
 1               5                  10                  15
Phe Val Cys Gly Asp Arg Gly Phe Tyr Phe Asn Lys Pro Thr Gly Tyr
                20                  25                  30
Gly Ser Ser Ser Arg Arg Ala Pro Gln Thr Gly Ile Val Asp Glu Cys
            35                  40                  45
Cys Phe Arg Ser Cys Asp Leu Arg Arg Leu Glu Met Tyr Cys Ala Pro
        50                  55                  60
Leu Gly Gly Gly Ser Glu Val Gln Leu Val Gln Ser Gly Ala Glu
 65                  70                  75                  80
Val Lys Lys Pro Gly Ala Ser Val Lys Val Ser Cys Lys Ala Ser Gly
                85                  90                  95
Gly Thr Phe Ser Ser Tyr Ala Ile Ser Trp Val Arg Gln Ala Pro Gly
            100                 105                 110
Gln Gly Leu Glu Trp Met Gly Gly Ile Ile Pro Ile Phe Gly Thr Ala
        115                 120                 125
Asn Tyr Ala Gln Lys Phe Gln Gly Arg Val Thr Ile Thr Ala Asp Lys
130                 135                 140
Ser Thr Ser Thr Ala Tyr Met Glu Leu Ser Ser Leu Arg Ser Glu Asp
145                 150                 155                 160
Thr Ala Val Tyr Tyr Cys Ala Arg Gly Gln Gly Tyr Trp Phe Asp Pro
                165                 170                 175
Trp Gly Gln Gly Thr Leu Val Thr Val Ser Ser Gly Gly Gly Gly Ser
            180                 185                 190
Gly Gly Gly Ala Ser Ser Gly Gly Ser Asp Val Gln Leu Thr Gln
        195                 200                 205
Ser Pro Ser Ser Leu Ser Ala Ser Val Gly Asp Arg Val Thr Ile Thr
210                 215                 220
Cys Gln Ala Ser Gln Asp Ile Ser Asn Tyr Leu Asn Trp Tyr Gln Gln
225                 230                 235                 240
Lys Pro Gly Lys Ala Pro Lys Leu Leu Ile Tyr Asp Ala Ser Asn Leu
                245                 250                 255
Glu Thr Gly Val Pro Ser Arg Phe Ser Gly Ser Gly Ser Gly Thr Asp
            260                 265                 270
Phe Thr Phe Thr Ile Ser Ser Leu Gln Pro Glu Asp Ile Ala Thr Tyr
        275                 280                 285
Tyr Cys Gln Gln Tyr Asp Asn Leu Pro Leu Thr Phe Gly Gly Gly Thr
290                 295                 300
Lys Leu Glu Ile Lys Arg Gly Gln Ala Gly Gln Gly Pro Asp Lys Thr
305                 310                 315                 320
His Thr Cys Pro Pro Cys Pro Ala Pro Glu Leu Leu Gly Gly Pro Ser
                325                 330                 335
Val Phe Leu Phe Pro Pro Lys Pro Lys Asp Thr Leu Met Ile Ser Arg
            340                 345                 350
Thr Pro Glu Val Thr Cys Val Val Val Asp Val Ser His Glu Asp Pro
        355                 360                 365
Glu Val Lys Phe Asn Trp Tyr Val Asp Gly Val Glu Val His Asn Ala
370                 375                 380
```

```
Lys Thr Lys Pro Arg Glu Glu Gln Tyr Asn Ser Thr Tyr Arg Val Val
385                 390                 395                 400

Ser Val Leu Thr Val Leu His Gln Asp Trp Leu Asn Gly Lys Glu Tyr
            405                 410                 415

Lys Cys Lys Val Ser Asn Lys Ala Leu Pro Ala Pro Ile Glu Lys Thr
        420                 425                 430

Ile Ser Lys Ala Lys Gly Gln Pro Arg Glu Pro Gln Val Tyr Thr Leu
    435                 440                 445

Pro Pro Ser Arg Asp Glu Leu Thr Lys Asn Gln Val Ser Leu Thr Cys
450                 455                 460

Leu Val Lys Gly Phe Tyr Pro Ser Asp Ile Ala Val Glu Trp Glu Ser
465                 470                 475                 480

Asn Gly Gln Pro Glu Asn Asn Tyr Lys Thr Thr Pro Pro Val Leu Asp
                485                 490                 495

Ser Asp Gly Ser Phe Phe Leu Tyr Ser Lys Leu Thr Val Asp Lys Ser
            500                 505                 510

Arg Trp Gln Gln Gly Asn Val Phe Ser Cys Ser Val Met His Glu Ala
        515                 520                 525

Leu His Asn His Tyr Thr Gln Lys Ser Leu Ser Leu Ser Pro Gly Lys
    530                 535                 540

<210> SEQ ID NO 42
<211> LENGTH: 547
<212> TYPE: PRT
<213> ORGANISM: Artificial Sequence
<220> FEATURE:
<223> OTHER INFORMATION: scFv-Fc-IGF-1 fusion protein

<400> SEQUENCE: 42

Ala Gly Pro Glu Thr Leu Cys Gly Ala Glu Leu Val Asp Ala Leu Gln
1               5                   10                  15

Phe Val Cys Gly Asp Arg Gly Phe Tyr Phe Asn Lys Pro Thr Gly Tyr
            20                  25                  30

Gly Ser Ser Ser Arg Arg Ala Pro Gln Thr Gly Ile Val Asp Glu Cys
        35                  40                  45

Cys Phe Arg Ser Cys Asp Leu Arg Arg Leu Glu Met Tyr Cys Ala Pro
    50                  55                  60

Leu Gly Gly Gly Ser Gln Val Gln Leu Gln Gln Ser Gly Pro Gly Leu
65                  70                  75                  80

Leu Val Lys Pro Ser Gln Thr Leu Ser Leu Thr Cys Ala Ile Ser Gly
                85                  90                  95

Asp Ser Val Ser Ser Asn Ser Ala Ala Trp Asn Trp Ile Arg Gln Ser
            100                 105                 110

Pro Ser Arg Gly Leu Glu Trp Leu Gly Arg Thr Tyr Tyr Gly Ser Lys
        115                 120                 125

Trp Tyr Asn Asp Tyr Ala Pro Ser Val Lys Ser Arg Ile Ser Ile Asn
    130                 135                 140

Pro Asp Thr Ser Lys Asn Gln Phe Ser Leu Gln Leu Asn Ser Val Thr
145                 150                 155                 160

Pro Glu Asp Thr Ala Val Tyr Tyr Cys Thr Arg Gly Ile Trp Asn Ala
                165                 170                 175

Phe Asp Ile Trp Gly Gln Gly Thr Met Val Thr Val Ser Ser Gly Gly
            180                 185                 190

Gly Gly Ser Gly Gly Gly Ala Ser Gly Gly Gly Ser Ser Ser Glu
        195                 200                 205
```

```
Leu Thr Gln Asp Pro Ala Val Ser Val Ala Leu Gly Gln Thr Val Arg
    210                 215                 220
Ile Thr Cys Gln Gly Asp Ser Leu Arg Ser Tyr Tyr Ala Ser Trp Tyr
225                 230                 235                 240
Gln Gln Lys Pro Gly Gln Ala Pro Leu Leu Val Ile Tyr Asp Arg Asp
                245                 250                 255
Asn Arg Pro Ser Gly Ile Pro Asp Arg Phe Ser Gly Ser Ser Ser Gly
            260                 265                 270
Asn Thr Ala Ser Leu Thr Ile Thr Gly Ala Gln Ala Glu Asp Glu Ala
        275                 280                 285
Asp Tyr Tyr Cys Gln Ser Tyr Asp Thr Ser Leu Ser Trp Val Phe Gly
290                 295                 300
Gly Gly Thr Gln Leu Thr Val Leu Gly Gly Gln Ala Gly Gln Gly Pro
305                 310                 315                 320
Asp Lys Thr His Thr Cys Pro Pro Cys Pro Ala Pro Glu Leu Leu Gly
                325                 330                 335
Gly Pro Ser Val Phe Leu Phe Pro Pro Lys Pro Lys Asp Thr Leu Met
            340                 345                 350
Ile Ser Arg Thr Pro Glu Val Thr Cys Val Val Val Asp Val Ser His
        355                 360                 365
Glu Asp Pro Glu Val Lys Phe Asn Trp Tyr Val Asp Gly Val Glu Val
370                 375                 380
His Asn Ala Lys Thr Lys Pro Arg Glu Glu Gln Tyr Asn Ser Thr Tyr
385                 390                 395                 400
Arg Val Val Ser Val Leu Thr Val Leu His Gln Asp Trp Leu Asn Gly
                405                 410                 415
Lys Glu Tyr Lys Cys Lys Val Ser Asn Lys Ala Leu Pro Ala Pro Ile
            420                 425                 430
Glu Lys Thr Ile Ser Lys Ala Lys Gly Gln Pro Arg Glu Pro Gln Val
        435                 440                 445
Tyr Thr Leu Pro Pro Ser Arg Asp Glu Leu Thr Lys Asn Gln Val Ser
450                 455                 460
Leu Thr Cys Leu Val Lys Gly Phe Tyr Pro Ser Asp Ile Ala Val Glu
465                 470                 475                 480
Trp Glu Ser Asn Gly Gln Pro Glu Asn Asn Tyr Lys Thr Thr Pro Pro
                485                 490                 495
Val Leu Asp Ser Asp Gly Ser Phe Phe Leu Tyr Ser Lys Leu Thr Val
            500                 505                 510
Asp Lys Ser Arg Trp Gln Gln Gly Asn Val Phe Ser Cys Ser Val Met
        515                 520                 525
His Glu Ala Leu His Asn His Tyr Thr Gln Lys Ser Leu Ser Leu Ser
530                 535                 540
Pro Gly Lys
545

<210> SEQ ID NO 43
<211> LENGTH: 549
<212> TYPE: PRT
<213> ORGANISM: Artificial Sequence
<220> FEATURE:
<223> OTHER INFORMATION: scFv-Fc-IGF-1 fusion protein

<400> SEQUENCE: 43

Ala Gly Pro Glu Thr Leu Cys Gly Ala Glu Leu Val Asp Ala Leu Gln
1               5                   10                  15
```

-continued

```
Phe Val Cys Gly Asp Arg Gly Phe Tyr Phe Asn Lys Pro Thr Gly Tyr
            20                  25                  30

Gly Ser Ser Ser Arg Arg Ala Pro Gln Thr Gly Ile Val Asp Glu Cys
        35                  40                  45

Cys Phe Arg Ser Cys Asp Leu Arg Arg Leu Glu Met Tyr Cys Ala Pro
 50                  55                  60

Leu Gly Gly Gly Ser Glu Val Gln Leu Val Gln Ser Gly Ala Glu
 65                  70                  75                  80

Val Lys Lys Pro Gly Ser Ser Val Lys Val Ser Cys Lys Ala Ser Gly
                 85                  90                  95

Gly Thr Phe Ser Ser Tyr Ala Ile Ser Trp Val Arg Gln Ala Pro Gly
            100                 105                 110

Gln Gly Leu Glu Trp Met Gly Arg Ile Ile Pro Ile Leu Gly Ile Ala
        115                 120                 125

Asn Tyr Ala Gln Lys Phe Gln Gly Arg Val Thr Ile Thr Ala Asp Lys
130                 135                 140

Ser Thr Ser Thr Ala Tyr Met Glu Leu Ser Ser Leu Arg Ser Glu Asp
145                 150                 155                 160

Thr Ala Val Tyr Tyr Cys Ala Arg Trp Gly Ser Gly Ser His Ala Phe
                165                 170                 175

Asp Ile Trp Gly Gln Gly Thr Thr Val Thr Val Ser Ser Gly Gly Gly
            180                 185                 190

Gly Ser Gly Gly Gly Ala Ser Ser Gly Gly Ser Ser Tyr Glu Leu
        195                 200                 205

Thr Gln Pro Pro Ser Thr Ser Gly Thr Pro Gly Gln Arg Val Ala Ile
        210                 215                 220

Ser Cys Ser Gly Ala Ser Ser Asn Ile Gly Ser Asn Ala Val Ser Trp
225                 230                 235                 240

Tyr Gln Gln Leu Pro Gly Thr Ala Pro Lys Leu Leu Ile Tyr Ser Asn
                245                 250                 255

Asn Gln Arg Pro Ser Gly Val Pro Asp Arg Phe Ser Gly Ser Lys Ser
            260                 265                 270

Gly Thr Ser Ala Ser Leu Ala Ile Ser Gly Leu Arg Ser Glu Asp Glu
        275                 280                 285

Ala Asp Tyr Tyr Cys Ala Ala Trp Asp Asp Ser Leu Asn Gly Trp Val
        290                 295                 300

Phe Gly Gly Gly Thr Gln Leu Thr Val Leu Gly Gln Ala Gly Gln
305                 310                 315                 320

Gly Pro Asp Lys Thr His Thr Cys Pro Pro Cys Pro Ala Pro Glu Leu
                325                 330                 335

Leu Gly Gly Pro Ser Val Phe Leu Phe Pro Pro Lys Pro Lys Asp Thr
            340                 345                 350

Leu Met Ile Ser Arg Thr Pro Glu Val Thr Cys Val Val Val Asp Val
        355                 360                 365

Ser His Glu Asp Pro Glu Val Lys Phe Asn Trp Tyr Val Asp Gly Val
        370                 375                 380

Glu Val His Asn Ala Lys Thr Lys Pro Arg Glu Glu Gln Tyr Asn Ser
385                 390                 395                 400

Thr Tyr Arg Val Val Ser Val Leu Thr Val Leu His Gln Asp Trp Leu
                405                 410                 415

Asn Gly Lys Glu Tyr Lys Cys Lys Val Ser Asn Lys Ala Leu Pro Ala
            420                 425                 430
```

-continued

```
Pro Ile Glu Lys Thr Ile Ser Lys Ala Lys Gly Gln Pro Arg Glu Pro
            435                 440                 445

Gln Val Tyr Thr Leu Pro Pro Ser Arg Asp Glu Leu Thr Lys Asn Gln
450                 455                 460

Val Ser Leu Thr Cys Leu Val Lys Gly Phe Tyr Pro Ser Asp Ile Ala
465                 470                 475                 480

Val Glu Trp Glu Ser Asn Gly Gln Pro Glu Asn Asn Tyr Lys Thr Thr
                485                 490                 495

Pro Pro Val Leu Asp Ser Asp Gly Ser Phe Phe Leu Tyr Ser Lys Leu
                500                 505                 510

Thr Val Asp Lys Ser Arg Trp Gln Gln Gly Asn Val Phe Ser Cys Ser
            515                 520                 525

Val Met His Glu Ala Leu His Asn His Tyr Thr Gln Lys Ser Leu Ser
530                 535                 540

Leu Ser Pro Gly Lys
545

<210> SEQ ID NO 44
<211> LENGTH: 534
<212> TYPE: PRT
<213> ORGANISM: Artificial Sequence
<220> FEATURE:
<223> OTHER INFORMATION: scFv-Fc-IGF-1 fusion protein

<400> SEQUENCE: 44

Ala Gly Pro Glu Thr Leu Cys Gly Ala Glu Leu Val Asp Ala Leu Gln
1               5                   10                  15

Phe Val Cys Gly Asp Arg Gly Phe Tyr Phe Asn Lys Pro Thr Gly Tyr
                20                  25                  30

Gly Ser Ser Ser Arg Arg Ala Pro Gln Thr Gly Ile Val Asp Glu Cys
            35                  40                  45

Cys Phe Arg Ser Cys Asp Leu Arg Arg Leu Glu Met Tyr Cys Ala Pro
        50                  55                  60

Leu Gly Gly Gly Ser Gly Gln Ala Gly Gln Gly Pro Ala Pro Glu
65                  70                  75                  80

Leu Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
                100                 105                 110

Val Ser His Glu Asp Pro Glu Val Lys Phe Asn Trp Tyr Val Asp Gly
            115                 120                 125

Val Glu Val His Asn Ala Lys Thr Lys Pro Arg Glu Glu Gln Tyr Asn
130                 135                 140

Ser Thr Tyr Arg Val Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
                180                 185                 190

Pro Gln Val Tyr Thr Ser Pro Pro Ser Arg Asp Glu Leu Thr Lys Asn
            195                 200                 205

Gln Val Ser Leu Arg Cys His Val Lys Gly Phe Tyr Pro Ser Asp Ile
        210                 215                 220

Ala Val Glu Trp Glu Ser Asn Gly Gln Pro Glu Asn Asn Tyr Lys Thr
225                 230                 235                 240
```

-continued

```
Thr Lys Pro Val Leu Asp Ser Asp Gly Ser Phe Phe Leu Tyr Ser Lys
                245                 250                 255

Leu Thr Val Asp Lys Ser Arg Trp Gln Gln Gly Asn Val Phe Ser Cys
        260                 265                 270

Ser Val Met His Glu Ala Leu His Asn His Tyr Thr Gln Lys Ser Leu
    275                 280                 285

Ser Leu Ser Pro Gly Lys Glu Val Gln Leu Val Gln Ser Gly Ala Glu
290                 295                 300

Val Lys Lys Pro Gly Ala Ser Val Lys Val Ser Cys Lys Ala Ser Gly
305                 310                 315                 320

Gly Thr Phe Ser Ser Tyr Ala Ile Ser Trp Val Arg Gln Ala Pro Gly
                325                 330                 335

Gln Gly Leu Glu Trp Met Gly Gly Ile Ile Pro Ile Phe Gly Thr Ala
            340                 345                 350

Asn Tyr Ala Gln Lys Phe Gln Gly Arg Val Thr Ile Thr Ala Asp Lys
        355                 360                 365

Ser Thr Ser Thr Ala Tyr Met Glu Leu Ser Ser Leu Arg Ser Glu Asp
    370                 375                 380

Thr Ala Val Tyr Tyr Cys Ala Arg Gly Gln Gly Tyr Trp Phe Asp Pro
385                 390                 395                 400

Trp Gly Gln Gly Thr Leu Val Thr Val Ser Ser Gly Gly Gly Gly Ser
                405                 410                 415

Gly Gly Gly Ala Ser Ser Gly Gly Ser Asp Val Gln Leu Thr Gln
            420                 425                 430

Ser Pro Ser Ser Leu Ser Ala Ser Val Gly Asp Arg Val Thr Ile Thr
        435                 440                 445

Cys Gln Ala Ser Gln Asp Ile Ser Asn Tyr Leu Asn Trp Tyr Gln Gln
    450                 455                 460

Lys Pro Gly Lys Ala Pro Lys Leu Leu Ile Tyr Asp Ala Ser Asn Leu
465                 470                 475                 480

Glu Thr Gly Val Pro Ser Arg Phe Ser Gly Ser Gly Ser Gly Thr Asp
                485                 490                 495

Phe Thr Phe Thr Ile Ser Ser Leu Gln Pro Glu Asp Ile Ala Thr Tyr
            500                 505                 510

Tyr Cys Gln Gln Tyr Asp Asn Leu Pro Leu Thr Phe Gly Gly Gly Thr
        515                 520                 525

Lys Leu Glu Ile Lys Arg
    530
```

<210> SEQ ID NO 45
<211> LENGTH: 537
<212> TYPE: PRT
<213> ORGANISM: Artificial Sequence
<220> FEATURE:
<223> OTHER INFORMATION: scFv-Fc-IGF-1 fusion protein

<400> SEQUENCE: 45

```
Ala Gly Pro Glu Thr Leu Cys Gly Ala Glu Leu Val Asp Ala Leu Gln
1               5                   10                  15

Phe Val Cys Gly Asp Arg Gly Phe Tyr Phe Asn Lys Pro Thr Gly Tyr
            20                  25                  30

Gly Ser Ser Ser Arg Arg Ala Pro Gln Thr Gly Ile Val Asp Glu Cys
        35                  40                  45

Cys Phe Arg Ser Cys Asp Leu Arg Arg Leu Glu Met Tyr Cys Ala Pro
    50                  55                  60
```

```
Leu Gly Gly Gly Gly Ser Gly Gln Ala Gly Gln Gly Pro Ala Pro Glu
 65                  70                  75                  80

Leu Leu Gly Gly Pro Ser Val Phe Leu Phe Pro Pro Lys Pro Lys Asp
                 85                  90                  95

Thr Leu Met Ile Ser Arg Thr Pro Glu Val Thr Cys Val Val Val Asp
            100                 105                 110

Val Ser His Glu Asp Pro Glu Val Lys Phe Asn Trp Tyr Val Asp Gly
        115                 120                 125

Val Glu Val His Asn Ala Lys Thr Lys Pro Arg Glu Glu Gln Tyr Asn
    130                 135                 140

Ser Thr Tyr Arg Val Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
            180                 185                 190

Pro Gln Val Tyr Thr Ser Pro Pro Ser Arg Asp Glu Leu Thr Lys Asn
        195                 200                 205

Gln Val Ser Leu Arg Cys His Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Lys Pro Val Leu Asp Ser Asp Gly Ser Phe Phe Leu Tyr Ser Lys
                245                 250                 255

Leu Thr Val Asp Lys Ser Arg Trp Gln Gln Gly Asn Val Phe Ser Cys
            260                 265                 270

Ser Val Met His Glu Ala Leu His Asn His Tyr Thr Gln Lys Ser Leu
        275                 280                 285

Ser Leu Ser Pro Gly Lys Gln Val Gln Leu Gln Gln Ser Gly Pro Gly
    290                 295                 300

Leu Val Lys Pro Ser Gln Thr Leu Ser Leu Thr Cys Ala Ile Ser Gly
305                 310                 315                 320

Asp Ser Val Ser Ser Asn Ser Ala Ala Trp Asn Trp Ile Arg Gln Ser
                325                 330                 335

Pro Ser Arg Gly Leu Glu Trp Leu Gly Arg Thr Tyr Tyr Gly Ser Lys
            340                 345                 350

Trp Tyr Asn Asp Tyr Ala Pro Ser Val Lys Ser Arg Ile Ser Ile Asn
        355                 360                 365

Pro Asp Thr Ser Lys Asn Gln Phe Ser Leu Gln Leu Asn Ser Val Thr
    370                 375                 380

Pro Glu Asp Thr Ala Val Tyr Tyr Cys Thr Arg Gly Ile Trp Asn Ala
385                 390                 395                 400

Phe Asp Ile Trp Gly Gln Gly Thr Met Val Thr Val Ser Ser Gly Gly
                405                 410                 415

Gly Gly Ser Gly Gly Gly Ala Ser Gly Gly Gly Gly Ser Ser Ser Glu
            420                 425                 430

Leu Thr Gln Asp Pro Ala Val Ser Val Ala Leu Gly Gln Thr Val Arg
        435                 440                 445

Ile Thr Cys Gln Gly Asp Ser Leu Arg Ser Tyr Tyr Ala Ser Trp Tyr
    450                 455                 460

Gln Gln Lys Pro Gly Gln Ala Pro Leu Leu Val Ile Tyr Asp Arg Asp
465                 470                 475                 480

Asn Arg Pro Ser Gly Ile Pro Asp Arg Phe Ser Gly Ser Ser Ser Gly
```

```
                     485                 490                 495
Asn Thr Ala Ser Leu Thr Ile Thr Gly Ala Gln Ala Glu Asp Glu Ala
                500                 505                 510

Asp Tyr Tyr Cys Gln Ser Tyr Asp Thr Ser Leu Ser Trp Val Phe Gly
            515                 520                 525

Gly Gly Thr Gln Leu Thr Val Leu Gly
        530                 535

<210> SEQ ID NO 46
<211> LENGTH: 539
<212> TYPE: PRT
<213> ORGANISM: Artificial Sequence
<220> FEATURE:
<223> OTHER INFORMATION: scFv-Fc-IGF-1 fusion protein

<400> SEQUENCE: 46

Ala Gly Pro Glu Thr Leu Cys Gly Ala Glu Leu Val Asp Ala Leu Gln
1               5                   10                  15

Phe Val Cys Gly Asp Arg Gly Phe Tyr Phe Asn Lys Pro Thr Gly Tyr
            20                  25                  30

Gly Ser Ser Ser Arg Arg Ala Pro Gln Thr Gly Ile Val Asp Glu Cys
        35                  40                  45

Cys Phe Arg Ser Cys Asp Leu Arg Arg Leu Glu Met Tyr Cys Ala Pro
    50                  55                  60

Leu Gly Gly Gly Gly Ser Gln Ala Gly Gln Gly Pro Ala Pro Glu
65                  70                  75                  80

Leu Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
            100                 105                 110

Val Ser His Glu Asp Pro Glu Val Lys Phe Asn Trp Tyr Val Asp Gly
        115                 120                 125

Val Glu Val His Asn Ala Lys Thr Lys Pro Arg Glu Glu Gln Tyr Asn
    130                 135                 140

Ser Thr Tyr Arg Val Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
            180                 185                 190

Pro Gln Val Tyr Thr Ser Pro Pro Ser Arg Asp Glu Leu Thr Lys Asn
        195                 200                 205

Gln Val Ser Leu Arg Cys His Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Lys Pro Val Leu Asp Ser Asp Gly Ser Phe Phe Leu Tyr Ser Lys
                245                 250                 255

Leu Thr Val Asp Lys Ser Arg Trp Gln Gln Gly Asn Val Phe Ser Cys
            260                 265                 270

Ser Val Met His Glu Ala Leu His Asn His Tyr Thr Gln Lys Ser Leu
        275                 280                 285

Ser Leu Ser Pro Gly Lys Glu Val Gln Leu Val Gln Ser Gly Ala Glu
    290                 295                 300

Val Lys Lys Pro Gly Ser Ser Val Lys Val Ser Cys Lys Ala Ser Gly
```

```
                305                 310                 315                 320
Gly Thr Phe Ser Ser Tyr Ala Ile Ser Trp Val Arg Gln Ala Pro Gly
                325                 330                 335

Gln Gly Leu Glu Trp Met Gly Arg Ile Ile Pro Ile Leu Gly Ile Ala
                340                 345                 350

Asn Tyr Ala Gln Lys Phe Gln Gly Arg Val Thr Ile Thr Ala Asp Lys
                355                 360                 365

Ser Thr Ser Thr Ala Tyr Met Glu Leu Ser Ser Leu Arg Ser Glu Asp
            370                 375                 380

Thr Ala Val Tyr Tyr Cys Ala Arg Trp Gly Ser Gly Ser His Ala Phe
385                 390                 395                 400

Asp Ile Trp Gly Gln Gly Thr Thr Val Thr Val Ser Ser Gly Gly Gly
                405                 410                 415

Gly Ser Gly Gly Gly Ala Ser Ser Gly Gly Ser Ser Tyr Glu Leu
                420                 425                 430

Thr Gln Pro Pro Ser Thr Ser Gly Thr Pro Gly Gln Arg Val Ala Ile
                435                 440                 445

Ser Cys Ser Gly Ala Ser Ser Asn Ile Gly Ser Asn Ala Val Ser Trp
                450                 455                 460

Tyr Gln Gln Leu Pro Gly Thr Ala Pro Lys Leu Leu Ile Tyr Ser Asn
465                 470                 475                 480

Asn Gln Arg Pro Ser Gly Val Pro Asp Arg Phe Ser Gly Ser Lys Ser
                485                 490                 495

Gly Thr Ser Ala Ser Leu Ala Ile Ser Gly Leu Arg Ser Glu Asp Glu
                500                 505                 510

Ala Asp Tyr Tyr Cys Ala Ala Trp Asp Asp Ser Leu Asn Gly Trp Val
                515                 520                 525

Phe Gly Gly Gly Thr Gln Leu Thr Val Leu Gly
                530                 535

<210> SEQ ID NO 47
<211> LENGTH: 227
<212> TYPE: PRT
<213> ORGANISM: homo sapiens

<400> SEQUENCE: 47

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
            130                 135                 140
```

-continued

```
Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
            210                 215                 220

Pro Gly Lys
225
```

<210> SEQ ID NO 48
<211> LENGTH: 217
<212> TYPE: PRT
<213> ORGANISM: Artificial Sequence
<220> FEATURE:
<223> OTHER INFORMATION: mutant Fc domain

<400> SEQUENCE: 48

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Ser Pro Pro Ser Arg Asp Glu Leu
        115                 120                 125

Thr Lys Asn Gln Val Ser Leu Arg Cys His Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Lys Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
            210                 215
```

<210> SEQ ID NO 49
<211> LENGTH: 64
<212> TYPE: PRT
<213> ORGANISM: homo sapiens

<400> SEQUENCE: 49

Gly Pro Glu Thr Leu Cys Gly Ala Glu Leu Val Asp Ala Leu Gln Phe

```
            1               5                  10                 15
Val Cys Gly Asp Arg Gly Phe Tyr Phe Asn Lys Pro Thr Gly Tyr Gly
                    20                  25                  30

Ser Ser Ser Arg Arg Ala Pro Gln Thr Gly Ile Val Asp Glu Cys Cys
                    35                  40                  45

Phe Arg Ser Cys Asp Leu Arg Arg Leu Glu Met Tyr Cys Ala Pro Leu
                    50                  55                  60
```

<210> SEQ ID NO 50
<211> LENGTH: 90
<212> TYPE: PRT
<213> ORGANISM: homo sapiens

<400> SEQUENCE: 50

```
Lys Ser Val Lys Lys Arg Ser Val Ser Glu Ile Gln Leu Met His Asn
1               5                  10                 15

Leu Gly Lys His Leu Asn Ser Met Glu Arg Val Glu Trp Leu Arg Lys
                20                  25                  30

Lys Leu Gln Asp Val His Asn Phe Val Ala Leu Gly Ala Pro Leu Ala
                35                  40                  45

Pro Arg Asp Ala Gly Ser Gln Arg Pro Arg Lys Lys Glu Asp Asn Val
                50                  55                  60

Leu Val Glu Ser His Glu Lys Ser Leu Gly Glu Ala Asp Lys Ala Asp
65                  70                  75                  80

Val Asn Val Leu Thr Lys Ala Lys Ser Gln
                85                  90
```

<210> SEQ ID NO 51
<211> LENGTH: 90
<212> TYPE: PRT
<213> ORGANISM: Homo sapiens

<400> SEQUENCE: 51

```
Lys Ser Val Lys Lys Arg Ser Val Ser Glu Ile Gln Leu Met His Asn
1               5                  10                 15

Leu Gly Lys His Leu Asn Ser Met Glu Arg Val Glu Trp Leu Arg Lys
                20                  25                  30

Lys Leu Gln Asp Val His Asn Phe Val Ala Leu Gly Ala Pro Leu Ala
                35                  40                  45

Pro Arg Asp Ala Gly Ser Gln Arg Pro Arg Lys Lys Glu Asp Asn Val
                50                  55                  60

Leu Val Glu Ser His Glu Lys Ser Leu Gly Glu Ala Asp Lys Ala Asp
65                  70                  75                  80

Val Asn Val Leu Thr Lys Ala Lys Ser Gln
                85                  90
```

<210> SEQ ID NO 52
<211> LENGTH: 34
<212> TYPE: PRT
<213> ORGANISM: Homo sapiens

<400> SEQUENCE: 52

```
Ser Val Ser Glu Ile Gln Leu Met His Asn Leu Gly Lys His Leu Asn
1               5                  10                 15

Ser Met Glu Arg Val Glu Trp Leu Arg Lys Leu Gln Asp Val His
                20                  25                  30

Asn Phe
```

```
<210> SEQ ID NO 53
<211> LENGTH: 828
<212> TYPE: DNA
<213> ORGANISM: Homo sapiens

<400> SEQUENCE: 53
aaaagtcacc atttaagggg tctgcagtcc aattcatcag ttgtctttag tttactcagc      60
atcagctact aacatacctg aacgaagatc ttgttctaag acattgtatg tgaagatgat     120
acctgcaaaa gacatggcta aagttatgat tgtcatgttg gcaatttgtt ttcttacaaa     180
atcggatggg aaatctgtta agaagagatc tgtgagtgaa atacagctta tgcataacct     240
gggaaaacat ctgaactcga tggagagagt agaatggctg cgtaagaagc tgcaggatgt     300
gcacaatttt gttgcccttg gagctcctct agctcccaga gatgctggtt cccagaggcc     360
ccgaaaaaag gaagacaatg tcttggttga gagccatgaa aaaagtcttg gagaggcaga     420
caaagctgat gtgaatgtat taactaaagc taaatcccag tgaaaatgaa aacagatatt     480
gtcagagttc tgctctagac agtgtagggc aacaatacat gctgctaatt caaagctcta     540
ttaagatttc caagtgccaa tatttctgat ataacaaact acatgtaatc catcactagc     600
catgataact gcaattttaa ttgattattc tgattccact tttattcatt tgagttattt     660
taattatctt ttctattgtt tattcttttt aaagtatgtt attgcataat ttataaaaga     720
ataaaattgc acttttaaac ctctcttcta ccttaaaatg taaaacaaaa atgtaatgat     780
cataagtcta aataaatgaa gtatttctca ctcaaaaaaa aaaaaaaa                  828
```

AGENTS THAT SPECIFICALLY BIND MATRILIN-3 AND THEIR USE

CROSS REFERENCE TO RELATED APPLICATIONS

This application is the U.S. National Stage of International Application No. PCT/US2015/011433, filed Jan. 14, 2015, which was published in English under PCT Article 21(2), which in turn claims the benefit of U.S. Provisional Application No. 61/927,904, filed Jan. 15, 2014. The provisional application is incorporated by reference herein.

FIELD OF THE DISCLOSURE

This relates to monoclonal antibodies, antigen binding fragments, and conjugates that specifically bind to matrilin-3, as well as methods and agents for treating or preventing cartilage disorders.

BACKGROUND

A child's growth is dependent on the proper functioning of the growth plate, a specialized cartilage structure located at the end of long bones and within the vertebrae. The primary function of the growth plate is to generate new cartilage, which is then converted into bone tissue and results in the lengthening of bones (i.e., the growth of the child). Mutations in one or more of the many genes that control growth plate function can cause severe skeletal growth disorders in children.

Current treatments for skeletal cartilage disorders are limited. One method of treatment involves the administration of recombinant growth hormone, but the results are less than optimal and systemic treatment using growth hormone carries a risk of increased intracranial pressure, slipped capital femoral epiphysis, insulin resistance, and possibly type II diabetes mellitus. Thus, there is a need for therapeutic agents and treatment methods that avoid the systemic risks of current therapies.

SUMMARY

Disclosed herein is the surprising discovery of antibodies and antigen binding fragments that specifically bind to matrilin-3 and which can be used to target therapeutic payloads to growth plate cartilage. Conjugates of such antibodies or antigen binding fragments that are linked to a chondrogenic agent target to growth plate cartilage and induce chondrogenesis, while diminishing adverse effects on non-target tissues, such as those seen with systemic use of growth hormone Isolated monoclonal antibodies and antigen binding fragments that specifically bind to matrilin-3, conjugates thereof, and methods of using these molecules, are provided. In some embodiments, the antibody or antigen binding fragment includes a heavy chain variable region including a heavy chain complementarity determining region (HCDR)1, a HCDR2, and a HCDR3, and a light chain variable region including a light chain complementarity determining region (LCDR)1, a LCDR2, and a L-CDR3, of the amino acid sequences set forth as one of (a) SEQ ID NO: 1 and SEQ ID NO: 2, (b) SEQ ID NO: 3 and SEQ ID NO: 4, or (c) SEQ ID NO: 5 and SEQ ID NO: 6, wherein the monoclonal antibody or antigen binding fragment specifically binds to matrilin-3.

In additional embodiments, the HCDR1, HCDR2, and HCDR3 comprise the amino acid sequences set forth as residues 26-33, 51-58, and 97-106 of SEQ ID NO: 1, respectively, and the LCDR1, LCDR2, and LCDR3 comprise the amino acid sequence set forth as residues 27-32, 50-52, and 89-97 of SEQ ID NO: 2, respectively. In more embodiments, the HCDR1, HCDR2, and HCDR3 comprise the amino acid sequences set forth as residues 26-33, 53-61, and 100-109 of SEQ ID NO: 3, respectively, and the LCDR1, LCDR2, and LCDR3 comprise the amino acid sequence set forth as residues 26-31, 49-51, and 88-97 of SEQ ID NO: 4 respectively. In further embodiments, the HCDR1, HCDR2, and HCDR3 comprise the amino acid sequences set forth as residues 26-33, 51-58, 97-108 of SEQ ID NO: 5, respectively, and the LCDR1, LCDR2, and LCDR3 comprise the amino acid sequence set forth as residues 26-33, 51-53, and 90-100 of SEQ ID NO: 6, respectively.

In some embodiments antibody or antigen binding fragment includes heavy and light chain variable regions including the amino acid sequences set forth as SEQ ID NO: 1 and SEQ ID NO: 2, respectively, SEQ ID NO: 3 and SEQ ID NO: 4, respectively; or SEQ ID NO: 5 and SEQ ID NO: 6, respectively.

In some embodiments, the conjugate can include a chondrogenic agent covalently linked to the monoclonal antibody or antigen binding fragment that specifically binds to matrilin-3. For example, the antibody or antigen binding fragment can be conjugated to a growth hormone, an insulin-like growth factor-I, an Indian Hedgehog, a bone morphogenetic protein, a C-type natriuretic protein, a Wnt protein, or a steroid, or a fragment thereof that induces chondrogenesis. In additional embodiments, the conjugates can include an anti-arthritis agent, such as a parathyroid (PTH) hormone or functional fragment thereof.

The antibodies, antigen binding fragments, and conjugates can be used for a variety of purposes, including in methods of increasing chondrogenesis in cartilage tissue, methods of treating a subject with a cartilage disorder, and methods of increasing the height of a subject. These methods can include administering a therapeutically effective amount of a disclosed antibody, antigen binding fragment, or conjugate to a subject with a cartilage disorder.

It will be understood that the antibodies, antigen binding fragments and methods are useful beyond the specific circumstances that are described in detail herein. The foregoing and features and advantages of the disclosure will become more apparent from the following detailed description, which proceeds with reference to the accompanying figures.

BRIEF DESCRIPTION OF THE FIGURES

FIGS. 5A and 5B show a set of schematic diagrams and plasmid vector maps illustrating construction of dimeric (FIG. 5A) or monomeric (FIG. 5B) fusion proteins including IGF-1 linked to a clone 13-, 22-, or 26-based scFv and a Fc domain.

SEQUENCE LISTING

Figure 1A:
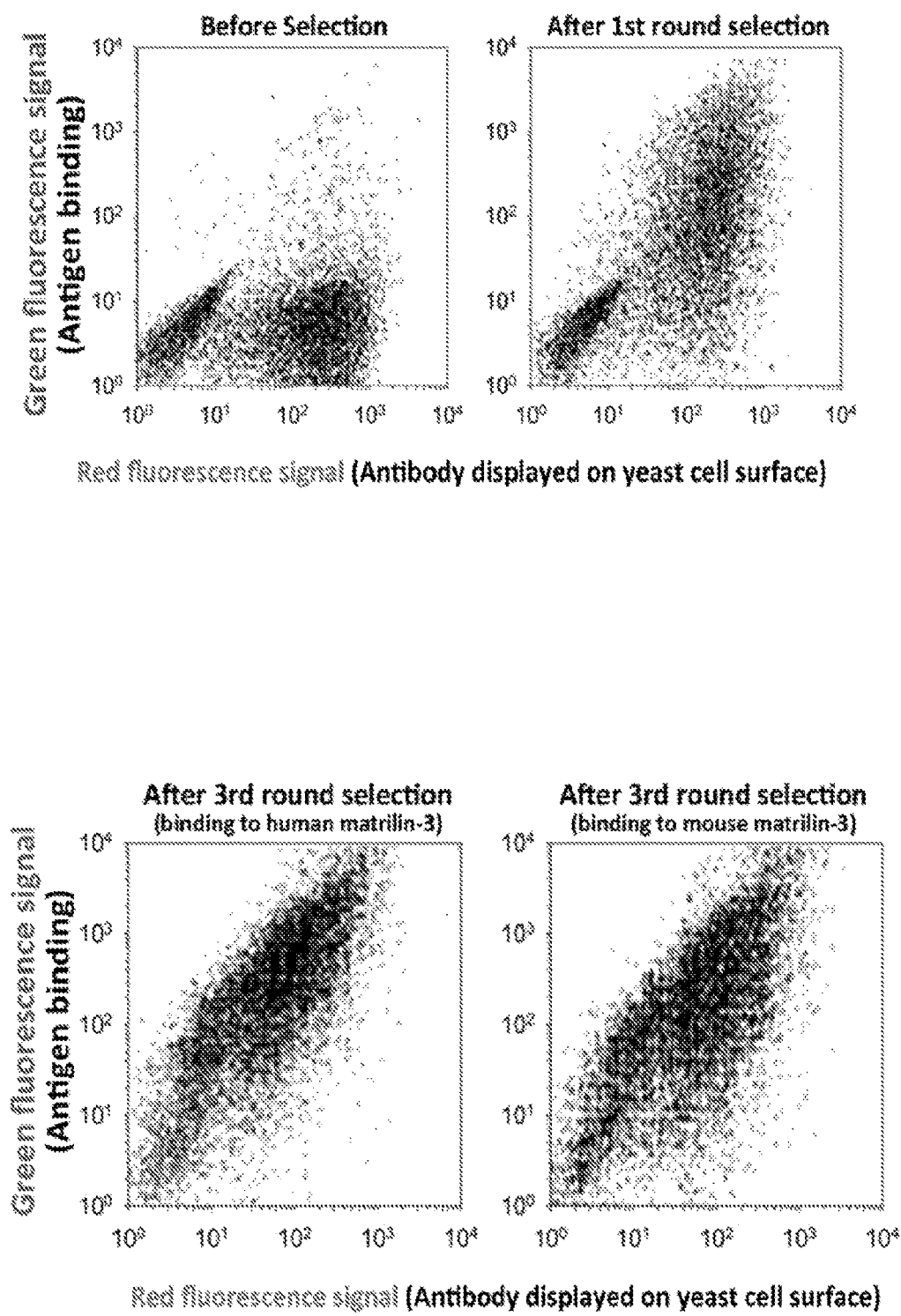
FIGS. 1A-1D are a series of graphs illustrating selection of matrilin-3-binding antibody fragments and assessment of their binding characteristics. (A) A yeast display antibody library was panned against human (first and second rounds of panning) and mouse (third round) matrilin-3 protein. Fluorescence-activated cell sorting showed that the binding affinity of the enriched pool of yeast display antibody fragments toward matrilin-3 dramatically increased after three rounds of selection, when compared to the naïve library. (B-C) The binding abilities of 36 clones of antibody fragments to human or mouse recombinant matrilin-3 protein were evaluated by ELISA. Plastic wells were coated with matrilin-3 protein or bovine serum albumin (BSA) and then incubated with antibody fragments, washed and detected using a HRP-conjugated anti-Fc antibody. Absorbance was normalized to background signal of 3% non-fat milk. (D) The tissue binding specificity of the three selected clones of antibody fragments were assessed by ELISA. Tissue lysates from a panel of organs from 4-day old mice were used to coat plastic wells. Individual antibody fragments were incubated in the wells, then washed and detected using HRP-conjugated anti-Fc antibody. A non-specific antibody fragment directed against an irrelevant protein served as a negative control and a commercial antibody against matrilin-3 served as a positive control. For panels b-d, data represent mean±SEM from three independent experiments (n=9).

The nucleic and amino acid sequences are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~112 kb), which was created on Jul. 11, 2016, which is incorporated by reference herein. In the accompanying sequence listing:

SEQ ID NO: 1 is the amino acid sequence of the $V_H$ of the matrilin-3 specific clone 13 mAb.

EVQLVQSGAEVKKPGASVKVSCKASGGTFSSYAISWVRQAPGQGLEWMG

GIIPIFGTANYAQKFQGRVTITADKSTSTAYMELSSLRSEDTAVYYCARG

QGYWFDPWGQGTLVTSS

SEQ ID NO: 2 is the amino acid sequence of the $V_L$ of the matrilin-3 specific clone 13 mAb.

DVQLTQSPSSLSASVGDRVTITCQASQDISNYLNWYQQKPGK

APKLLIYDASNLETGVPSRFSGSGSGTDFTFTISSLQPEDIAT

YYCQQYDNLPLTFGGGTKLEIKR

SEQ ID NO: 3 is the amino acid sequence of the $V_H$ of the matrilin-3 specific clone 22 mAb.

QVQLQQSGPGLVKPSQTLSLTCAISGDSVSSNSAAWNWIRQSPSRGLEWL

GRTYYGSKWYNDYAPSVKSRISINPDTSKNQFSLQLNSVTPEDTAVYYCT

RGIWNAFDIWGQGTMVTVSS

SEQ ID NO: 4 is the amino acid sequence of the $V_L$ of the matrilin-3 specific clone 22 mAb.

SSELTQDPAVSVALGQTVRITCQGDSLRSYYASWYQQKPGQAPLLVIYDR

DNRPSGIPDRFSGSSSGNTASLTITGAQAEDEADYYCQSYDTSLSWVFGG

GTQLTVLG

SEQ ID NO: 5 is the amino acid sequence of the $V_H$ of the matrilin-3 specific clone 26 mAb.

EVQLVQSGAEVKKPGSSVKVSCKASGGTFSSYAISWVRQAPGQGLEWMGR

IIPILGIANYAQKFQGRVTITADKSTSTAYMELSSLRSEDTAVYYCARWG

SGSHAFDIWGQGTTVTVSS

SEQ ID NO: 6 is the amino acid sequence of the $V_L$ of the matrilin-3 specific clone 26 mAb.

SYELTQPPSTSGTPGQRVAISCSGASSNIGSNAVSWYQQLPGTAPKLLIY

SNNQRPSGVPDRFSGSKSGTSASLAISGLRSEDEADYYCAAWDDSLNGWV

FGGGTQLTVLG

SEQ ID NO: 7 is an exemplary nucleic acid sequence encoding an scFv including the $V_H$ and $V_L$ of the matrilin-3 specific clone 13 mAb.

CTGGTGCAGTCTGGGGCTGAGGTGAAGAAGCCTGGGGCCTCAGTGAAGGT

CTCCTGCAAGGCTTCTGGAGGCACCTTCAGCAGCTATGCTATCAGCTGGG

TGCGACAGGCCCCTGGACAAGGGCTTGAGTGGATGGGAGGGATCATCCCT

ATCTTTGGTACAGCAAACTACGCACAGAAGTTCCAGGGCAGAGTCACGAT

TACCGCGGACAAATCCACGAGCACAGCCTACATGGAGCTGAGCAGCCTGA

GATCTGAGGACACGGCCGTGTATTACTGTGCGAGAGGCCAAGGGTATTGG

TTCGACCCCTGGGGCCAGGGAACCCTGGTCACCGTCTCCTCAGGAGGTGG

CGGGTCTGGTGGAGGCGCTAGCAGTGGTGGCGGATCCGACGTCCAGTTGA

CCCAGTCTCCATCCTCCCTGTCTGCATCTGTAGGAGACAGAGTCACCATC

ACTTGCCAGGCGAGTCAGGACATTAGCAACTATTTAAATTGGTATCAGCA

GAAACCAGGGAAAGCCCCTAAGCTCCTGATCTACGATGCATCCAATTTGG

AAACAGGGGTCCCATCAAGGTTCAGTGGAAGTGGATCTGGGACAGATTTT

ACTTTCACCATCAGCAGCCTGCAGCCTGAAGATATTGCAACATATTACTG

TCAACAGTATGATAATCTCCCGCTCACTTTCGGCGGAGGGACCAAGCTGG

AGATCAAA

SEQ ID NO: 8 is an exemplary nucleic acid sequence encoding an scFv including the $V_H$ and $V_L$ of the matrilin-3 specific clone 22 mAb.

CAGGTACAGCTGCAGCAGTCAGGTCCAGGACTGGTGAAGCCCTCGCAGAC

CCTCTCACTCACCTGTGCCATCTCCGGGGACAGTGTCTCTAGCAACAGTG

CTGCTTGGAACTGGATCAGGCAGTCCCCATCGAGAGGCCTTGAGTGGCTG

GGAAGGACATACTACGGGTCCAAGTGGTATAATGATTATGCGCCATCTGT

GAAAAGTCGAATAAGTATCAACCCAGACACATCCAAGAACCAGTTCTCCC

TGCAACTGAACTCTGTGACTCCCGAAGACACGGCTGTGTATTACTGTACA

AGGGGTATTTGGAATGCTTTTGATATCTGGGGCCAAGGGACAATGGTCAC

CGTCTCTTCAGGAGGTGGCGGGTCTGGTGGAGGCGCTAGCGGTGGTGGCG

GATCCTCTTCTGAGCTGACTCAGGACCCTGCTGTGTCTGTGGCCTTGGGA

CAGACAGTCAGGATCACATGCCAAGGAGACAGCCTCAGAAGCTATTATGC

AAGCTGGTACCAGCAGAAGCCAGGACAGGCCCCTTTACTTGTCATCTATG

ATAGGGACAACCGGCCCTCAGGGATCCCAGACCGATTCTCTGGCTCCAGC

TCAGGAAACACAGCTTCCTTGACCATCACTGGGGCTCAGGCGGAAGATGA

GGCTGATTATTACTGCCAGTCCTATGACACCAGCCTGAGTTGGGTGTTCG

GCGGAGGCACCCAGCTGACCGTCCTC

SEQ ID NO: 9 is an exemplary nucleic acid sequence encoding an scFv including the $V_H$ and $V_L$ of the matrilin-3 specific clone 26 mAb.

GAGGTCCAGCTGGTGCAGTCTGGGGCTGAGGTGAAGAAGCCTGGGTCCTC

GGTGAAGGTCTCCTGCAAGGCTTCTGGAGGCACCTTCAGCAGCTATGCTA

TCAGCTGGGTGCGACAGGCCCCTGGACAAGGGCTTGAGTGGATGGGAAGG

ATCATCCCTATCCTTGGTATAGCAAACTACGCACAGAAGTTCCAGGGCAG

AGTCACGATTACCGCGGACAAATCCACGAGCACAGCCTACATGGAGCTGA

GCAGCCTGAGATCTGAGGACACGGCCGTGTATTACTGTGCGAGATGGGGT

AGTGGGAGCCATGCTTTTGATATCTGGGGCCAAGGGACCACGGTCACCGT

CTCCTCAGGAGGTGGCGGGTCTGGTGGAGGCGCTAGCAGTGGTGGCGGAT

CCTCCTATGAGCTGACTCAGCCACCCTCGACGTCTGGGACCCCCGGGCAG

AGGGTCGCCATCTCTTGTTCTGGGGCCAGTTCCAATATCGGAAGTAATGC

TGTTAGCTGGTACCAGCAGCTCCCAGGAACGGCCCCCAAACTCCTCATCT

ATAGCAATAATCAACGGCCCTCAGGGGTCCCTGACCGATTCTCTGGCTCC

AAGTCTGGCACCTCAGCCTCCCTGGCCATCAGTGGGCTCCGGTCCGAGGA

TGAGGCTGATTATTACTGTGCAGCATGGGATGACAGCCTCAATGGCTGGG

TGTTCGGCGGAGGGACCCAGCTCACCGTTTTA

SEQ ID NO: 10 is the amino acid sequence of the variable region of an scFv including the $V_H$ and $V_L$ of the matrilin-3 specific clone 13 mAb.

LVQSGAEVKKPGASVKVSCKASGGTFSSYAISWVRQAPGQGLEWMGGIIP

IFGTANYAQKFQGRVTITADKSTSTAYMELSSLRSEDTAVYYCARGQGYW

FDPWGQGTLVTVSSGGGGSGGGASSGGGSDVQLTQSPSSLSASVGDRVTI

TCQASQDISNYLNWYQQKPGKAPKLLIYDASNLETGVPSRFSGSGSGTDF

TFTISSLQPEDIATYYCQQYDNLPLTFGGGTKLEIK

SEQ ID NO: 11 is the amino acid sequence of an scFv including the $V_H$ and $V_L$ of the matrilin-3 specific clone 22 mAb.

LQQSGPGLVKPSQTLSLTCAISGDSVSSNSAAWNWIRQSPSRGLEWLGRT

YYGSKWYNDYAPSVKSRISINPDTSKNQFSLQLNSVTPEDTAVYYCTRGI

WNAFDIWGQGTMVTVSSGGGGSGGGASGGGGSSSELTQDPAVSVALGQTV

RITCQGDSLRSYYASWYQQKPGQAPLLVIYDRDNRPSGIPDRFSGSSSGN

TASLTITGAQAEDEADYYCQSYDTSLSWVFGGGTQLTVL

SEQ ID NO: 12 is the amino acid sequence of an scFv including the $V_H$ and $V_L$ of the matrilin-3 specific clone 26 mAb.

LVQSGAEVKKPGSSVKVSCKASGGTFSSYAISWVRQAPGQGLEWMGRIIP

ILGIANYAQKFQGRVTITADKSTSTAYMELSSLRSEDTAVYYCARWGSGS

HAFDIWGQGTTVTVSSGGGGSGGGASSGGGSSYELTQPPSTSGTPGQRVA

ISCSGASSNIGSNAVSWYQQLPGTAPKLLIYSNNQRPSGVPDRFSGSKSG

TSASLAISGLRSEDEADYYCAAWDDSLNGWVFGGGTQLTVL

SEQ ID NO: 13 is an exemplary nucleic acid sequence encoding an scFv including the $V_H$ and $V_L$ of the matrilin-3 specific clone 13 mAb linked to an Fc domain.

ctggtgcagtctggggctgaggtgaagaagcctggggcctcagtgaaggt
ctcctgcaaggcttctggaggcaccttcagcagctatgctatcagctggg
tgcgacaggcccctggacaagggcttgagtggatgggagggatcatccct
atctttggtacagcaaactacgcacagaagttccagggcagagtcacgat
taccgcggacaaatccacgagcacagcctacatggagctgagcagcctga
gatctgaggacacggccgtgtattactgtgcgagaggccaagggtattgg
ttcgacccctggggccagggaaccctggtcaccgtctcctcaggaggtgg
cgggtctggtggaggcgctagcagtggtggcggatccgacgtccagttga
cccagtctccatcctccctgtctgcatctgtaggagacagagtcaccatc
acttgccaggcgagtcaggacattagcaactatttaaattggtatcagca
gaaaccagggaaagcccctaagctcctgatctacgatgcatccaatttgg
aaacaggggtcccatcaaggttcagtggaagtggatctgggacagatttt
actttcaccatcagcagcctgcagcctgaagatattgcaacatattactg
tcaacagtatgataatctcccgctcactttcggcggagggaccaagctgg
agatcaaacgtggccaggcggccaagggcccgacaaaactcacacatgc
ccaccgtgcccagcacctgaactcctggggggaccgtcagtcttcctctt
ccccccaaaacccaaggacaccctcatgatctcccggaccctgaggtca
catgcgtggtggtggacgtgag

```
gggcccgacaaaactcacacatgcccaccgtgcccagcacctgaactcct
gggggggaccgtcagtcttcctcttccccccaaacccaaggacaccctca
tgatctcccggacccctgaggtcacatgcgtggtggtggacgtgagccac
gaagaccctgaggtcaagttcaactggtacgtggacggcgtggaggtgca
taatgccaagacaaagccgcgggaggagcagtacaacagcacgtaccgtg
tggtcagcgtcctcaccgtcctgcaccaggactggctgaatggcaaggag
tacaagtgcaaggtctccaacaaagccctcccagcccccatcgagaaaac
catctccaaagccaaagggcagccccgagaaccacaggtgtacaccctgc
ccccatcccgggatgagctgaccaagaaccaggtcagcctgacctgcctg
gtcaaaggcttctatcccagcgacatcgccgtggagtgggagagcaatgg
gcagccggagaacaactacaagaccacgcctcccgtgctggactccgacg
gctccttcttcctctacagcaagctcaccgtggacaagagcaggtggcag
caggggaacgtcttctcatgctccgtgatgcatgaggctctgcacaacca
ctacacgcagaagagcctctccctgtctccgggtaaagcggccgctcgag
gactaaacgacatcttcgaggctcagaaaatcgaaggca
```

SEQ ID NO: 16 is the amino acid sequence of the precursor of matrilin-3 (GENBANK Acc. No. NP_002372.1, incorporated by reference herein as present in the database on Dec. 1, 2013)

```
MPRPAPARRLPGLLLLLWPLLLLPSAAPDPVARPGFRRLETRGPGGSPGR
RPSPAAPDGAPASGTSEPGRARGAGVCKSRPLDLVFIIDSSRSVRPLEFT
KVKTFVSRIIDTLDIGPADTRVAVVNYASTVKIEFQLQAYTDKQSLKQAV
GRITPLSTGTMSGLAIQTAMDEAFTVEAGAREPSSNIPKVAIIVTDGRPQ
DQVNEVAARAQASGIELYAVGVDRADMASLKMMASEPLEEHVFYVETYGV
IEKLSSRFQETFCALDPCVLGTHQCQHVCISDGEGKHHCECSQGYTLNAD
KKTCSALDRCALNTHGCEHICVNDRSGSYHCECYEGYTLNEDRKTCSAQD
KCALGTHGCQHICVNDRTGSHHCECYEGYTLNADKKTCSVRDKCALGSHG
CQHICVSDGAASYHCDCYPGYTLNEDKKTCSATEEARRLVSTEDACGCEA
TLAFQDKVSSYLQRLNTKLDDILEKLKINEYGQIHR
```

SEQ ID NO: 17 is an exemplary nucleic acid sequence encoding the precursor of matrilin-3 (GENBANK Acc. No. NM_002381.4, incorporated by reference herein as present in the database on Dec. 1, 2013).

```
aaatccgagcctcgcgtgggctcctggcccccgacggacaccaccaggcc
cacggagcccaccatgccgcgcccggccccgcgcgccgcctcccggac
tcctcctgctgctctggccgctgctgctgctgccctccgccgccccgac
cccgtggcccgcccgggcttccggaggctggagacccgaggtcccggggg
cagccctggacgccgcccctctcctgcggctcccgacggcgcgcccgctt
ccgggaccagcgagcctggccgcgcccgcggtgcaggtgtttgcaagagc
agaccccttggacctggtgtttatcattgatagttctcgtagcgtacggcc
cctggaattcaccaaagtgaaaactttttgtctcccggataatcgacactc
tggacattgggccagccgacacgcgggtggcagtggtgaactatgctagc
actgtgaagatcgagttccaactccaggcctacacagataagcagtccct
gaagcaggccgtgggtcgaatcacacccttgtcaacaggcaccatgtcag
gcctagccatccagacagcaatggacgaagccttcacagtggaggcaggg
gctcgagaccctcttctaacatccctaaggtggccatcattgttacaga
tgggaggccccaggaccaggtgaatgaggtggcggctcgggcccaagcat
ctggtattgagctctatgctgtgggcgtggaccgggcagacatggcgtcc
ctcaagatgatggccagtgagcccctagaggagcatgttttctacgtgga
gacctatgggtcattgagaaactttcctctagattccaggaaaccttct
gtgcgctggacccctgtgtgcttggaacacaccagtgccagcacgtctgc
atcagtgatggggaaggcaagcaccactgtgagtgtagccaaggatacac
cttgaatgccgacaagaaaacgtgttcagctcttgataggtgtgctctta
acacccacggatgtgagcacatctgtgtgaatgacagaagtggctcttat
cattgtgagtgctatgaaggttataccttgaatgaagacaggaaaacttg
ttcagctcaagataaatgtgctttgggtacccatgggtgtcagcacattt
gtgtgaatgacagaacagggtcccatcattgtgaatgctatgagggctac
actctgaatgcagataaaaaaacatgttcagtccgtgacaagtgtgccct
aggctctcatggttgccagcacatttgtgtgagtgatggggccgcatcct
accactgtgattgctatcctggctacacccttaaatgaggacaagaaaca
tgttcagccactgaggaagcacgaagacttgtttccactgaagatgcttg
tggatgtgaagctacactggcattccaggacaaggtcagctcgtatcttc
aaagactgaacactaaacttgatgacattttggagaagttgaaaataaat
gaatatggacaaatacatcgttaaattgctccaatttctcacctgaaaat
gtggacagcttggtgtacttaatactcatgcattcttttgcacacctgtt
attgccaatgttcctgctaataatttgccattatctgtattaatgcttga
atattactggataaattgtatgaagatcttctgcagaatcagcatgattc
ttccaaggaaatacatatgcagatacttattaagagcaaactttagtgtc
tctaagttatgactgtgaaatgattggtaggaaatagaatgaaaagttta
gtgtttctttatctactaattgagccatttaatttttaaatgtttatatt
agataaccatattcacaatggaaactttaggtctagtttcttttgatagt
atttataatataaatcaatcttattactgagagtgcaaattgtacaaggt
atttacacatacaacttcatataactgagatgaatgtaattttgaactgt
ttaacacttttttgttttttgcttattttgttggagtattattgaagatgt
gatcaatagattgtaatacacatatctaaaaatagttaacacagatcaag
tgaacattacattgccatttttaattcattctggtctttgaaagaaatgt
actactaaagagcactagttgtgaatttagggtgttaaacttttttaccaa
gtacaaaaatcccaaattcactttattattttgcttcaggatccaagtga
caaagtatatatttataaaattgctataaatcgacaaaatctaatgttg
tcttttttaatgttagtgatccacctgcctcagcctcccaaagtgctggga
ttacaggcttgaaagtctaactttttttttacttatatatttgatacatat
aattcttttggctttgaaacttgcaactttgagaacaaaacagtccttta
```

-continued aattttgcactgctcaattctgtttttcgtttgcattgtctttaatataa taaaagttattacctttacatattatcatgtctatttttgatgactcatc aattttgtctattaaagatatttctttaaattaaaaaaaaaaaaaaaaa SEQ ID NOs: 18-20 are exemplary amino acid and DNA sequences of human growth hormone (GH).
SEQ ID NOs: 21-23 and 49 are exemplary amino acid and DNA sequences of IGF-1.
SEQ ID NOs: 24-26 are exemplary amino acid and DNA sequences of Indian Hedgehog (IHH) proteins.
SEQ ID NOs: 27-29 are exemplary amino acid and DNA sequences of bone morphogenic proteins (BMP).
SEQ ID NOs: 30-34 are exemplary amino acid and DNA sequences of CNP proteins.
SEQ ID NOs: 35-37 are exemplary amino acid and DNA sequences of WNT proteins.
SEQ ID NOs: 38-40 are the amino acid sequences of peptide linkers.
SEQ ID NO: 41 is an exemplary amino acid sequence of a fusion protein including IGF-1 linked to a matrilin-3 clone 13-based scFv linked to a mutant (dimeric) IgG1-based Fc domain.

AGPETLCGAELVDALQFVCGDRGFYFNKPTGYGSSSRRAPQTGIVDECCF

RSCDLRRLEMYCAPLGGGGSEVQLVQSGAEVKKPGASVKVSCKASGGTFS

SYAISWVRQAPGQGLEWMGGIIPIFGTANYAQKFQGRVTITADKSTSTAY

MELSSLRSEDTAVYYCARGQGYWFDPWGQGTLVTVSSGGGGSGGGASSGG

GSDVQLTQSPSSLSASVGDRVTITCQASQDISNYLNWYQQKPGKAPKLLI

YDASNLETGVPSRFSGSGSGTDFTFTISSLQPEDIATYYCQQYDNLPLTF

GGGTKLEIKRGQAGQGPDKTHTCPPCPAPELLGGPSVFLFPPKPKDTLMI

SRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPP

SRDELTKNQVSLTCLVKGFYPSDIAVEWESNGQPENNYKTTPPVLDSDGS

FFLYSKLTVDKSRWQQGNVFSCSVMHEALHNHYTQKSLSLSPGK

SEQ ID NO: 42 is an exemplary amino acid sequence of a fusion protein including IGF-1 linked to a matrilin-3 clone 22-based scFv linked to a wildtype (dimeric) IgG1-based Fc domain.

AGPETLCGAELVDALQFVCGDRGFYFNKPTGYGSSSRRAPQTGIVDECCF

RSCDLRRLEMYCAPLGGGGSQVQLQQSGPGLVKPSQTLSLTCAISGDSVS

SNSAAWNWIRQSPSRGLEWLGRTYYGSKWYNDYAPSVKSRISINPDTSKN

QFSLQLNSVTPEDTAVYYCTRGIWNAFDIWGQGTMVTVSSGGGGSGGGAS

GGGGSSSELTQDPAVSVALGQTVRITCQGDSLRSYYASWYQQKPGQAPLL

VIYDRDNRPSGIPDRFSGSSSGNTASLTITGAQAEDEADYYCQSYDTSLS

WVFGGGTQLTVLGGQAGQGPDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK

SEQ ID NO: 43 is an exemplary amino acid sequence of a fusion protein including IGF-1 linked to a matrilin-3 clone 26-based scFv linked to a wildtype (dimeric) IgG1-based Fc domain.

AGPETLCGAELVDALQFVCGDRGFYFNKPTGYGSSSRRAPQTGIVDECCF

RSCDLRRLEMYCAPLGGGGSEVQLVQSGAEVKKPGSSVKVSCKASGGTFS

SYAISWVRQAPGQGLEWMGRIIPILGIANYAQKFQGRVTITADKSTSTAY

MELSSLRSEDTAVYYCARWGSGSHAFDIWGQGTTVTVSSGGGGSGGGASS

GGGSSYELTQPPSTSGTPGQRVAISCSGASSNIGSNAVSWYQQLPGTAPK

LLIYSNNQRPSGVPDRFSGSKSGTSASLAISGLRSEDEADYYCAAWDDSL

NGWVFGGGTQLTVLGGQAGQGPDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK

SEQ ID NO: 44 is an exemplary amino acid sequence of a fusion protein including IGF-1 linked to a matrilin-3 clone 13-based scFv linked to a mutant (monomeric) IgG1-based Fc domain.

AGPETLCGAELVDALQFVCGDRGFYFNKPTGYGSSSRRAPQTGIVDECCF

RSCDLRRLEMYCAPLGGGGSGQAGQGPAPELLGGPSVFLFPPKPKDTLMI

SRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTSPP

SRDELTKNQVSLRCHVKGFYPSDIAVEWESNGQPENNYKTTKPVLDSDGS

FFLYSKLTVDKSRWQQGNVFSCSVMHEALHNHYTQKSLSLSPGKEVQLVQ

SGAEVKKPGASVKVSCKASGGTFSSYAISWVRQAPGQGLEWMGGIIPIFG

TANYAQKFQGRVTITADKSTSTAYMELSSLRSEDTAVYYCARGQGYWFDP

WGQGTLVTVSSGGGGSGGGASSGGGSDVQLTQSPSSLSASVGDRVTITCQ

ASQDISNYLNWYQQKPGKAPKLLIYDASNLETGVPSRFSGSGSGTDFTFT

ISSLQPEDIATYYCQQYDNLPLTFGGGTKLEIKR

SEQ ID NO: 45 is an exemplary amino acid sequence of a fusion protein including IGF-1 linked to a matrilin-3 clone 22-based scFv linked to a mutant (monomeric) IgG1-based Fc domain.

AGPETLCGAELVDALQFVCGDRGFYFNKPTGYGSSSRRAPQTGIVDECCF

RSCDLRRLEMYCAPLGGGGSGQAGQGPAPELLGGPSVFLFPPKPKDTLMI

SRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTSPP

SRDELTKNQVSLRCHVKGFYPSDIAVEWESNGQPENNYKTTKPVLDSDGS

FFLYSKLTVDKSRWQQGNVFSCSVMHEALHNHYTQKSLSLSPGKQVLQQ

SGPGLVKPSQTLSLTCAISGDSVSSNSAAWNWIRQSPSRGLEWLGRTYYG

SKWYNDYAPSVKSRISINPDTSKNQFSLQLNSVTPEDTAVYYCTRGIWNA

```
-continued
FDIWGQGTMVTVSSGGGGSGGGASGGGGSSSELTQDPAVSVALGQTVRIT

CQGDSLRSYYASWYQQKPGQAPLLVIYDRDNRPSGIPDRFSGSSSGNTAS

LTITGAQAEDEADYYCQSYDTSLSWVFGGGTQLTVLG
```

SEQ ID NO: 46 is an exemplary amino acid sequence of a fusion protein including IGF-1 linked to a matrilin-3 clone 26-based scFv linked to a mutant (monomeric) IgG1-based Fc domain.

```
AGPETLCGAELVDALQFVCGDRGFYFNKPTGYGSSSRRAPQTGIVDECCF

RSCDLRRLEMYCAPLGGGGSGQAGQGPAPELLGGPSVFLFPPKPKDTLMI

SRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTSPP

SRDELTKNQVSLRCHVKGFYPSDIAVEWESNGQPENNYKTTKPVLDSDGS

FFLYSKLTVDKSRWQQGNVFSCSVMHEALHNHYTQKSLSLSPGKEVQLVQ

SGAEVKKPGSSVKVSCKASGGTFSSYAISWVRQAPGQGLEWMGRIIPILG

IANYAQKFQGRVTITADKSTSTAYMELSSLRSEDTAVYYCARWGSGSHAF

DIWGQGTTVTVSSGGGGSGGGASSGGGSSYELTQPPSTSGTPGQRVAISC

SGASSNIGSNAVSWYQQLPGTAPKLLIYSNNQRPSGVPDRFSGSKSGTSA

SLAISGLRSEDEADYYCAAWDDSLNGWVFGGGTQLTVLG
```

SEQ ID NO: 47 is an exemplary amino acid sequence of a wildtype IgG1-based Fc domain.

```
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK
```

SEQ ID NO: 48 is an exemplary amino acid sequence of a mutant IgG1-based Fc domain that does not dimerized with other Fc domains.

```
APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTSPPSRDELTKNQVSLRCHVKGFYPSDIAVE

WESNGQPENNYKTTKPVLDSDGSFFLYSKLTVDKSRWQQGNVFSCSVMHE

ALHNHYTQKSLSLSPGK
```

SEQ ID NO: 49 is an exemplary amino acid sequence of a mature IGF-1 polypeptide.

SEQ ID NOs: 50-53 are exemplary amino acid and DNA sequences of parathyroid hormone proteins.

DETAILED DESCRIPTION

I. Summary of Terms

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." Thus, "comprising an antigen" means "including an antigen" without excluding other elements. It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

Achondroplasia: A cartilage disorder that results in stunted or reduced growth, commonly known as Dwarfism. Achondroplasia is usually caused by an autosomal dominant mutation in the gene for fibroblast growth factor receptor 3 (FGFR-3), which causes an abnormality of cartilage formation. FGFR-3 normally has a negative regulatory effect on chondrocyte growth, and hence bone growth. In achondroplasia, the mutated form of FGFR-3 is constitutively active, which leads to severely shortened bones. Both chondrocyte proliferation and differentiation appear to be disturbed, remarkably impairing growth at the growth plate cartilage (P. Krejci et al., J. Cell Sci. 118: 5089-5100 (2005)).

Administration: The introduction of a composition into a subject by a chosen route. Administration can be local or systemic. For example, if the chosen route is intravenous, the composition is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes. In some examples a disclosed a composition that includes a monoclonal antibody or antigen binding fragment that specifically binds matrilin-3 or conjugate thereof is administered to a subject.

Agent: Any substance or any combination of substances that is useful for achieving an end or result; for example, a substance or combination of substances useful for decreasing or reducing a cartilage disorder in a subject. Agents include effector molecules and detectable markers. In some embodiments, the agent is a chondrogenic agent. The skilled artisan will understand that particular agents may be useful to achieve more than one result; for example, an agent may be useful as both a detectable marker and a chondrogenic agent.

Antibody: An immunoglobulin, antigen-binding fragment, or derivative thereof, that specifically binds and recognizes an analyte (antigen) such as matrilin-3 or an antigenic fragment of matrilin-3. The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity.

Non-limiting examples of antibodies include, for example, intact immunoglobulins and variants and fragments thereof known in the art that retain binding affinity for the antigen. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g, Kontermann and Dubel (Ed), Antibody Engineering, Vols. 1-2, 2$^{nd}$ Ed., Springer Press, 2010).

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., *Science,* 242:423-426, 1988; Huston et al., *Proc. Natl. Acad. Sci.,* 85:5879-5883, 1988; Ahmad et al., *Clin. Dev. Immunol.,* 2012, doi:10.1155/2012/980250; Marbry, *IDrugs,* 13:543-549, 2010). The intramolecular orientation of the $V_H$-domain and the $V_L$-domain in a scFv, is typically not decisive for scFvs. Thus, scFvs with both possible arrangements ($V_H$-domain-linker domain-$V_L$-domain; $V_L$-domain-linker domain-$V_H$-domain) may be used.

In a dsFv the heavy and light chain variable chains have been mutated to introduce a disulfide bond to stabilize the association of the chains. Diabodies also are included, which are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.,* 90:6444-6448, 1993; Poljak et al., *Structure,* 2:1121-1123, 1994).

Antibodies also include genetically engineered forms such as chimeric antibodies (such as humanized murine antibodies) and heteroconjugate antibodies (such as bispecific antibodies). See also, *Pierce Catalog and Handbook,* 1994-1995 (Pierce Chemical Co., Rockford, Ill.); Kuby, J., *Immunology,* 3$^{rd}$ Ed., W.H. Freeman & Co., New York, 1997.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Typically, a naturally occurring immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, 6$^{th}$ ed., W.H. Freeman and Co., page 91 (2007).) In several embodiments, the heavy and the light chain variable regions combine to specifically bind the antigen. In additional embodiments, only the heavy chain variable region is required. For example, naturally occurring camelid antibodies consisting of a heavy chain only are functional and stable in the absence of light chain (see, e.g., Hamers-Casterman et al., *Nature,* 363:446-448, 1993; Sheriff et al., *Nat. Struct. Biol.,* 3:733-736, 1996). References to "$V_H$" or "$V_H$" refer to the variable region of an antibody heavy chain, including that of an antigen binding fragment, such as Fv, scFv, dsFv or Fab. References to "$V_L$" or "$V_L$" refer to the variable domain of an antibody light chain, including that of an Fv, scFv, dsFv or Fab.

Heavy and Light chain variable regions contain a "framework" region interrupted by three hypervariable regions, also called "complementarity-determining regions" or "CDRs" (see, e.g., Kabat et al., *Sequences of Proteins of Immunological Interest*, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, Md., 1991; "Kabat" numbering scheme), Al-Lazikani et al., (JMB 273, 927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a $V_H$ CDR3 is the CDR3 from the variable domain of the heavy chain of the antibody in which it is found, whereas a $V_L$ CDR1 is the CDR1 from the variable domain of the light chain of the antibody in which it is found. Light chain CDRs are sometimes referred to as LCDR1, LCDR2, and LCDR3. Heavy chain CDRs are sometimes referred to as LCDR1, LCDR2, and LCDR3.

A "monoclonal antibody" is an antibody obtained from a population of substantially homogeneous antibodies, that is, the individual antibodies comprising the population are identical and/or bind the same epitope, except for possible variant antibodies, for example, containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein. In some examples monoclonal antibodies are isolated from a subject. Monoclonal antibodies can have conservative amino acid substitutions which have substantially no effect on antigen binding or other immunoglobulin functions. (See, for example, Harlow & Lane, *Antibodies, A Laboratory Manual*, $2^{nd}$ ed. Cold Spring Harbor Publications, New York (2013).)

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

Anti-arthritis agent: A molecule, such as a chemical compound, small molecule, steroid, nucleic acid, polypeptide or other biological agent, that can be used to treat or inhibit arthritis in a subject. Non-limiting examples of anti-arthritis agents include immunosuppressive agents and anti-inflammatory agents.

Non-limiting examples of anti-arthritis agents that are anti-inflammatory include non-steroidal anti-inflammatory agents (e.g., ibuprofen, naproxen, COX-2 inhibitors such as celecoxib or rofecoxib) and steroidal agents (e.g, corticosteroids such as dexamethasone, prednisone, and prednisolone). Non-limiting examples of anti-arthritis agents that are immunosuppressive include steroidal agents (e.g, corticosteroids such as dexamethasone, prednisone, and prednisolone), small molecules (e.g., cyclosporine A and FK506), and biologics (e.g., TNF inhibitors such as etanercept, anti-CD4 antibodies, anti-TNFα antibodies such as adalimumab and infliximab, anti-CD20 antibodies such as rituximab, IL-1 receptor antagonists such as anakinra, and parathyroid hormone (PTH) or a fragment thereof that binds to the type 1 PTH receptor, such as PTH residues 1-34).

Some anti-arthritis agents exert their effect by reducing inflammation through inhibition of the immune system, while other anti-arthritis agents primarily exert their action through non-immune mechanisms, for example non-steroidal anti-inflammatory drugs that act through inhibition of inflammatory mediators, such as the cyclooxygenase enzyme. Anti-arthritis agents that inhibit the immune system are often used in the treatment of autoimmune arthritis. Non-steroidal anti-inflammatory drugs are often used in the treatment of both autoimmune arthritis and autoimmune arthritis, although either class of drugs can be used to inhibit inflammation in either type of arthritis.

Arthritis: Inflammation of one or more joints in a subject that occurs in various forms. Typically, the disease results from mechanical- or autoimmune-induced damage to joint tissue, which causes pain and swelling in affected areas. The joints commonly involved include the hips, knees, lower lumbar and cervical vertebrae, proximal and distal interphangeal joints of the fingers, first carpometacarpal joints, and first tarsometatarsal joints of the feet. Non-limiting types of arthritis include degenerative arthritis (e.g., osteoarthritis) and autoimmune arthritis (e.g., rheumatoid arthritis).

Rheumatoid arthritis is a chronic, systemic, inflammatory disease that typically affects the synovial membranes of multiple joints in the body. Because the disease is systemic, there are many extra-articular features of the disease as well. For example, neuropathy, scleritis, lymphadenopathy, pericarditis, splenomegaly, arteritis, and rheumatoid nodules are frequent components of the disease. In most cases of rheumatoid arthritis, the subject has remissions and exacerbations of the symptoms. Rheumatoid arthritis considered an autoimmune disease that is acquired and in which genetic factors appear to play a role.

Osteoarthritis is a degenerative joint disease frequently associated with trauma, infection, and/or age-related changes in the affected joint. The articular joint structure is degraded, leading to loss or disruption of joint cartilage and possible bone on bone contact. These changes can result in pain and diminished function. The incidence of osteoarthritis increases with age, and evidence of osteoarthritis involvement can be detected in some joints in the majority of the population by age 65. osteoarthritis is often also accompanied by a local inflammatory component that may accelerate joint destruction.

Biological sample: A sample obtained from a subject. Biological samples include all clinical samples useful for detection of disease or infection (for example, a growth disorder) in subjects, including, but not limited to, cells, tissues, and bodily fluids, such as blood, derivatives and fractions of blood (such as serum), cerebrospinal fluid; as well as biopsied or surgically removed tissue, for example tissues that are unfixed, frozen, or fixed in formalin or paraffin. In a particular example, a biological sample is obtained from a subject having or suspected of having a cartilage disorder; for example, a subject having or suspected of having short stature.

Bone Morphogenic Protein (BMP): A family of proteins belonging to the transforming growth factor-β superfamily of proteins. BMPs are proteins which act to induce the differentiation of mesenchymal-type cells into chondrocytes and osteoblasts before initiating bone formation. They promote the differentiation of cartilage- and bone-forming cells near sites of fractures but also at ectopic locations. In some embodiments, a BMP polypeptide can be conjugated to a matrilin-3 specific antibody or antigen binding fragment. BMPs can promote the conversion of fibroblasts into chondrocytes and are capable also of inducing the expression of an osteoblast phenotype in non-osteogenic cell types.

Exemplary BMP protein and nucleic acid sequences are known, and further provided herein. C-type natriuretic protein (CNP): A peptide agonist for the B-type natriuretic receptor that is known to promote growth plate chondrogenesis. In the growth plate, NPR-B is expressed by proliferative cells. In humans, CNP is initially produced from the natriuretic peptide precursor C(NPPC) gene as a single chain 126-amino acid pre-pro polypeptide. Removal of the signal peptide yields pro-CNP, and further cleavage by the endoprotease furin generates an active 53-amino acid peptide (CNP-53), which is secreted and enzymatically cleaved to produce the mature 22-amino acid peptide (CNP-22) (Wu, J. Biol. Chem. 278: 25847-852 (2003)).

Cartilage: The stiff and inflexible connective tissue found in many areas in the bodies of humans and other animals, including the joints between bones, the rib cage, the ear, the nose, the elbow, the knee, the ankle, the bronchial tubes and the intervertebral discs. Cartilage includes specialized cells called chondrocytes that produce the cartilage extracellular matrix, which includes a high proportion of collagen and proteoglycans. Non-limiting examples of cartilage include growth plate cartilage and articular cartilage.

Cartilage disorder: A condition including a cartilage defect in a subject. Cartilage disorders include, for example, growth plate cartilage disorders and articulate cartilage disorders. Non-limiting examples of growth-plate cartilage disorders include skeletal dysplasias (such as achondroplasia, hypochondroplasia, or short stature homeobox gene (SHOX) deficiency), and short stature, such as idiopathic short stature, and short stature due to systemic disease (such as systemic inflammatory diseases, renal failure, glucocorticoid therapy, or radiation damage). A non-limiting example of an articulate cartilage disorder is osteoarthritis.

Several cartilage disorders involve degradation of cartilage over time. Cartilage degradation is the catabolism or the breakdown of the cartilage, including but not limited to degradation of the extracellular matrix (including collagen, proteoglycans and aggrecans) caused by the release of abnormally high levels of degradative enzymes by the joint tissues, mainly from articular cartilage and from synovial membranes. Osteoarthritic cartilage degradation is the degradation of cartilage of the joints, including but not limited to the elbow, the knee, the hand joints (e.g. wrist, fingers, and thumb), the ankle, the foot, the hip, and the intervertebral discs and cartilage of the growth plate.

Chondrogenic agent: An agent that stimulates or promotes chondrogenesis. Non-limiting examples of chondrogenic agents include growth-regulating endocrine signaling molecules (such as growth hormone, IGF-1, estrogens, and androgens), growth-regulating paracrine signaling molecules (such as Indian Hedgehog (IHH), bone morphogenetic proteins (BMPs), C-type natriuretic peptide (CNP), WNTs, and FGFs), and steroids (such as estradiol). In several embodiments, a chondrogenic agent is conjugated to a matrilin-3 specific antibody or antigen binding fragment.

Chondrocyte: The primary cell type found in healthy cartilage. Chondrocytes produce and maintain the extracellular matrix of cartilage, including collagen and proteoglycans. Methods of identifying chondrocytes in vitro and in vivo are known, as are methods of identifying an increase or decrease in the amount of or number of chondrocytes.

Chondrogenesis: The production of cartilage. Chondrogenesis can result from, for example, increasing numbers of chondrocytes (proliferation), increasing size of chondrocytes (hypertrophy) and/or production of cartilage extracellular matrix by chondrocytes, such as an increase in cartilage extracellular matrix production by individual chondrocytes, or an increase in the number of chondrocytes producing cartilage extracellular matrix. Methods of detecting and/or quantifying chondrogenesis are known and further described herein Some of the therapeutic agents disclosed herein for treating cartilage disorders exert their therapeutic effect by stimulating chondrogenesis. The effect of stimulating chondrogenesis means a stimulation of genesis of a cartilage tissue, particularly the cartilage tissue at the epiphysis region, and is an action which also includes functional maintenance of cartilage tissues. Some of the actions are effected via any one of stimulating chondrocyte growth, stimulating chondrocyte differentiation, inhibiting cartilage calcification or inhibiting cartilage degradation, or a multiple combination thereof.

Conditions sufficient to form an immune complex: Conditions which allow an antibody or antigen binding fragment thereof to bind to its cognate epitope to a detectably greater degree than, and/or to the substantial exclusion of, binding to substantially all other epitopes. Conditions sufficient to form an immune complex are dependent upon the format of the binding reaction and typically are those utilized in immunoassay protocols or those conditions encountered in vivo. See Harlow & Lane, *Antibodies, A Laboratory Manual*, $2^{nd}$ ed. Cold Spring Harbor Publications, New York (2013) for a description of immunoassay formats and conditions. The conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The formation of an immune complex can be detected through conventional methods known to the skilled artisan, for instance immunohistochemistry, immunoprecipitation, flow cytometry, immunofluorescence microscopy, ELISA, immunoblotting (for example, Western blot), magnetic resonance imaging, CT scans, X-ray and affinity chromatography. Immunological binding properties of selected antibodies may be quantified using methods well known in the art.

Conjugate: A complex of two molecules linked together, for example, linked together by a covalent bond. In one embodiment, an antibody is linked to an effector molecule; for example, an antibody that specifically binds to matrilin-3 covalently linked to an effector molecule. The linkage can be by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because conjugates can be prepared from two molecules with separate functionalities, such as an antibody and an effector molecule, they are also sometimes referred to as "chimeric molecules."

Conservative variants: "Conservative" amino acid substitutions are those substitutions that do not substantially alter the biological function of a protein, such as substitutions that do not substantially decrease the binding affinity of an antibody for an antigen (for example, the binding affinity of an antibody for matrilin-3). For example, a human antibody that specifically binds matrilin-3 can include at most about 1, at most about 2, at most about 5, at most about 10, or at most about 15 conservative substitutions and specifically bind the matrilin-3 polypeptide. The term conservative variation also includes the use of a substituted amino acid in place of an unsubstituted parent amino acid, provided that antibody retains binding affinity for matrilin-3.

Conservative amino acid substitution tables providing functionally similar amino acids are well known to one of ordinary skill in the art. The following six groups are examples of amino acids that are considered to be conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that reduce an activity or function of the matrilin-3-specific antibody, such as the ability to specifically bind to matrilin-3. For instance, if an amino acid residue is essential for a function of the protein, even an otherwise conservative substitution may disrupt that activity. Thus, a conservative substitution does not alter the basic function of a protein of interest.

Contacting: Placement in direct physical association; includes both in solid and liquid form, which can take place either in vivo or in vitro. Contacting includes contact between one molecule and another molecule, for example the amino acid on the surface of one polypeptide, such as an antigen, that contacts another polypeptide, such as an antibody. Contacting can also include contacting a cell for example by placing an antibody in direct physical association with a cell.

Control: A reference standard. In some embodiments, the control is a negative control, such as tissue sample obtained from a patient that does not have a cartilage disorder, or a tissue sample from a tissue that is not affected by the cartilage disorder. In other embodiments, the control is a positive control, such as a tissue sample obtained from a patient diagnosed with a cartilage disorder, or a tissue sample from a tissue affected by the cartilage disorder. In still other embodiments, the control is a historical control or standard reference value or range of values (such as a previously tested control sample, such as from group of cartilage disorder patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, or at least about 500%.

Degenerate variant: In the context of the present disclosure, a "degenerate variant" refers to a polynucleotide encoding a protein (for example, an antibody that specifically binds matrilin-3) that includes a sequence that is degenerate as a result of the genetic code. There are twenty natural amino acids, most of which are specified by more than one codon. Therefore, all degenerate nucleotide sequences are included as long as the amino acid sequence of the antibody that binds matrilin-3 encoded by the nucleotide sequence is unchanged.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (such as $^{35}S$ or $^{131}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance. Methods for using detectable markers and guidance in the choice of detectable markers appropriate for various purposes are discussed for example in Sambrook et al. (Molecular Cloning: A Laboratory Manual, $4^{th}$ ed, Cold Spring Harbor, N.Y., 2012) and Ausubel et al. (In Current Protocols in Molecular Biology, John Wiley & Sons, New York, through supplement 104, 2013).

Detecting: To identify the existence, presence, or fact of something. General methods of detecting are known to the skilled artisan and may be supplemented with the protocols and reagents disclosed herein. For example, included herein are methods of detecting cartilage, such as growth-plate cartilage, in a subject.

Effector molecule: A molecule intended to have or produce a desired effect; for example, a desired effect on a cell to which the effector molecule is targeted. Effector molecules can include, for example, polypeptides and small molecules. In one non-limiting example, the effector molecule is a chondrogenic agent. The skilled artisan will understand that some effector molecules may have or produce more than one desired effect. In one example, an effector molecule is the portion of a chimeric molecule, for example a chimeric molecule that includes a disclosed antibody or fragment thereof, that is intended to have a desired effect on a cell or tissue to which the chimeric molecule is targeted.

Epitope: An antigenic determinant. These are particular chemical groups or peptide sequences on a molecule that are antigenic, i.e. that elicit a specific immune response. An antibody specifically binds a particular antigenic epitope on a polypeptide. In some examples a disclosed antibody specifically binds to an epitope on matrilin-3.

Expressed: Translation of a nucleic acid into a protein. Proteins may be expressed and remain intracellular, become a component of the cell surface membrane, or be secreted into the extracellular matrix or medium.

Expression Control Sequences: Nucleic acid sequences that regulate the expression of a heterologous nucleic acid sequence to which it is operatively linked Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Fc polypeptide: The polypeptide including the constant region of an antibody excluding the first constant region immunoglobulin domain. Fc region generally refers to the last two constant region immunoglobulin domains of IgA, IgD, and IgG, and the last three constant region immunoglobulin domains of IgE and IgM. An Fc region may also include part or all of the flexible hinge N-terminal to these domains. For IgA and IgM, an Fc region may or may not include the tailpiece, and may or may not be bound by the J chain. For IgG, the Fc region includes immunoglobulin domains Cgamma2 and Cgamma3 (C$\gamma$2 and C$\gamma$3) and the lower part of the hinge between Cgamma1 (C$\gamma$1) and C$\gamma$2. Although the boundaries of the Fc region may vary, the human IgG heavy chain Fc region is usually defined to include residues C226 or P230 to its carboxyl-terminus, wherein the numbering is according to the EU index as in Kabat. For IgA, the Fc region includes immunoglobulin domains Calpha2 and Calpha3 (C$\alpha$2 and C$\alpha$3) and the lower part of the hinge between Calpha1 (C$\alpha$1) and C$\alpha$2. In some embodiments, the Fc can be a mutant IgG Fc domain that does not dimerize under physiological conditions, for example, an Fc domain comprising the amino acid sequence set forth as SEQ ID NO: 48.

Framework Region: Amino acid sequences interposed between CDRs in a heavy or light variable region of an antibody. Includes variable light and variable heavy framework regions. The framework regions serve to hold the CDRs in an appropriate orientation.

Growth Plate: A specialized cartilage structure present near the ends of tubular bones and vertebrae, and which includes chondrocytes that produce cartilage extracellular matrix. The primary function of the growth plate is to generate new cartilage, which is then remodeled into bone tissue, resulting in bone elongation. Because body length is largely determined by the lengths of long bones and vertebrae, bone formation at the growth plates is the underlying mechanism responsible for increasing height during childhood. In addition to genetic disorders, acquired endocrine, nutritional, or inflammatory disorders also impair bone growth at the growth plate, resulting in short stature. Some of the more common acquired conditions that inhibit childhood growth include renal failure, inflammatory bowel disease, glucocorticoid therapy such as prednisone, or radiation therapy.

There are three principal zones of the growth plate: resting, proliferative, and hypertrophic. In normal endochondral bone growth, chondrocytes organize in columns and proliferate in the proliferative zone of the growth plate. The hypertrophic zone is where the cells become large and eventually undergo apoptosis (programmed cell death). The hypertrophic zone is invaded by blood vessels, osteoclasts, and differentiating osteoblasts which remodel the newly formed cartilage into bone tissue. Impaired proliferation, differentiation, or function of the growth plate chondrocytes in these zones of the growth plate can lead to a growth plate cartilage disorder, for example, achondroplasia.

Longitudinal bone growth at the growth plate is a complex process which requires multiple intracellular, endocrine, and paracrine pathways to function normally. Consequently, mutations in hundreds of genes that are required for growth plate function give rise to disorders of skeletal growth, including skeletal dysplasias, in which the bones are typically short and malformed, often causing major disability.

Increase: To increase the quality, amount, or strength of something; for example an increase in the size or volume of cartilage (such as growth plate cartilage or articulate cartilage), to increase the number or amount or production of chondrocytes in cartilage tissue (such as growth plate or articular cartilage). In a particular example, a therapy increases in the size or volume of cartilage (such as growth plate cartilage or articulate cartilage), the number or amount or production of chondrocytes in cartilage tissue (such as growth plate or articular cartilage), and/or the linear growth of a subject, subsequent to the therapy, such as an increase of at least 10%, at least 20%, at least 30%, at least 40%, at least 50%, at least 60%, at least 70%, at least 80%, or at least 90%. Such increases can be measured using known methods and those disclosed herein.

Isolated: A biological component (such as a nucleic acid, peptide, protein or protein complex, for example an antibody) that has been substantially separated, produced apart from, or purified away from other biological components in the cell of the organism in which the component naturally occurs, that is, other chromosomal and extra-chromosomal DNA and RNA, and proteins. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. A isolated nucleic acid, peptide or protein, for example an antibody, can be at least 50%, at least 60%, at least 70%, at least 80%, at least 90%, at least 95%, at least 96%, at least 97%, at least 98%, or at least 99% pure.

$K_D$: The dissociation constant for a given interaction, such as a polypeptide ligand interaction or an antibody antigen interaction. For example, for the bimolecular interaction of an antibody or antigen binding fragment (such as a matrilin-3 specific antibody or conjugate thereof) and an antigen (such as matrilin-3 protein) it is the concentration of the individual components of the bimolecular interaction divided by the concentration of the complex.

Linear Growth: An increase in the long bones of a subject. In humans, an increase in linear growth correlates with an increase in height, and can be identified, for example, by detecting an increase in the height of a human subject over time. In several non-human subjects (e.g., murine subjects), an increase in linear growth can be identified by detecting an increase in the length of a long bone in the subject (e.g., the femur) or in body length over time.

Linker: A bi-functional molecule that can be used to link two molecules into one contiguous molecule, for example, to link an effector molecule to an antibody. In some embodiments, the provided conjugates include a linker between the effector molecule or detectable marker and an antibody. In some cases, a linker is a peptide within an antigen binding fragment (such as an Fv fragment) which serves to indirectly bond the variable heavy chain to the variable light chain. Non-limiting examples of peptide linkers include a (GGGGS)$_1$ (SEQ ID NO: 38), (GGGGS)$_2$ (SEQ ID NO: 39), or a (GGGGS)$_3$ (SEQ ID NO: 40) linker.

The terms "conjugating," "joining," "bonding," or "linking" can refer to making two molecules into one contiguous molecule; for example, linking two polypeptides into one contiguous polypeptide, or covalently attaching an effector molecule or detectable marker radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Matrilin-3: A member of the non-collagenous matrilin family of extracellular matrix proteins that share common domains and similar functions. Matrilin-3 is expressed primarily in cartilage and mutations in the gene encoding matrilin-3 protein can result in a variety of skeletal diseases including chondrodysplasia and osteoarthritis. Exemplary protein and nucleic acid sequences for human matrilin-3 precursor are set forth as SEQ ID NOs: 16 and 17, respectively (NCBI Acc. Nos. NP_002372.1 and NM_002381.4, incorporated by reference herein as present in the database on Dec. 1, 2013).

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Osteoarthritis: A disorder caused by gradual degradation of articular cartilage with inadequate repair, which affects 30-50% of older adults. In patients with osteoarthritis, the cartilage extracellular matrix proteins, which are the functional entity of the cartilage, are reduced, and the number of chondrocytes decreases (Aigner and Kim, Arth. Rheum. 46(8): 1986-1996 (2002)). Methods of identifying a subject with osteoarthritis are known; see, e.g., Moskowitz et al. (Eds), Osteoarthritis: Diagnosis and Medical/Surgical Management, Lippincott Williams & Wilkins; Fourth edition, 2006.

Pharmaceutically acceptable carriers: The pharmaceutically acceptable carriers provided herein are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, added preservatives (such as non-natural preservatives), and pH buffering agents and the like, for example sodium acetate or sorbitan monolaurate. In particular examples, the pharmaceutically acceptable carrier is sterile and suitable for parenteral administration, for example by injection. In some embodiments, the active agent and pharmaceutically acceptable carrier are provided in a unit dosage form such as a pill or in a selected quantity in a vial. Unit dosage forms can include one dosage or multiple dosages (for example, in a vial from which metered dosages of the agents can selectively be dispensed).

Polypeptide: Any chain of amino acids, regardless of length or post-translational modification (e.g., glycosylation or phosphorylation). In one embodiment, the polypeptide is a disclosed antibody or a fragment thereof. A "residue" refers to an amino acid or amino acid mimetic incorporated in a polypeptide by an amide bond or amide bond mimetic. A polypeptide has an amino terminal (N-terminal) end and a carboxy terminal (C-terminal) end.

Polypeptide modifications: Peptides can be modified by a variety of chemical techniques to produce derivatives having essentially the same activity and conformation as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains can be converted to $C_1$-$C_{16}$ alkoxy or to a $C_1$-$C_{16}$ ester using well-recognized techniques. Phenyl and phenolic rings of the peptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups.

Purified: The term purified does not require absolute purity; rather, it is intended as a relative term. Thus, for example, a purified peptide preparation is one in which the peptide or protein (such as an antibody) is more enriched than the peptide or protein is in its natural environment within a cell. In one embodiment, a preparation is purified such that the protein or peptide represents at least 50% of the total peptide or protein content of the preparation, such as at least 80%, at least 90%, at least 95% or greater of the total peptide or protein content.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques. A recombinant protein is a protein encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Sambrook et al. (Molecular Cloning: A Laboratory Manual, 4$^{th}$ ed, Cold Spring Harbor, N.Y., 2012) and Ausubel et al. (In Current Protocols in Molecular Biology, John Wiley & Sons, New York, through supplement 104, 2013). One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989). An oligonucleotide is a linear polynucleotide sequence of up to about 100 nucleotide bases in length.

Short stature: A height that is below the normal range either during childhood or adulthood. In some embodiments, a subject with short stature is one with a height that is less than two standard deviations below the mean height for comparable age and sex. The person of ordinary skill in the art can readily determine if a particular subject is a subject with short stature.

Specifically bind: When referring to an antibody or antigen binding fragment thereof, refers to a binding reaction which determines the presence of a target protein, peptide, or polysaccharide in the presence of a heterogeneous population of proteins and other biologics. Thus, under designated conditions, an antibody binds preferentially to a particular target protein, peptide or polysaccharide (such as an epitope of matrilin-3) and does not bind in a significant amount to other proteins or polysaccharides present in the sample or subject. Specific binding can be determined by methods known in the art. With reference to an antibody antigen complex, specific binding of the antigen and antibody has a $K_d$ of less than about $10^{-7}$ Molar (M), such as less than about $10^{-8}$ M, $10^{-9}$ M, $10^{-10}$ M, or even less than about $10^{-11}$ M.

Particular antibodies disclosed herein specifically bind only to a defined target (or multiple targets, in the case of a bispecific antibody). Thus, an antibody that specifically binds to matrilin-3 is an antibody that binds substantially to matrilin-3, including cells or tissue expressing matrilin-3, substrate to which the matrilin-3 is attached, or matrilin-3 in a biological specimen. It is, of course, recognized that a certain degree of non-specific interaction may occur between an antibody or conjugate including an antibody (such as an antibody that specifically binds matrilin-3 or conjugate including such antibody) and a non-target (such as a cell that does not express matrilin-3). Typically, specific binding results in a much stronger association between the antibody and protein or cells bearing the antigen than between the antibody and protein or cells lacking the antigen. Specific binding typically results in greater than 2-fold, such as greater than 5-fold, greater than 10-fold, or greater than 100-fold increase in amount of bound antibody (per unit time) to a protein including the epitope or cell or tissue expressing the target epitope as compared to a protein or cell or tissue lacking this epitope. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, 2nd ed., Cold Spring Harbor Publications, New York (2013), for a description of immunoassay formats and conditions that can be used to determine specific immunoreactivity.

Subject: Any mammal, such as humans, non-human primates, pigs, sheep, cows, rodents, and the like. In two non-limiting examples, a subject is a human subject or a murine subject. Thus, the term "subject" includes both human and veterinary subjects.

Therapeutic agent: Used in a generic sense, it includes treating agents, prophylactic agents, and replacement agents. A therapeutic agent is used to ameliorate a specific set of conditions in a subject with a disease or a disorder.

Therapeutically effective amount: The amount of an agent (such as a matrilin-3 specific antibody or antigen binding fragment, conjugate thereof, or nucleic acid molecule encoding such molecules) that alone, or together with one or more additional agents, induces the desired response, such as treatment of a cartilage disorder in a subject. Ideally, a therapeutically effective amount provides a therapeutic effect without causing a substantial cytotoxic effect in the subject. In some embodiments, a desired response is to increase the size or volume of cartilage (such as growth plate cartilage or articulate cartilage), to increase the number or amount or production of chondrocytes in cartilage tissue (such as growth plate or articular cartilage). For example, the agent or agents can increase the size or volume of cartilage (such as growth plate cartilage or articulate cartilage), or the number or amount or production of chondrocytes in cartilage tissue (such as growth plate or articular cartilage) by a desired amount, for example by at least 5%, at least 10%, at least 15%, at least 20%, at least 25%, at least 30%, at least 50%, at least 75%, at least 90%, or at least 95% as compared to a response in the absence of the agent. In additional examples, the agent or agents can increase the linear growth of a subject by a desired amount, for example by at least 5%, at least 10%, at least 15%, at least 20%, at least 25%, at least 30%, at least 50%, at least 75%, at least 90%, or at least 95% as compared to a response in the absence of the agent.

In some embodiments, a therapeutically effective amount of a conjugate including a matrilin-3 specific antibody or antigen binding fragment linked to a chondrogenic agent induces proliferation and differentiation of chondrocytes, for example to produce an increase in the size or volume of growth plate cartilage tissue in a subject.

Several preparations disclosed herein are administered in therapeutically effective amounts. A therapeutically effective amount of an antibody that specifically binds matrilin-3 or matrilin-3 binding fragment thereof, or conjugate thereof (or a composition including one or more of these molecules) that is administered to a human or veterinary subject will vary depending upon a number of factors associated with that subject, for example the overall health of the subject. A therapeutically effective amount can be determined by varying the dosage and measuring the resulting therapeutic response, such as, for example, an increase in production of chondrocytes or an increase in linear growth of the subject. Therapeutically effective amounts also can be determined through various in vitro, in vivo or in situ immunoassays. The disclosed agents can be administered in a single dose, or in several doses, as needed to obtain the desired response. However, the therapeutically effective amount of can be dependent on the source applied, the subject being treated, the severity and type of the condition being treated, and the manner of administration.

Transformed: A transformed cell is a cell into which a nucleic acid molecule has been introduced by molecular biology techniques. As used herein, the term transformation encompasses all techniques by which a nucleic acid molecule might be introduced into such a cell, including transfection with viral vectors, transformation with plasmid vectors, and introduction of DNA by electroporation, lipofection, and particle gun acceleration.

Treating or preventing a disease or condition: Inhibiting the full development of a disease or condition, for example, in a subject who is at risk of or has a disease such as a cartilage disorder and/or arthritis. "Treatment" refers to a therapeutic intervention (for example, administration of a therapeutically effective amount of a conjugate including an antibody or antigen binding fragment that specifically binds matrilin-3 linked to a chondrogenic agent) that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology. In particular examples, treatment includes preventing a cartilage disorder, for example by inhibiting the full development of a cartilage disorder. Prevention does not require a total absence of the cartilage disorder.

Reducing a sign or symptom of a disease or pathological condition related to a disease, refers to any observable beneficial effect of the treatment. Reducing a sign or symptom associated with a cartilage disorder can be evidenced, for example, by a delayed onset of clinical symptoms of the disease in a susceptible subject, a reduction in severity of some or all clinical symptoms of the disease (such as an increase in linear growth of the subject), a slower progression of the disease (for example by prolonging the life of a subject having cartilage disorder), an improvement in the overall health or well-being of the subject, or by other parameters well known in the art that are specific to the particular cartilage disorder. Reducing a sign or symptom associated with arthritis can be evidenced, for example, by a delayed onset of clinical symptoms of the disease in a susceptible subject, a reduction in severity of some or all clinical symptoms of the disease (such as a decrease in pain or swelling due to the condition in the subject), a slower progression of the disease, an improvement in the overall health or well-being of the subject, or by other parameters well known in the art that are specific to the particular type of arthritis. A "prophylactic" treatment is a treatment administered to a subject who does not exhibit signs of a disease or exhibits only early signs for the purpose of decreasing the risk of developing pathology.

Thus, a therapeutic agent as disclosed herein (such as a conjugate comprising a matrilin-3 specific antibody or antigen binding fragment linked to a chondrogenic agent such as IGF-1) that reduces or prevents a cartilage disorder and/or arthritis, can, but does not necessarily completely, eliminate such disorder, so long as the disorder or its symptoms are measurably diminished, for example, by at least about 50%, such as by at least about 70%, or about 80%, or even by about 90% the infection in the absence of the agent, or in comparison to a reference agent.

Under conditions sufficient for: A phrase that is used to describe any environment that permits a desired activity. In one example the desired activity is formation of an immune complex. In particular examples the desired activity is treatment of a growth disorder.

Vector: A nucleic acid molecule as introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses. A replication deficient viral vector is a vector that requires complementation of one or more regions of the viral genome required for replication due to a deficiency in at least one replication-essential gene function. For example, such that the viral vector does not replicate in typical host cells, especially those in a human patient that could be infected by the viral vector in the course of a therapeutic method.

II. Description of Several Embodiments

A. Antibodies and Antigen Binding Fragments

Isolated monoclonal antibodies and antigen binding fragments thereof that specifically bind an epitope on matrilin-3 are provided. The antibodies can be fully human. In several embodiments the antibodies and antigen binding fragments specifically bind to matrilin-3 in the cartilage extracellular matrix. In additional embodiments, the antibodies and antigen binding fragments specifically bind to matrilin-3 in the extracellular matrix of growth-plate cartilage.

In some embodiments, the antibodies and antigen binding fragments include a variable heavy ($V_H$) and a variable light ($V_L$) chain and specifically bind matrilin-3. In several embodiments, the antibodies and antigen binding fragments include a heavy chain comprising a heavy chain complementarity determining region (HCDR)1, a HCDR2 and an HCDR3, and a light chain comprising a light chain complementarity determining region (LCDR) 1, a LCDR2, and a LCDR3 and specifically bind to matrilin-3. In several embodiments, the antibody or antigen binding fragment includes heavy and light chain variable regions including the HCDR1, HCDR2, and HCDR3, and LCDR1, LCDR2, and LCDR3, respectively, of one of the matrilin-3 specific clone 13, 22, or 26 antibodies, and specifically bind to matrilin-3.

The discussion of monoclonal antibodies below refers to isolated monoclonal antibodies and antigen binding fragments that include heavy and light chain variable domains including at least one complementarity determining region (CDR), such as a CDR1, CDR2 and CDR3. The person of ordinary skill in the art will understand that various CDR numbering schemes (such as the Kabat, Chothia or IMGT numbering schemes) can be used to determine CDR positions. The amino acid sequence and the CDR positions of the heavy and light chain of the matrilin-3 antibodies (such as the clone 13, 22, and 26 antibodies) according to the IMGT numbering scheme is shown in Table 1 (IMGT). The person of skill in the art will readily understand use of various CDR numbering schemes (such as the Kabat numbering scheme) when referencing particular amino acids of the antibodies disclosed herein.

TABLE 1

IMGT CDR sequences of matrilin-3 specific antibodies

Clone 13

| | SEQ ID NO: 1 A.A. Sequence | | | SEQ ID NO: 2 A.A. Sequence | |
|---|---|---|---|---|---|
| HCDR1 | 26-33 | GGTFSSYA | LCDR1 | 27-32 | QDISNY |
| HCDR2 | 51-58 | IIPIFGTA | LCDR2 | 50-52 | DAS |
| HCDR3 | 97-106 | ARGQGYWFDP | LCDR3 | 89-97 | QQYDNLPLT |

Clone 22

| | SEQ ID NO: 3 A.A. Sequence | | | SEQ ID NO: 4 A.A. Sequence | |
|---|---|---|---|---|---|
| HCDR1 | 26-33 | GDSVSSNS | LCDR1 | 26-31 | SLRSYY |
| HCDR2 | 53-61 | TYYGSKWYN | LCDR2 | 49-51 | DRD |
| HCDR3 | 100-109 | TRGIWNAFDI | LCDR3 | 88-97 | QSYDTSLSWV |

Clone 26

| | SEQ ID NO: 5 A.A. Sequence | | | SEQ ID NO: 6 A.A. Sequence | |
|---|---|---|---|---|---|
| HCDR1 | 26-33 | GGTFSSYA | LCDR1 | 26-33 | SSNIGSNA |
| HCDR2 | 51-58 | IIPILGIA | LCDR2 | 51-53 | SNN |
| HCDR3 | 97-108 | ARWGSGSHAFDI | LCDR3 | 90-100 | AAWDDSLNGWV |

In some embodiments, the antibody or antigen binding fragment includes IMGT CDRs, such as those listed in Table 1. For example, in some embodiments, the antibody or antigen binding fragment includes a heavy chain variable region including a HCDR1, HCDR2, and/or HCDR3 including amino acids amino acids 26-33, 51-58, and 97-106 of SEQ ID NO: 1, respectively. In further embodiments, the antibody or antigen binding fragment includes a heavy chain variable region including a HCDR1, HCDR2, and/or HCDR3 including amino acids amino acids 26-33, 53-61, and 100-109 of SEQ ID NO: 3, respectively. In additional embodiments, the antibody or antigen binding fragment includes a heavy chain variable region including a HCDR1, HCDR2, and/or HCDR3 including amino acids 26-33, 51-58, 97-108 of SEQ ID NO: 5, respectively.

In some embodiments, the antibody or antigen binding fragment includes a light chain variable region including a LCDR1, LCDR2, and/or LCDR3 including amino acids 27-32, 50-52, and 89-97 of SEQ ID NO: 2, respectively. In further embodiments, the antibody or antigen binding fragment includes a light chain variable region including a LCDR1, LCDR2, and/or LCDR3 including amino acids 26-31, 49-51, and 88-97 of SEQ ID NO: 4, respectively. In additional embodiments, the antibody or antigen binding fragment includes a light chain variable region including a LCDR1, LCDR2, and/or LCDR3 including amino acids 26-33, 51-53, and 90-100 of SEQ ID NO: 6, respectively.

In some embodiments, the antibody or antigen binding fragment includes a heavy chain variable region including a HCDR1, HCDR2, and HCDR3 including amino acids 26-33, 51-58, and 97-106 of SEQ ID NO: 1, respectively, and a light chain variable region including a LCDR1, LCDR2, and LCDR3 including amino acids 27-32, 50-52, and 89-97 of SEQ ID NO: 2, respectively. In further embodiments, the antibody or antigen binding fragment includes a heavy chain variable region including a HCDR1, HCDR2, and HCDR3 including amino acids 26-33, 53-61, and 100-109 of SEQ ID NO: 3, respectively, and a light chain variable region including a LCDR1, LCDR2, and LCDR3 including amino acids 26-31, 49-51, and 88-97 of SEQ ID NO: 4, respectively. In additional embodiments, the antibody or antigen binding fragment includes a heavy chain variable region including a HCDR1, HCDR2, and HCDR3 including amino acids 26-33, 51-58, 97-108 of SEQ ID NO: 5, respectively, and a light chain variable region including a LCDR1, LCDR2, and LCDR3 including amino acids 26-33, 51-53, and 90-100 of SEQ ID NO: 6, respectively.

In some embodiments, the antibody or antigen binding fragment includes a heavy chain variable region including an amino acid sequence at least 80%, 90%, 95%, 96%, 97%, 98%, or 99% identical to the amino acid sequence set forth as one of SEQ ID NO: 1, 3, or 5. In some embodiments, the antibody or antigen binding fragment further includes at least one amino acid substation compared to SEQ ID NO: 1, 3, or 5. In more embodiments, the antibody or antigen binding fragment includes a light chain variable region including an amino acid sequence at least 80%, 90%, 95%, 96%, 97%, 98%, or 99% identical to the amino acid sequence set forth as one of SEQ ID NO: 2, 4, or 6. In some embodiments, the antibody or antigen binding fragment further includes at least one amino acid substation compared to SEQ ID NO: 1, 3, or 5.

In additional embodiments, the antibody or antigen binding fragment includes a heavy chain variable region including the amino acid sequence set forth as one of SEQ ID NO: 1, 3, or 5. In more embodiments, the antibody or antigen binding fragment includes a light chain variable region including the amino acid sequence set forth as one of SEQ ID NO: 2, 4, or 6.

In additional embodiments, the antibody includes a heavy chain variable region including a HCDR1, a HCDR2, and a HCDR3 including amino acid sequences at least 80% (such as at least 90%, 95%, 96%, 97%, 98%, or 99%) identical to amino acids 26-33, 51-58, and/or 97-106, respectively, of SEQ ID NO: 1, and a light chain variable region including a LCDR1, a LCDR2, and a LCDR3 including amino acid sequences at least 80% (such as at least 90%, 95%, 96%, 97%, 98%, or 99%) identical to amino acids amino acids 27-32, 50-52, and/or 89-97, respectively, of SEQ ID NO: 2. In some such embodiments, the antibody or antigen binding fragment further includes at least one amino acid substation compared to SEQ ID NO: 1 or SEQ ID NO: 2. In additional embodiments, the antibody includes a heavy chain variable region including a HCDR1, a HCDR2, and a HCDR3 including amino acid sequences at least 80% (such as at least 90%, 95%, 96%, 97%, 98%, or 99%) identical to amino acids 26-33, 53-61, and/or 100-109, respectively, of SEQ ID NO: 3, and a light chain variable region including a LCDR1, a LCDR2, and a LCDR3 including amino acid sequences at least 80% (such as at least 90%, 95%, 96%, 97%, 98%, or 99%) identical to amino acids amino acids 26-31, 49-51, and/or 88-97, respectively, of SEQ ID NO: 4. In some such embodiments, the antibody or antigen binding fragment further includes at least one amino acid substation compared to SEQ ID NO: 3 or SEQ ID NO: 4. In additional embodiments, the antibody includes a heavy chain variable region including a HCDR1, a HCDR2, and a HCDR3 including amino acid sequences at least 80% (such as at least 90%, 95%, 96%, 97%, 98%, or 99%) identical to amino acids 26-33, 51-58, and/or 97-108, respectively, of SEQ ID NO: 5, and a light chain variable region including a LCDR1, a LCDR2, and a LCDR3 including amino acid sequences at least 80% (such as at least 90%, 95%, 96%, 97%, 98%, or 99%) identical to amino acids amino acids 26-33, 51-53, and/or 90-100, respectively, of SEQ ID NO: 6. In some such embodiments, the antibody or antigen binding fragment further includes at least one amino acid substation compared to SEQ ID NO: 5 or SEQ ID NO: 6.

In additional embodiments, the antibody or antigen binding fragment includes a heavy chain variable region including an amino acid sequence at least 80%, 90%, 95%, 96%, 97%, 98%, or 99% identical to the amino acid sequence set forth as SEQ ID NO: 1, and a light chain variable region including an amino acid sequence at least 80%, 90%, 95%, 96%, 97%, 98%, or 99% identical to the amino acid sequence set forth as SEQ ID NO: 2. In additional embodiments, the antibody or antigen binding fragment includes a heavy chain variable region including an amino acid sequence at least 80%, 90%, 95%, 96%, 97%, 98%, or 99% identical to the amino acid sequence set forth as SEQ ID NO: 3, and a light chain variable region including an amino acid sequence at least 80%, 90%, 95%, 96%, 97%, 98%, or 99% identical to the amino acid sequence set forth as SEQ ID NO: 4. In additional embodiments, the antibody or antigen binding fragment includes a heavy chain variable region including an amino acid sequence at least 80%, 90%, 95%, 96%, 97%, 98%, or 99% identical to the amino acid sequence set forth as SEQ ID NO: 5, and a light chain variable region including an amino acid sequence at least 80%, 90%, 95%, 96%, 97%, 98%, or 99% identical to the amino acid sequence set forth as SEQ ID NO: 6.

In some embodiments, the antibody or antigen binding fragment includes a heavy chain variable region and a light chain variable region including the amino acid sequences set forth as SEQ ID NOs: 1 and 2, respectively. In some embodiments, the antibody or antigen binding fragment includes a heavy chain variable region and a light chain variable region including the amino acid sequences set forth as SEQ ID NOs: 3 and 4, respectively. In some embodiments, the antibody or antigen binding fragment includes a heavy chain variable region and a light chain variable region including the amino acid sequences set forth as SEQ ID NOs: 5 and 6, respectively.

In several embodiments, the antibody or antigen binding fragment can specifically bind matrilin-3 with an affinity of at least about $1.0 \times 10^{-8}$ M, at least about $5.0 \times 10^{-8}$ M, at least about $1.0 \times 10^{-9}$ M, at least about $5.0 \times 10^{-9}$ M, at least about $1.0 \times 10^{-10}$ M, at least about $5.0 \times 10^{-10}$ M, or at least about $1.0 \times 10^{-11}$ M.

The antibody or antigen binding fragment can be a human antibody or fragment thereof. Chimeric antibodies are also provided. The antibodies and fragments can include any suitable framework region, such as (but not limited to) a human framework region. Human framework regions, and mutations that can be made in human framework regions, are known in the art (see, for example, in U.S. Pat. No. 5,585,089, which is incorporated herein by reference). Alternatively, a heterologous framework region, such as, but not limited to a mouse framework region, can be included in the heavy or light chain of the antibodies. (See, for example, Jones et al., *Nature* 321:522, 1986; Riechmann et al., *Nature* 332:323, 1988; Verhoeyen et al., *Science* 239:1534, 1988; Carter et al., *Proc. Natl. Acad. Sci. U.S.A.* 89:4285, 1992; Sandhu, *Crit. Rev. Biotech.* 12:437, 1992; and Singer et al., *J. Immunol.* 150:2844, 1993.)

In some embodiments, the antibody or antigen binding fragment can include from up to 10 amino acid substitutions (such as up to 1, 2, 3, 4, 5, 6, 7, 8, or up to 9 amino acid substitutions) in the framework regions of the heavy chain of the antibody, or the light chain of the antibody, or the heavy and light chains of the antibody, compared to a known framework region, or compared to the framework regions of the clone 13, 22, or 26 antibodies, and maintain specific binding activity for matrilin-3.

In several embodiments, the antibody or antigen binding fragment includes at least one amino acid substitution (such as in one or more of the framework regions or the CDRs) compared to a naturally occurring antibody. In some embodiments, the antibody or antigen binding fragment includes at least one amino acid substitution (such as in one or more of the framework regions or the CDRs) compared to one of the clone 13, 22, or 26 antibodies as described herein.

The antibody or antigen binding fragment can be derivatized or linked to another molecule (such as another peptide or protein). In general, the antibody or antigen binding fragment is derivatized such that the binding to matrilin-3 is not affected adversely by the derivatization or labeling. For example, the antibody or antigen binding fragment can be functionally linked (by chemical coupling, genetic fusion, noncovalent association or otherwise) to one or more other molecular entities, such as another antibody (for example, a bi-specific antibody or a diabody), a detectable marker, an effector molecule, or a protein or peptide that can mediate association of the antibody or antibody portion with another molecule (such as a streptavidin core region or a polyhistidine tag).

One type of derivatized antibody is produced by cross-linking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company, Rockford, Ill.

The monoclonal antibodies disclosed herein can be of any isotype. The monoclonal antibody can be, for example, an IgM or an IgG antibody, such as $IgG_1$, $IgG_2$, $IgG_3$, or an $IgG_4$. However, in other embodiments, the disclosed monoclonal antibodies are not an IgG. The class of an antibody that specifically binds matrilin-3 can be switched with another (for example, IgG can be switched to IgM), according to well-known procedures. For example, a nucleic acid molecule encoding the $V_L$ or $V_H$ of a disclosed antibody can be operatively linked to a nucleic acid sequence encoding a $C_L$ or $C_H$ from a different class of immunoglobulin molecule. This can be achieved using a vector or nucleic acid molecule that comprises a $C_L$ or $C_H$ chain, as known in the art. For example, an antibody that specifically binds matrilin-3, that was originally IgG may be class switched to an IgM. Class switching can be used to convert one IgG subclass to another, such as from $IgG_1$ to $IgG_2$, $IgG_3$, or $IgG_4$.

In some examples, the disclosed antibodies or antigen binding fragments are oligomers, such as dimers, trimers, tetramers, pentamers, hexamers, septamers, octomers and so on. In some examples, the antibodies or fragments are pentamers.

In several embodiments, the constant region of the antibody includes one or more amino acid substitutions to optimize in vivo half-life of the antibody. The serum half-life of IgG Abs can be regulated by the neonatal Fc receptor (FcRn). Thus, in several embodiments, the antibody includes an amino acid substitution that increases binding to the FcRn. Several such substitutions are known to the person of ordinary skill in the art, such as substitutions at IgG constant regions T250Q and M428L (see, e.g., Hinton et al., *J Immunol.*, 176:346-356, 2006); M428L and N434S (see, e.g., Zalevsky, et al., *Nature Biotechnology*, 28:157-159, 2010); N434A (see, e.g., Petkova et al., *Int. Immunol.*, 18:1759-1769, 2006); T307A, E380A, and N434A (see, e.g., Petkova et al., *Int. Immunol.*, 18:1759-1769, 2006); and M252Y, S254T, and T256E (see, e.g., Dall'Acqua et al., *J. Biol. Chem.*, 281:23514-23524, 2006).

In some embodiments, the constant region of the antibody includes one of more amino acid substitutions to reduce Antibody-dependent cell-mediated cytotoxicity (ADCC). ADCC is mediated primarily through a set of closely related Fcγ receptors. In other embodiments, the antibody include one or more amino acid substitutions to decrease binding to FcγRIIIa.

Combinations of the above substitutions are also included, to generate an IgG constant region with increased binding to FcRn and decreased binding to FcγRIIIa. The combinations can, for example, increase antibody half-life and decrease ADCC.

Antigen binding fragments of the antibodies that specifically bind to matrilin-3 are also encompassed by the present disclosure, such as single-domain antibodies (for example, $V_H$ domain antibodies), Fab, F(ab')$_2$, scFv, and Fv. These antigen binding fragments retain the ability to specifically bind matrilin-3. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the variable region of the light chain and the variable region of the heavy chain expressed as two chains;

(5) Single chain antibody (such as scFv), a genetically engineered molecule containing the variable region of the light chain, the variable region of the heavy chain, linked by a suitable polypeptide linker as a genetically fused single chain molecule;

(6) A dimer of a single chain antibody (scFV$_2$), defined as a dimer of a scFV (also known as a "mini-antibody"); and (7) $V_H$ single-domain antibody, an antigen binding fragment consisting of the heavy chain variable domain.

Methods of making these fragments are known in the art (see for example, Harlow and Lane, *Antibodies: A Laboratory Manual*, 2$^{nd}$, Cold Spring Harbor Laboratory, New York, 2013).

In some embodiments, the antigen binding fragments are Fv antibodies, which are typically about 25 kDa and contain a complete antigen-binding site with three CDRs per each heavy chain and each light chain. To produce these antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker Thus, in one example, the Fv can be a disulfide stabilized Fv (dsFv), wherein the heavy chain variable region and the light chain variable region are chemically linked by disulfide bonds.

In an additional example, the Fv fragments include $V_H$ and $V_L$ chains connected by a peptide linker. These single-chain antigen binding proteins (scFv) can be prepared by constructing a structural gene including DNA sequences encoding the $V_H$ and $V_L$ domains connected by an oligonucleotide. In some embodiments, the scFv includes the amino acid sequence set forth as one of SEQ ID NOs: 10-12. The structural gene can be inserted into an expression vector, which is subsequently introduced into a host cell such as *E. coli*. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; Ahmad et al., *Clin. Dev. Immunol.*, 2012, doi:10.1155/2012/980250; Marbry, *IDrugs*, 13:543-549, 2010). Dimers of a single chain antibody (scFV$_2$), are also contemplated.

Antigen binding fragments can be prepared by proteolytic hydrolysis of the antibody or by expression in a host cell (such as an *E. coli* cell) of DNA encoding the fragment. Antigen binding fragments can also be obtained by pepsin or papain digestion of whole antibodies by conventional methods. For example, antigen binding fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. Nos. 4,036,945 and 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, *Academic Press*, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antigen binding fragments, such as dsFv fragments or in scFv fragments, will retain critical amino acid residues necessary for correct folding and stabilizing between the $V_H$ and the $V_L$ regions, and will retain the charge characteristics of the residues in order to preserve the low pI and low toxicity of the molecules. Amino acid substitutions (such as at most one, at most two, at most three, at most four, or at most five amino acid substitutions) can be made in the $V_H$ or the $V_L$ regions to increase yield. In particular examples, the $V_H$ sequence is one of SEQ ID NO: 1, 3, or 5. In other examples, the $V_L$ sequence is one of SEQ ID NO: 2, 4, or 6. Conservative amino acid substitution tables providing functionally similar amino acids are well known to one of ordinary skill in the art.

Also included are antibodies that bind to the same epitope on matrilin-3 to which the matrilin-3 specific antibodies provided herein (e.g., clone 13, 22, or 26) bind. Antibodies that bind to such an epitope can be identified based on their ability to cross-compete (for example, to competitively inhibit the binding of, in a statistically significant manner) with the matrilin-3 specific antibodies provided herein in matrilin-3 binding assays (such as those described in the Examples). An antibody "competes" for binding when the competing antibody inhibits matrilin-3 binding of an antibody of the invention by more than 50%, in the presence of competing antibody concentrations higher than $10^6 \times K_D$ of the competing antibody. In a certain embodiment, the antibody that binds to the same epitope on matrilin-3 as the antibodies of the present invention is a human monoclonal antibody. Such human monoclonal antibodies can be prepared and isolated as described herein.

Additionally, to increase binding affinity of the antibody, the $V_L$ and $V_H$ segments can be randomly mutated, such as within H-CDR3 region or the L-CDR3 region, in a process analogous to the in vivo somatic mutation process responsible for affinity maturation of antibodies during a natural immune response. Thus in vitro affinity maturation can be accomplished by amplifying $V_H$ and $V_L$ regions using PCR primers complementary to the H-CDR3 or L-CDR3, respectively. In this process, the primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be tested to determine the binding affinity for matrilin-3. In particular examples, the $V_H$ amino acid sequence is one of SEQ ID NOs: 1, 3, or 5. In other examples, the $V_L$ amino acid sequence is SEQ ID NOs: 2, 4, or 6.

B. Conjugates

Monoclonal antibodies specific for matrilin-3, or antigen binding fragments thereof, can be conjugated to an agent, such as an effector molecule or detectable marker, using any number of means known to those of skill in the art. The effector molecule may be heterologous and/or non-naturally occurring. Both covalent and noncovalent attachment means may be used. One of skill in the art will appreciate that various effector molecules and detectable markers can be used, including (but not limited to) chondrogenic agents, anti-arthritis agents, and radioactive agents such as $^{125}$I $^{32}$P, $^{14}$C, $^{3}$H and $^{35}$S and other labels, target moieties and ligands, etc. In several embodiments, the effector molecule is a polypeptide and is linked (for example by a heterologous peptide linker) to the N-terminus of an scFv including the heavy and light chain CDRs of a matrilin-3 specific antibody, such as the clone 13, clone 22, or clone 26 antibody.

The choice of a particular effector molecule or detectable marker depends on the particular target molecule or cell, and the desired biological effect. Thus, for example, the effector molecule can be a chondrogenic agent that is used to promote or stimulate chondrogenesis in cartilage tissue.

The procedure for attaching an effector molecule or detectable marker to an antibody or antigen binding fragment varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an a polypeptide to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, Ill. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. No. 7,964,566 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference in its entirety.

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In several embodiments, the linker is resistant to cleavage in an extracellular environment. For example, no more than about 20%, no more than about 15%, no more than about 10%, no more than about 5%, no more than about 3%, or no more than about 1% of the linkers, in a sample of conjugate, are cleaved when the conjugate is present in an extracellular environment (for example, in plasma). Whether or not a linker is resistant to cleavage in an extracellular environment can be determined, for example, by incubating the conjugate containing the linker of interest with plasma for a predetermined time period (for example, 2, 4, 8, 16, or 24 hours) and then quantitating the amount of free effector molecule or detectable marker present in the plasma. A variety of exemplary linkers that can be used in conjugates are described in WO 2004010957, U.S. Publication No. 2006/0074008, U.S. Publication No. 20050238649, and U.S. Publication No. 2006/0024317, each of which is incorporated by reference herein in its entirety.

In several embodiments, conjugates of an antibody or antigen binding fragment and one or more chondrogenic agents, are provided. Non-limiting examples of such chondrogenic agents include growth-regulating endocrine signaling molecules (e.g., growth hormone, IGF-1, steroids (e.g., an estrogen, an androgen, estradiol)), growth-regulating paracrine signaling molecules (e.g., Indian Hedgehog (IHH), bone morphogenetic proteins (BMPs), C-type natriuretic peptide (CNP), WNTs, and FGFs). In several embodiments, a chondrogenic agent is conjugated to a matrilin-3 specific antibody or antigen binding fragment (such as an antibody or antigen binding fragment including the CDRs of the clone 13, clone 22, or clone 26 antibodies disclosed herein).

In some embodiments the antibody or antigen binding fragment (such as an antibody or antigen binding fragment including the CDRs of one of the clone 13, clone 22, or clone 26 matrilin-3 specific antibodies) is conjugated to a growth hormone or fragment thereof that induces chondrogenesis. Human growth hormone is used for both growth hormone-deficiency and certain non-growth hormone-deficient causes of short stature (Richmond, *Current Indications for Growth Hormone Therapy* Vol. 18, Karger, 2010). Exemplary human growth hormone polypeptide and nucleic acid sequences are known to the person of ordinary skill in the art. For example, the polypeptide sequence of a human growth hormone precursor is provided in NCBI Ref. NP_000506.2 (incorporated by reference herein as present in the database on Dec. 1, 2103)

(SEQ ID NO: 18)
MATGSRTSLLLAFGLLCLPWLQEGSAFPTIPLSRLFDNAMLRAHRLHQLA

FDTYQEFEEAYIPKEQKYSFLQNPQTSLCFSESIPTPSNREETQQKSNLE

LLRISLLLIQSWLEPVQFLRSVFANSLVYGASDSNVYDLLKDLEEGIQTL

MGRLEDGSPRTGQIFKQTYSKFDTNSHNDDALLKNYGLLYCFRKDMDKVE

TFLRIVQCRSVEGSCGF

Further, the person of ordinary skill in the art can readily determine the polypeptide sequence of a mature growth hormone; for example mature human growth hormone can include a polypeptide sequence set forth as follows:

(SEQ ID NO: 19)
FPTIPLSRLFDNAMLRAHRLHQLAFDTYQEFEEAYIPKEQKYSFLQNPQT

SLCFSESIPTPSNREETQQKSNLELLRISLLLIQSWLEPVQFLRSVFANS

LVYGASDSNVYDLLKDLEEGIQTLMGRLEDGSPRTGQIFKQTYSKFDTNS

HNDDALLKNYGLLYCFRKDMDKVETFLRIVQCRSVEGSCGF

An exemplary nucleic acid sequence encoding a human growth hormone is set forth as NCBI Ref. NM_000515.3 (incorporated by reference herein as present in the database on Dec. 1, 2103)

(SEQ ID NO: 20)
Aggatcccaaggcccaactccccgaaccactcagggtcctgtggacagct cacctagctgcaatggctacaggctcccggacgtccctgctcctggcttt tggcctgctctgcctgccctggcttcaagagggcagtgccttcccaacca ttcccttatccaggcttttgacaacgctatgctccgcgcccatcgtctg caccagctggcctttgacacctaccaggagtttgaagaagcctatatccc aaaggaacagaagtattcattcctgcagaaccccagacctccctctgtt tctcagagtctattccgacaccctccaacagggaggaaacacaacagaaa tccaacctagagctgctccgcatctccctgctgctcatccagtcgtggct ggagcccgtgcagttcctcaggagtgtcttcgccaacagcctggtgtacg gcgcctctgacagcaacgtctatgacctcctaaaggacctagaggaaggc atccaaacgctgatggggaggctggaagatggcagcccccggactgggca gatcttcaagcagacctacagcaagttcgacacaaactcacacaacgatg acgcactactcaagaactacgggctgctctactgcttcaggaaggacatg gacaaggtcgagacattcctgcgcatcgtgcagtgccgctctgtggaggg cagctgtggcttctagctgcccgggtggcatccctgtgacccctcccag tgcctctcctggccctggaagttgccactccagtgcccaccagccttgtc ctaataaaattaagttgcatca In some embodiments the antibody or binding fragment (such as an antibody or antigen binding fragment including the CDRs of one of the clone 13, clone 22, or clone 26 matrilin-3 specific antibodies) is conjugated to an IGF-1 or fragment thereof that induces chondrogenesis. Exemplary IGF-1 polypeptide and nucleic acid sequences are known to the person of ordinary skill in the art. For example, the polypeptide sequence of IGF-1 precursor is set forth as UniProt Ref. No. P05019.1, incorporated by reference herein as present in the database on Dec. 1, 2103):

(SEQ ID NO: 21)
MGKISSLPTQLFKCCFCDFLKVKMHTMSSSHLFYLALCLLTFTSSATAGP

ETLCGAELVDALQFVCGDRGFYFNKPTGYGSSSRRAPQTGIVDECCFRSC

DLRRLEMYCAPLKPAKSARSVRAQRHTDMPKTQKYQPPSTNKNTKSQRRK

GWPKTHPGGEQKEGTEASLQIRGKKKEQRREIGSRNAECRGKKGK

Further, the person of ordinary skill in the art can readily determine the polypeptide sequence of a mature IGF-1; for example mature IGF-1 can include a polypeptide sequence set forth as follows:

(SEQ ID NO: 22)
GPETLCGAELVDALQFVCGDRGFYFNKPTGYGSSSRRAPQTGIVDECCFR

SCDLRRLEMYCAPLKPAKSA

In another example, the mature IGF-1 can include a polypeptide sequence set forth as (SEQ ID NO: 49)
GPETLCGAELVDALQFVCGDRGFYFNKPTGYGSSSRRAPQTGIVDECCFR

SCDLRRLEMYCAPL

An exemplary nucleic acid sequence encoding a human IGF-1 is set forth as GENBANK™ Ref. No. X00173.1, incorporated by reference herein as present in the database on Dec. 1, 2103)

(SEQ ID NO: 23)
Cttcagaagcaatgggaaaaatcagcagtcttccaacccaattatttaag tgctgcttttgtgatttcttgaaggtgaagatgcacaccatgtcctcctc gcatctcttctacctggcgctgtgcctgctcaccttcaccagctctgcca cggctggaccggagacgctctgcggggctgagctggtggatgctcttcag ttcgtgtgtggagacaggggcttttatttcaacaagcccacagggtatgg ctccagcagtcggagggcgcctcagacaggtatcgtggatgagtgctgct tccggagctgtgatctaaggaggctggagatgtattgcgcaccctcaag cctgccaagtcagctcgctctgtccgtgcccagcgccacaccgacatgcc caagacccagaaggaagtacatttgaagaacgcaagtagagggagtgcag gaaacaagaactacaggatgtaggaagaccctcctgaggagtgaagagtg acatgccaccgcaggatcctttgctctgcacgagttacctgttaaacttt ggaacacctaccaaaaaataagtttgataacatttaaaagatgggcgttt cccccaatgaaatacacaagtaaacattccaacattgtctttaggagtga tttgcaccttgcaaaaatggtcctggagttggtagattgctgttgatctt ttatcaataatgttctatagaaaag In some embodiments the antibody or antigen binding fragment (such as an antibody or antigen binding fragment including the CDRs of one of the clone 13, clone 22, or clone 26 matrilin-3 specific antibodies as disclosed herein) is conjugated to an Indian Hedgehog (IHH) protein or fragment thereof that induces chondrogenesis. IHH is known to stimulate growth plate chondrogenesis (Chau, et al. *J Mol Endocrinol* 47, 99-107, 2011; Kobayashi, et al. *J Clin Invest* 115, 1734-1742, 2005; Kronenberg. *Ann N Y Acad Sci* 1068, 1-13, 2006; Maeda, et al. *Proc Natl Acad Sci USA* 104, 6382-6387, 2007; Long, et al. *Dev Biol* 298, 327-333, 2006; Amizuka, et al. *J Cell Biol* 126, 1611-1623, 1994; Long, et al. *Development* 128, 5099-5108, 2001; Mak, et al. *Development* 135, 1947-1956, 2008). Exemplary IHH polypeptide and nucleic acid sequences are known to the person of ordinary skill in the art. For example, the polypeptide sequence of an IHH precursor is set forth as NCBI Ref. No. NP_002172.2, incorporated by reference herein as present in the database on Dec. 1, 2103):

(SEQ ID NO: 24)
MSPARLRPRLHFCLVLLLLLVVPAAWGCGPGRVVGSRRRPPRKLVPLAYK

QFSPNVPEKTLGASGRYEGKIARSSERFKELTPNYNPDIIFKDEENTGAD

RLMTQRCKDRLNSLAISVMNQWPGVKLRVTEGWDEDGHHSEESLHYEGRA

VDITTSDRDRNKYGLLARLAVEAGFDWVYYESKAHVHCSVKSEHSAAAKT

GGCFPAGAQVRLESGARVALSAVRPGDRVLAMGEDGSPTFSDVLIFLDRE

PHRLRAFQVIETQDPPRRLALTPAHLLFTADNHTEPAARFRATFASHVQP

GQYVLVAGVPGLQPARVAAVSTHVALGAYAPLTKHGTLVVEDVVASCFAA

VADHHLAQLAFWPLRLFHSLAWGSWTPGEGVHWYPQLLYRLGRLLLEEGS

FHPLGMSGAGS

Further, the person of ordinary skill in the art can readily determine the polypeptide sequence of a mature IHH; for example mature IHH can include a polypeptide sequence set forth as follows:

(SEQ ID NO: 25)
GPGRVVGSRRRPPRKLVPLAYKQFSPNVPEKTLGASGRYEGKIARSSERF

KELTPNYNPDIIFKDEENTGADRLMTQRCKDRLNSLAISVMNQWPGVKLR

VTEGWDEDGHHSEESLHYEGRAVDITTSDRDRNKYGLLARLAVEAGFDWV

YYESKAHVHCSVKSEHSAAAKTGGCFPAGAQVRLESGARVALSAVRPGDR

VLAMGEDGSPTFSDVLIFLDREPHRLRAFQVIETQDPPRRLALTPAHLLF

TADNHTEPAARFRATFASHVQPGQYVLVAGVPGLQPARVAAVSTHVALGA

YAPLTKHGTLVVEDVVASCFAAVADHHLAQLAFWPLRLFHSLAWGSWTPG

EGVHWYPQLLYRLGRLLLEEGSFHPLGMSGAGS

An exemplary nucleic acid sequence encoding IHH is set forth as NCBI Ref. No. NM_002181.3, incorporated by reference herein as present in the database on Dec. 1, 2103)

(SEQ ID NO: 26)
atcagcccaccaggagacctcgcccgccgctccccgggctccccggcca tgtctcccgccggctccggcccgactgcacttctgcctggtcctgttg ctgctgctggtggtgccggcggcatggggctgcgggccgggtcgggtggt gggcagccgccggcgaccgccacgcaaactcgtgccgctcgcctacaagc agttcagccccaatgtgcccgagaagaccctgggcgccagcggacgctat gaaggcaagatcgctcgcagctccgagcgcttcaaggagctcaccccaa ttacaatccagacatcatcttcaaggacgaggagaacacaggcgccgacc gcctcatgacccagcgctgcaaggaccgcctgaactcgctggctatctcg gtgatgaaccagtggccggtgtgaagctgcgggtgaccgagggctggga cgaggacggccaccactcagaggagtccctgcattatgagggccgcgcgg tggacatcaccacatcagaccgcgaccgcaataagtatggactgctggcg cgcttggcagtggaggccggctttgactgggtgtattacgagtcaaaggc ccacgtgcattgctccgtcaagtccgagcactcggccgcagccaagacgg gcggctgcttccctgccggagcccaggtacgcctggagagtggggcgcgt gtggccttgtcagccgtgaggccgggagaccgtgtgctggccatggggga ggatgggagccccaccttcagcgatgtgctcattttcctggaccgcgagc ctcacaggctgagagccttccaggtcatcgagactcaggaccccccacgc cgcctggcactcacacccgctcacctgctctttacggctgacaatcacac ggagccggcagcccgcttccgggccacatttgccagccacgtgcagcctg gccagtacgtgctggtggctggggtgccaggcctgcagcctgcccgcgtg gcagctgtctctacacacgtggccctcggggcctacgcccgctcacaaa gcatgggacactggtggtggaggatgtggtggcatcctgcttcgcggccg tggctgaccaccacctggctcagttggccttctggcccctgagactcttt cacagcttggcatggggcagctggaccccggggagggtgtgcattggta ccccagctgctctaccgcctgggcgtctcctgctagaagagggcagct tccaccactgggcatgtccggggcagggagctgaaaggactccaccgct gccctcctggaactgctgtactgggtccagaagcctctcagccaggaggg agctggccctggaagggacctgagctgggggacactggctcctgccatct cctctgccatgaagatacaccattgagacttgactgggcaacaccagcgt ccccaccccgtcgtggtgtagtcatagagctgcaagctgagctggcga ggggatggttgttgaccctctctcctagagaccttgaggctggcacggc gactcccaactcagcctgctctcactacgagttttcatactctgcctccc ccattgggagggcccattccatccatcttaggccccttgggtgggctt gcgcctcagttgatgctgctaaattccctgggagccagcatggatctggc tggacccgatgctgtccagaactgggaaggccacaggggtggggcagcca tcccggccattctgaggtatgacattcctccccggccacactcctcaaga cacatccagagactgttgctgtctgtgggcagagttctgtgttctggca atgtgaccgtagtgccggggactggggaggtgggttggatgtgcttgcc acccccccggctaagctccccccttctgctgaaccatgatccccacccct ccgccggtcagtctcccataccttatttattggagtggaggggaagccc atgggagaattttggggatgttttggtcttttcttcctttgtaataaaa attatttaagttgttagagccaaa In some embodiments the antibody or antigen binding fragment (such as an antibody or antigen binding fragment including the CDRs of one of the clone 13, clone 22, or clone 26 matrilin-3 specific antibodies) is conjugated to a bone morphogenic protein (BMP) or fragment thereof that induces chondrogenesis. BMPs are known to stimulate growth plate chondrogenesis (De Luca, et al. *Endocrinology* 142, 430-436, 2001; Nilsson, et al. *J Endocrinol* 193, 75-84, 2007; Kobayashi, et al. *Proc Natl Acad Sci USA* 102, 18023-18027, 2005; Yoon, et al. *Development* 133, 4667-4678, 2006; Wu, et al. *J Biol Chem* 286, 24726-24734, 2011; Yoon, et al. *Proc Natl Acad Sci USA* 102, 5062-5067, 2005). Exemplary BMP polypeptide and nucleic acid sequences are known to the person of ordinary skill in the art. For example, polypeptide and encoding nucleic acid sequences of BMP1 (NM_001199.3; NP_001190.1), BMP2 (NM_001200.2; NP_001191.1), BMP3 (NM_001201.2; NP_001192.2), BMP4 (NM_001202.3; NP_001193.2), BMP6 (NM_021073.2; NP_066551.1), BMP7 (NM_001719.2; NP_001710.1), BMP8A (NM_181809.3; NP_861525.2) are known, and the indicated NCBI Ref. Nos. are each incorporated by reference herein as present in the database on Dec. 1, 2013. In one non-limiting example, the polypeptide sequence of a BMP1 precursor is set forth as NCBI Ref. No. NP_001190.1, incorporated by reference herein as present in the database on Dec. 1, 2103):

(SEQ ID NO: 27)
MPGVARLPLLLGLLLLPRPGRPLDLADYTYDLAEEDDSEPLNYKDPCKAA

AFLGDIALDEEDLRAFQVQQAVDLRRHTARKSSIKAAVPGNTSTPSCQST

NGQPQRGACGRWRGRSRSRRAATSRPERVWPDGVIPFVIGGNFTGSQRAV

FRQAMRHWEKHTCVTFLERTDEDSYIVFTYRPCGCCSYVGRRGGGPQAIS

IGKNCDKFGIVVHELGHVVGFWHEHTRPDRDRHVSIVRENIQPGQEYNFL

KMEPQEVESLGETYDFDSIMHYARNTFSRGIFLDTIVPKYEVNGVKPPIG

QRTRLSKGDIAQARKLYKCPACGETLQDSTGNFSSPEYPNGYSAHMHCVW

RISVTPGEKIILNFTSLDLYRSRLCWYDYVEVRDGFWRKAPLRGRFCGSK

LPEPIVSTDSRLWVEFRSSSNWVGKGFFAVYEAICGGDVKKDYGHIQSPN

YPDDYRPSKVCIWRIQVSEGFHVGLTFQSFEIERHDSCAYDYLEVRDGHS

ESSTLIGRYCGYEKPDDIKSTSSRLWLKFVSDGSINKAGFAVNFFKEVDE

CSRPNRGGCEQRCLNTLGSYKCSCDPGYELAPDKRRCEAACGGFLTKLNG

SITSPGWPKEYPPNKNCIWQLVAPTQYRISLQFDFFETEGNDVCKYDFVE

VRSGLTADSKLHGKFCGSEKPEVITSQYNNMRVEFKSDNTVSKKGFKAHF

FSEKRPALQPPRGRPHQLKFRVQKRNRTPQ

Further, the person of ordinary skill in the art can readily determine the polypeptide sequence of a mature BMP; for example the polypeptide sequence of mature BMP1 is set forth as follows:

(SEQ ID NO: 28)
LDLADYTYDLAEEDDSEPLNYKDPCKAAAFLGDIALDEEDLRAFQVQQAV

DLRRHTARKSSIKAAVPGNTSTPSCQSTNGQPQRGACGRWRGRSRSRRAA

TSRPERVWPDGVIPFVIGGNFTGSQRAVFRQAMRHWEKHTCVTFLERTDE

DSYIVFTYRPCGCCSYVGRRGGGPQAISIGKNCDKFGIVVHELGHVVGFW

HEHTRPDRDRHVSIVRENIQPGQEYNFLKMEPQEVESLGETYDFDSIMHY

ARNTFSRGIFLDTIVPKYEVNGVKPPIGQRTRLSKGDIAQARKLYKCPAC

GETLQDSTGNFSSPEYPNGYSAHMHCVWRISVTPGEKIILNFTSLDLYRS

RLCWYDYVEVRDGFWRKAPLRGRFCGSKLPEPIVSTDSRLWVEFRSSSNW

VGKGFFAVYEAICGGDVKKDYGHIQSPNYPDDYRPSKVCIWRIQVSEGFH

VGLTFQSFEIERHDSCAYDYLEVRDGHSESSTLIGRYCGYEKPDDIKSTS

SRLWLKFVSDGSINKAGFAVNFFKEVDECSRPNRGGCEQRCLNTLGSYKC

SCDPGYELAPDKRRCEAACGGFLTKLNGSITSPGWPKEYPPNKNCIWQLV

APTQYRISLQFDFFETEGNDVCKYDFVEVRSGLTADSKLHGKFCGSEKPE

VITSQYNNMRVEFKSDNTVSKKGFKAHFFSEKRPALQPPRGRPHQLKFRV

QKRNRTPQ

An exemplary nucleic acid sequence encoding BMP1 is set forth as NCBI Ref. No. NM_001199.3, incorporated by reference herein as present in the database on Dec. 1, 2103)

(SEQ ID NO: 29)
gtcggagggagggagggagggagagaaagaaagagagaaaaagaaggaaa gggagagggagacggctggagcccgaggacgagcgcggagccgcggaccg agcgggggcgggagacaggaaggagggaggcgagcagagggaaggggaa gaggtcggggagcgagggcgggagcggtcgcggtcgcgatcgagcaagca agcgggcgagaggacgccctcccctggcctccagtgcgccgcttccctcg ccgccgccccgccagcatgcccggcgtggcccgcctgccgctgctgctcg ggctgctgctgctcccgcgtcccggccggccgctggacttggccgactac acctatgacctggcggaggaggacgactcggagcccctcaactacaaaga cccctgcaaggcggctgcctttcttggggacattgccctggacgaagagg acctgagggccttccaggtacagcaggctgtggatctcagacggcacaca gctcgtaagtcctccatcaaagctgcagttccaggaaacacttctacccc cagctgccagagcaccaacgggcagcctcagaggggagcctgtgggagat ggagaggtagatcccgtagccggcgggcggcgacgtcccgaccagagcgt gtgtggcccgatgggctcatcccctttgtcattgggggaaacttcactgg tagccagagggcagtcttccggcaggccatgaggcactgggagaagcaca cctgtgtcaccttcctggagcgcactgacgaggacagctatattgtgttc acctatcgaccttgcgggtgctgctcctacgtgggtcgccgcggcggggg ccccaggccatctccatcggcaagaactgtgacaagttcggcattgtgg tccacgagctgggccacgtcgtcggcttctggcacgaacacactcggcca gaccgggaccgccacgtttccatcgttcgtgagaacatccagccagggca ggagtataacttcctgaagatggagcctcaggaggtggagtccctggggg agacctatgacttcgacagcatcatgcattacgctcggaacacattctcc aggggcatcttcctggataccattgtccccaagtatgaggtgaacgggt gaaacctcccattggccaaaggacacggctcagcaaggggacattgccc aagcccgcaagctttacaagtgcccagcctgtggagagaccctgcaagac agcacaggcaacttctcctcccctgaataccccaatggctactctgctca catgcactgcgtgtggcgcatctctgtcacaccggggagaagatcatcc tgaacttcacgtccctggacctgtaccgcagccgcctgtgctggtacgac tatgtggaggtccgagatggcttctggaggaaggcgcccctccgaggccg cttctgcgggtccaaactccctgagcctatcgtctccactgacagccgcc tctgggttgaattccgcagcagcagcaattgggttggaaagggcttcttt gcagtctacgaagccatctgcggggtgatgtgaaaaaggactatggcca cattcaatcgcccaactacccagacgattaccggcccagcaaagtctgca tctggcggatccaggtgtctgagggcttccacgtgggcctcacattccag tcctttgagattgagcgccacgacagctgtgcctacgactatctggaggt gcgcgacgggcacagtgagagcagcaccctcatcgggcgctactgtggct atgagaagcctgatgacatcaagagcacgtccagccgcctctggctcaag ttcgtctctgacgggtccattaacaaagcgggctttgccgtcaacttttt caaagaggtggacgagtgctctcggcccaaccgcggggggctgtgagcagc ggtgcctcaacaccctgggcagctacaagtgcagctgtgaccccgggtac

```
-continued
gagctggccccagacaagcgccgctgtgaggctgcttgtggcggattcct caccaagctcaacggctccatcaccagcccgggctggcccaaggagtacc cccccaacaagaactgcatctggcagctggtggccccacccagtaccgc atctccctgcagtttgacttctttgagacagagggcaatgatgtgtgcaa gtacgacttcgtggaggtgcgcagtggactcacagctgactccaagctgc atggcaagttctgtggttctgagaagcccgaggtcatcacctcccagtac aacaacatgcgcgtggagttcaagtccgacaacaccgtgtccaaaaaggg cttcaaggcccacttcttctcagaaaagaggccagctctgcagcccctc ggggacgccccaccagctcaaattccgagtgcagaaaagaaaccggacc ccccagtgaggcctgccaggcctcccggaccccttgttactcaggaacct caccttggacggaatgggatgggggcttcggtgcccaccaacccccacc tccactctgccattccggcccacctccctctggccggacagaactggtgc tctcttctcccactgtgcccgtccgcggaccggggacccttccccgtgc cctaccccctcccatttgatggtgtctgtgacatttcctgttgtgaagt aaaagagggaccccctgcgtcctgctcctttctcttgcagaaaaaaaa
```

In some embodiments the antibody or antigen binding fragment (such as an antibody or antigen binding fragment including the CDRs of one of the clone 13, clone 22, or clone 26 matrilin-3 specific antibodies) is conjugated to a CNP or fragment thereof that induces chondrogenesis. CNP variants can also be including in the disclosed conjugates; several CNP variants are known, including those described in U.S. Pat. App. Pub. No. 20130096061, 20120316114, and 2004/0138134, each of which is incorporated by reference herein in its entirety. CNPs are known to promote growth plate chondrogenesis (Mericq, et al. *Pediatr Res* 47, 189-193, 2000; Agoston, et al. *BMC Dev Biol* 7, 18, 2007; Olney, et al. *J Clin Endocrinol Metab* 92, 4294-4298, 2007; Olney, et al. *J Clin Endocrinol Metab* 91, 1229-1232, 2006; Teixeira, et al. *Dev Biol* 319, 171-178, (2008); Woods, et al. *Endocrinology* 148, 5030-5041, 2007). Exemplary CNP polypeptide and nucleic acid sequences are known to the person of ordinary skill in the art. In one non-limiting example, a polypeptide sequence of a CNP precursor is set forth as NCBI Ref. No. NP_077720.1, incorporated by reference herein as present in the database on Dec. 1, 2103):

(SEQ ID NO: 30)
MHLSQLLACALLLTLLSLRPSEAKPGAPPKVPRTPPAEELAEPQAAGGGQ

KKGDKAPGGGGANLKGDRSRLLRDLRVDTKSRAAWARLLQEHPNARKYKG

ANKKGLSKGCFGLKLDRIGSMSGLGC

Several active fragments of CNP are known to the person of ordinary skill in the art, including CNP-53 (DLRVDTKSRAAWARLLQEHPNARKYKGANKKGLSKGCFGLKLDRIGSMSGLGC; SEQ ID NO: 31), CNP-29 (YKGANKKGLSKGCFGLKLDRIGSMSGLGC; SEQ ID NO: 32), and CNP-22 (GLSKGCFGLKLDRIGSMSGLGC; SEQ ID NO: 33). These active fragments of CNP can be linked to the antibody or antigen binding fragment.

An exemplary nucleic acid sequence encoding BMP1 is set forth as NCBI Ref. No. NM_024409.2, incorporated by reference herein as present in the database on Dec. 1, 2103)

```
(SEQ ID NO: 34)
Cgcatcccctgctggtctgcccgccgacctgcgcgccctcgctgccgcc cgtgtgcgccctcgacccagcggcaccatgcatctctcccagctgctg gcctgcgccctgctgctcacgctgctctccctccggccctccgaagccaa gcccggggcgccgccgaaggtcccgcgaaccccgccggcagaggagctgg ccgagccgcaggctgcgggcggcggtcagaagaagggcgacaaggctccc gggggcgggggcgccaatctcaagggcgaccggtcgcgactgctccggga cctgcgcgtggacaccaagtcgcgggcagcgtgggctcgccttctgcaag agcaccccaacgcgcgcaaatacaaaggagccaacaagaagggcttgtcc aagggctgcttcggcctcaagctggaccgaatcggctccatgagcggcct gggatgttagtgcggcgcccctggcggcggatcgggaactggctccgtt gtgctgaggtcatctttggtcatcagcctccagcatctggaaacacctcc aacgcaatgtggcttttacatttctttctttctttcttttttttcctgg tactgggaatacacaacaccagctgttttattatttggggagggggt tgtgattttattatttgttttttaaaatgaaaaataaaaagttatatat
t
```

In some embodiments the antibody or antigen binding fragment (such as an antibody or antigen binding fragment including the CDRs of one of the clone 13, clone 22, or clone 26 matrilin-3 specific antibodies) is conjugated to a Wnt protein or fragment thereof that induces chondrogenesis. WNT proteins are known to promote chondrogenesis (see, e.g., Andrade, et al. *Bone* 40, 1361-1369, 2007; Hartmann, et al. *Development* 127, 3141-3159, 2000; Yates, et al. *DNA Cell Biol* 24, 446-457, 2005; Yang, et al. *Development* 130, 1003-1015, 2003; Akiyama, et al. *Genes Dev* 18, 1072-1087, 2004). Exemplary Wnt polypeptide and nucleic acid sequences are known to the person of ordinary skill in the art. For example, polypeptide and encoding nucleic acid sequences of Wnt1 (NP_005421.1; NM_005430.3), Wnt2 (NM_003391.2; NP_003382.1), Wnt3 (NM_030753.4; NP_110380.1), Wnt4 (NM_030761.4; NP_110388.2), Wnt5 (NM_001256105.1; NP_001243034.1), are known, each of which is incorporated by reference herein as present in the database on Dec. 1, 2013. In one non-limiting example, the polypeptide sequence of Wnt1 precursor is set forth as NCBI Ref. No. NP_005421.1, incorporated by reference herein as present in the database on Dec. 1, 2103)

(SEQ ID NO: 35)
MGLWALLPGWVSATLLLALAALPAALAANSSGRWWGIVNVASSTNLLTDS

KSLQLVLEPSLQLLSRKQRRLIRQNPGILHSVSGGLQSAVRECKWQFRNR

RWNCPTAPGPHLFGKIVNRGCRETAFIFAITSAGVTHSVARSCSEGSIES

CTCDYRRRGPGGPDWHWGGCSDNIDFGRLFGREFVDSGEKGRDLRFLMNL

HNNEAGRTTVFSEMRQECKCHGMSGSCTVRTCWMRLPTLRAVGDVLRDRF

DGASRVLYGNRGSNRASRAELLRLEPEDPAHKPPSPHDLVYFEKSPNFCT

YSGRLGTAGTAGRACNSSSPALDGCELLCCGRGHRTRTQRVTERCNCTFH

WCCHVSCRNCTHTRVLHECL

Further, the person of ordinary skill in the art can readily determine the polypeptide sequence of mature Wnts; for example the polypeptide sequence of mature Wnt1 is set forth as follows:

(SEQ ID NO: 36)
ANSSGRWWGIVNVASSTNLLTDSKSLQLVLEPSLQLLSRKQRRLIRQNPG

ILHSVSGGLQSAVRECKWQFRNRRWNCPTAPGPHLFGKIVNRGCRETAFI

FAITSAGVTHSVARSCSEGSIESCTCDYRRRGPGGPDWHWGGCSDNIDFG

RLFGREFVDSGEKGRDLRFLMNLHNNEAGRTTVFSEMRQECKCHGMSGSC

TVRTCWMRLPTLRAVGDVLRDRFDGASRVLYGNRGSNRASRAELLRLEPE

DPAHKPPSPHDLVYFEKSPNFCTYSGRLGTAGTAGRACNSSSPALDGCEL

LCCGRGHRTRTQRVTERCNCTFHWCCHVSCRNCTHTRVLHECL

An exemplary nucleic acid sequence encoding Wnt1 is set forth as NCBI Ref. No. NM_005430.3, incorporated by reference herein as present in the database on Dec. 1, 2103)

(SEQ ID NO: 37)
gcggtgccgcccgccgtggccgcctcagcccaccagccgggaccgcgagc catgctgtccgccgcccgccccagggttgttaaagccagactgcgaact ctcgccactgccgccaccgccgcgtcccgtcccaccgtcgcgggcaacaa ccaaagtcgccgcaactgcagcacagagcgggcaaagccaggcaggccat ggggctctgggcgctgttgcctggctgggtttctgctacgctgctgctgg cgctggccgctctgcccgcagccctggctgccaacagcagtggccgatgg tggggtattgtgaacgtagcctcctccacgaacctgcttacagactccaa gagtctgcaactggtactcgagcccagtctgcagctgttgagccgcaaac agcggcgtctgatacgccaaaatccggggatcctgcacagcgtgagtggg gggctgcagagtgccgtgcgcgagtgcaagtggcagttccggaatcgccg ctggaactgtcccactgctccagggcccacctcttcggcaagatcgtca accgaggctgtcgagaaacggcgtttatcttcgctatcacctccgccggg gtcacccattcggtggcgcgctcctgctcagaaggttccatcgaatcctg cacgtgtgactaccggcggcgcggccccgggggcccgactggcactggg ggggctgcagcgacaacattgacttcggccgcctcttcggcgggagttc gtggactccggggagaagggcgggacctgcgcttcctcatgaaccttca caacaacgaggcaggccgtacgaccgtattctccgagatgcgccaggagt gcaagtgccacgggatgtccggctcatgcacggtgcgcacgtgctggatg cggctgcccacgctgcgcgccgtgggcgatgtgctgcgcgaccgcttcga cggcgcctcgcgcgtcctgtacggcaaccgcggcagcaaccgcgcttcgc gggcggagctgctgcgcctggagccggaagacccggcccacaaaccgccc tccccccacgacctcgtctacttcgagaaatcgcccaacttctgcacgta cagcggacgcctgggcacagcaggcacggcagggcgcgcctgtaacagct cgtcgcccgcgctggacggctgcgagctgctctgctgcggcaggggccac cgcacgcgcacgcagcgcgtcaccgagcgctgcaactgcaccttccactg gtgctgccacgtcagctgccgcaactgcacgcacacgcgcgtactgcacg agtgtctgtgaggcgctgcgcggactcgccccaggaacgctctcctcga gccctccccaaacagactcgctagcactcaagacccggttattcgccca cccgagtacctccagtcacactcccgcggttcatacgcatcccatctct cccacttcctcctacctggggactcctcaaaccacttgcctggcggca tgaaccctcttgccatcctgatggacctgccccggacctacctccctccc tctccgcgggagacccttgttgcactgccccctgcttggccaggaggtg agagaaggatgggtcccctccgccatggggtcggctcctgatggtgtcat tctgcctgctccatcgcgccagcgacctctctgcctctcttcttcccctt tgtcctgcgttttctccgggtcctcctaagtcccttcctattctcctgcc atgggtgcagaccctgaacccacacctgggcatcagggcctttctcctcc ccacctgtagctgaagcaggaggttacagggcaaaagggcagctgtgatg atgtggaaatgaggttgggggaaccagcagaaatgccccccattctcccag tctctgtcgtggagccattgaacagctgtgagccatgcctccctgggcca cctcctacccttcctgtcctgcctcctcatcagtgtgtaaataatttgc actgaaacgtggatacagagccacgagtttggatgttgtaaataaaacta tttattgtgctgggtcccagcctggtttgcaaagaccacctccaacccaa cccaatccctctccactcttctctccttcctcctgcagcctttctggt ccctcttctctcctcagtttctcaaagatgcgtttgcctcctggaatcag tatttccttccactgtagctattagcggctcctcgcccccaccagtgtag catcttcctctgcagaataaaatctctatttta In some embodiments the antibody or antigen binding fragment (such as an antibody or antigen binding fragment including the CDRs of one of the clone 13, clone 22, or clone 26 matrilin-3 specific antibodies) is conjugated to a parathyroid hormone (PTH) protein or fragment thereof that binds the type 1 PTH receptor. PTH binding to the type 1 PTH receptor is known to suppress chondrocyte maturation and reduce cartilage degradation in osteoporosis models (see, e.g., Sampson et al., Sci. Transl. Med., 3:101ra93, 2011). Exemplary PTH polypeptide and nucleic acid sequences are known to the person of ordinary skill in the art. An exemplary polypeptide sequence of a PTH protein is set forth as are available as NCBI Ref. No. NP_000306.1, which is incorporated by reference herein as present in the database on Jan. 3, 2015, and provides as:

(SEQ ID NO: 50)
KSVKKRSVSEIQLMHNLGKHLNSMERVEWLRKKLQDVHNFVALGAPLAPR

DAGSQRPRKKEDNVLVESHEKSLGEADKADVNVLTKAKSQ

Mature forms of PTH can also be used in a disclosed conjugate, such as (SEQ ID NO: 51)
KSVKKRSVSEIQLMHNLGKHLNSMERVEWLRKKLQDVHNFVALGAPLAPR

DAGSQRPRKKEDNVLVESHEKSLGEADKADVNVLTKAKSQ

In additional embodiments, the "teriparatide" sequence of PTH (residues 1-34) can be used in a disclosed conjugate, which is set forth as: SVSEIQLMHNLGKHLNS-MERVEWLRKKLQDVHNF (SEQ ID NO: 52).

An exemplary nucleic acid sequence encoding a PTH protein is set forth as NCBI Ref. No. NM_000315.2, incorporated by reference herein as present in the database on Jan. 3, 2015), and provided as (SEQ ID NO: 53)
```
Aaaagtcaccatttaagggtctgcagtccaattcatcagttgtctttag tttactcagcatcagctactaacatacctgaacgaagatcttgttctaag acattgtatgtgaagatgatacctgcaaaagacatggctaaagttatgat tgtcatgttggcaatttgttttcttacaaaatcggatgggaaatctgtta agaagagatctgtgagtgaaatacagcttatgcataacctgggaaaacat ctgaactcgatggagagtagaatggctgcgtaagaagctgcaggatgt gcacaatttgttgcccttggagctcctctagctcccagagatgctggtt cccagaggcccgaaaaaggaagacaatgtcttggttgagagccatgaa aaaagtcttggagaggcagacaaagctgatgtgaatgtattaactaaagc taaatcccagtgaaaatgaaaacagatattgtcagagttctgctctagac agtgtagggcaacaatacatgctgctaattcaaagctctattaagatttc caagtgccaatatttctgatataacaaactacatgtaatccatcactagc catgataactgcaattttaattgattattctgattccacttttattcatt tgagttattttaattatcttttctattgtttattcttttaaagtatgtt attgcataatttataaaagaataaaattgcacttttaaacctctcttcta ccttaaaatgtaaaacaaaaatgtaatgatcataagtctaaataaatgaa gtatttctcactcaaaaaaaaaaaaaa
```

In some embodiments, conjugates of an antibody or antigen binding fragment and one or more anti-inflammatory agents are provided. Non-limiting examples of such agents include dexamethasone, prednisone, and prednisolone. These conjugates inhibit chondrogenesis, and therefore are not useful as chondrogenic agents, but can be used, for example, for treatment of inflammation associated with arthritis. In additional embodiments, conjugates of an antibody or antigen binding fragment and one or more agents that inhibit inflammation and/or local immune response (such as an anti-arthritis agent), are provided. Non-limiting examples of such agents include dexamethasone, prednisone, prednisolone, etanercept, adalimumab, infliximab, rituximab, anakinra. These agents can be used, for example, for the treatment of auto-immune disorders affecting cartilage, such as rheumatoid arthritis.

Conjugates including the antibody or antigen binding fragment linked to one or more anti-arthritis agents or chondrogenic agents (such as a growth-regulating endocrine signaling molecule (e.g., a growth hormone or a IGF-1), a growth-regulating paracrine signaling molecule (such as an IHH, a BMP, a CNP, a Wnt, or a FGF), or a steroid (e.g., an estrogen, an androgen, estradiol), can be produced according to known methods. In one non-limiting example, a nucleic acid molecule encoding a chondrogenic agent (such as a growth-regulating endocrine signaling molecule (e.g., growth hormone or IGF-1), or a growth-regulating paracrine signaling molecules (such as an IHH, a BMP, a CNP, a Wnt, or a FGF) is operably linked to a nucleic acid molecule encoding the antibody or antigen binding fragment, for example and antibody or antigen binding fragment that specifically binds to matrilin-3, such as an antibody or antigen binding fragment including the CDRs of the clone 13, clone 22, or clone 26 antibodies. In the case of an scFv, the effector molecule can be linked to the N- and/or C-terminus of the scFv, for example. In the case of an IgG, the effector molecule can be linked to the N- and/or C-terminus of the heavy or light chain of the IgG. The nucleic acid molecule can encode one or more chondrogenic agents, which can be linked in series to the antibody or antigen binding fragment. Expression of the nucleic acid molecules under suitable conditions can be used to produce the conjugate.

In further embodiments an antibody or matrilin-3 binding fragment thereof (such as an antibody or antigen binding fragment that includes the CDRs of the clone 13, clone 22, or clone 26 matrilin-3 specific antibodies as disclosed herein) is conjugated to a steroid, such as dexamethasone or estradiol. Conjugating estradiol to peptides that bind to bone matrix has been shown to successfully deliver the steroid hormone to bone tissue in mice, with a marked increase in the retention time, producing biological effects on bone tissue while minimizing effects on non-skeletal tissues (Yokogawa, et al. *Endocrinology* 142, 1228-1233, 2001).

The antibody or antigen binding fragment can also be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-naphthalenesulfonyl chloride, phycoerythrin, lanthanide phosphors and the like. Bioluminescent markers are also of use, such as luciferase, Green fluorescent protein (GFP), Yellow fluorescent protein (YFP). An antibody or antigen binding fragment can also be conjugated with enzymes that are useful for detection, such as horseradish peroxidase, β-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody or antigen binding fragment may also be conjugated with biotin, and detected through indirect measurement of avidin or streptavidin binding. It should be noted that the avidin itself can be conjugated with an enzyme or a fluorescent label.

The antibody or antigen binding fragment can be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

The antibody or antigen binding fragment can also be conjugated with a radiolabeled amino acid. The radiolabel may be used for both diagnostic and therapeutic purposes. For instance, the radiolabel may be used to detect matrilin-3 and matrilin-3 expressing cells by x-ray, emission spectra, or other diagnostic techniques. Examples of labels for polypeptides include, but are not limited to, the following radioisotopes or radionucleotides: $^{3}$H, $^{14}$C, $^{15}$N, $^{35}$S, $^{90}$Y, $^{99}$Tc, $^{111}$In, $^{125}$I, $^{131}$I.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

The average number of effector molecule or detectable marker moieties per antibody or antigen binding fragment in a conjugate can range, for example, from 1 to 20 moieties per antibody or antigen binding fragment. In certain embodiments, the average number of effector molecule or detectable marker moieties per antibody or antigen binding fragment in a conjugate range from about 1 to about 2, from about 1 to about 3, about 1 to about 8; from about 2 to about 6; from about 3 to about 5; or from about 3 to about 4. The loading (for example, effector molecule/antibody ratio) of an conjugate may be controlled in different ways, for example, by: (i) limiting the molar excess of effector molecule-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number or position of linker-effector molecule attachments.

C. Polynucleotides and Expression

Nucleic acid molecules (also referred to as polynucleotides) encoding the polypeptides provided herein (including, but not limited to antibodies, antigen binding fragments and conjugates) can readily be produced by one of skill in the art. For example, these nucleic acids can be produced using the amino acid and nucleic acid sequences provided herein (such as the CDR sequences, heavy chain and light chain sequences and sequences of chondrogenic agents).

One of skill in the art can readily use the genetic code to construct a variety of functionally equivalent nucleic acids, such as nucleic acids which differ in sequence but which encode the same antibody sequence, or encode a conjugate or fusion protein including the $V_L$ and/or $V_H$ nucleic acid sequence.

The nucleic acid molecules can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template.

Exemplary nucleic acids can be prepared by cloning techniques. Examples of appropriate cloning and sequencing techniques, and instructions sufficient to direct persons of skill through many cloning exercises are known (see, e.g, Sambrook et al. (Molecular Cloning: A Laboratory Manual, 4$^{th}$ ed, Cold Spring Harbor, N.Y., 2012) and Ausubel et al. (In Current Protocols in Molecular Biology, John Wiley & Sons, New York, through supplement 104, 2013). Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

The nucleic acid molecules can be expressed in a recombinantly engineered cell such as bacteria, plant, yeast, insect and mammalian cells. The antibodies antigen binding fragments, and conjugates can be expressed as individual $V_H$ and/or $V_L$ chain (linked to an effector molecule or detectable marker as needed), or can be expressed as a fusion protein. Methods of expressing and purifying antibodies and antigen binding fragments are known and further described herein (see, e.g., Al-Rubeai (ed), *Antibody Expression and Production*, Springer Press, 2011). An immunoadhesin can also be expressed. Thus, in some examples, nucleic acids encoding a $V_H$ and $V_L$, and immunoadhesin are provided. The nucleic acid sequences can optionally encode a leader sequence.

To create a scFv the $V_H$- and $V_L$-encoding DNA fragments can be operatively linked to another fragment encoding a flexible linker, e.g., encoding the amino acid sequence (Gly$_4$-Ser)$_3$, such that the $V_H$ and $V_L$ sequences can be expressed as a contiguous single-chain protein, with the $V_L$ and $V_H$ domains joined by the flexible linker (see, e.g., Bird et al., *Science* 242:423-426, 1988; Huston et al., *Proc. Natl. Acad. Sci. USA* 85:5879-5883, 1988; McCafferty et al., *Nature* 348:552-554, 1990; Kontermann and Dubel (Ed), Antibody Engineering, Vols. 1-2, 2$^{nd}$ Ed., Springer Press, 2010; Harlow and Lane, *Antibodies: A Laboratory Manual*, 2$^{nd}$, Cold Spring Harbor Laboratory, New York, 2013,). Optionally, a cleavage site can be included in a linker, such as a furin cleavage site.

The nucleic acid encoding the $V_H$ and/or the $V_L$ optionally can encode an Fc domain (immunoadhesin). The Fc domain can be an IgA, IgM or IgG Fc domain. The Fc domain can be an optimized Fc domain, as described in U.S. Published Patent Application No. 20100/093979, incorporated herein by reference. In one example, the immunoadhesin is an IgG$_1$ Fc. In one example, the immunoadhesin is an IgG$_3$ Fc.

The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to matrilin-3 and to another molecule, such as a chondrogenesis biomarker. The encoded $V_H$ and $V_L$ optionally can include a furin cleavage site between the $V_H$ and $V_L$ domains.

Those of skill in the art are knowledgeable in the numerous expression systems available for expression of proteins including *E. coli*, other bacterial hosts, yeast, and various higher eukaryotic cells such as the COS, CHO, HeLa and myeloma cell lines.

One or more DNA sequences encoding the antibody or fragment thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. Hybridomas expressing the antibodies of interest are also encompassed by this disclosure.

The expression of nucleic acids encoding the proteins described herein can be achieved by operably linking the DNA or cDNA to a promoter (which is either constitutive or inducible), followed by incorporation into an expression cassette. The promoter can be any promoter of interest, including a cytomegalovirus promoter and a human T cell lymphotrophic virus promoter (HTLV)-1. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signal for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, at the minimum, a strong promoter to direct transcription, a ribosome binding site for translational initiation (internal ribosomal binding sequences), and a transcription/translation terminator. For *E. coli*, this can include a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or matrilin-3 binding fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). One of skill in the art can readily use an expression systems such as plasmids and vectors of use in producing proteins in cells including higher eukaryotic cells such as the COS, CHO, HeLa and myeloma cell lines.

Modifications can be made to a nucleic acid encoding a polypeptide described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation site, additional amino acids placed on either terminus to create conveniently located restriction sites, or additional amino acids (such as poly His) to aid in purification steps. In addition to recombinant methods, the antibodies, antigen binding fragments, and conjugates can also be constructed in whole or in part using standard peptide synthesis well known in the art.

Once expressed, the antibodies, antigen binding fragments, and conjugates can be purified according to standard procedures in the art, including ammonium sulfate precipitation, affinity columns, column chromatography, and the like (see, generally, Simpson ed., Basic methods in Protein Purification and Analysis: A laboratory Manual, Cold Harbor Press, 2008). The antibodies, antigen binding fragment, and conjugates need not be 100% pure. Once purified, partially or to homogeneity as desired, if to be used therapeutically, the polypeptides should be substantially free of endotoxin.

Methods for expression of the antibodies, antigen binding fragments, and conjugates, and/or refolding to an appropriate active form, from mammalian cells, and bacteria such as *E. coli* have been described and are well-known and are applicable to the antibodies disclosed herein. See, e.g., Harlow and Lane, *Antibodies: A Laboratory Manual*, 2$^{nd}$, Cold Spring Harbor Laboratory, New York, 2013, Simpson ed., Basic methods in Protein Purification and Analysis: A laboratory Manual, Cold Harbor Press, 2008, and Ward et al., *Nature* 341:544, 1989.

In addition to recombinant methods, the antibodies, antigen binding fragments, and/or conjugates can also be constructed in whole or in part using standard peptide synthesis. Solid phase synthesis of the polypeptides can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology*. Vol. 2: *Special Methods in Peptide Synthesis, Part A*. pp. 3-284; Merrifield et al., *J. Am. Chem. Soc.* 85:2149-2156, 1963, and Stewart et al., *Solid Phase Peptide Synthesis*, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N, N'-dicylohexylcarbodimide) are well known in the art.

E. Therapeutic Methods, Methods of Detection, and Compositions

A therapeutically effective amount of an antibody or antigen binding fragment that specifically binds matrilin-3, or conjugate thereof (such as a conjugate including a chondrogenic agent or anti-arthritis agent), or a nucleic acid molecule or vector encoding such a molecule, or a composition including such molecules, can be administered to a subject to increase height and/or to treat or inhibit a cartilage disorder and/or treat or inhibit arthritis (such as rheumatoid arthritis) in a subject, for example to treat or inhibit a growth plate cartilage disorder (such as a skeletal dysplasia, or short stature) or an articular cartilage disorder (such as osteoarthritis). In these applications, a therapeutically effective amount of the antibody, antigen binding fragment, or conjugate (e.g., that specifically binds matrilin-3), or a nucleic acid molecule or vector encoding such a molecule, or a composition including such molecules is administered to a subject in an amount and under conditions sufficient to form an immune complex with matrilin-3, thereby treating or inhibiting the cartilage disorder in the subject, for example, by increasing chondrogenesis in cartilage of the subject (such as growth plate cartilage or articular cartilage). A subject can be selected for treatment that has, is suspected of having, or is at risk of developing, a cartilage disorder, such as a growth plate cartilage disorder (e.g., a skeletal dysplasia, or short stature) or an articulate cartilage disorder (e.g., osteoarthritis). Subjects that can benefit from the disclosed methods include human and veterinary subjects.

The therapeutically effective amount will depend upon the severity of the disease and the general state of the patient's health. A therapeutically effective amount is that which provides either subjective relief of a symptom(s) or an objectively identifiable improvement as noted by the clinician or other qualified observer. In one embodiment, a therapeutically effective amount is the amount necessary to increase chondrogenesis in the cartilage (such as growth plate cartilage or articular cartilage) of a subject, or the amount that effectively treats or inhibits, or effectively reduces a sign or a symptom of, a cartilage disorder in a subject (such as a skeletal dysplasia, short stature, or osteoarthritis). The therapeutically effective amount of the agents administered can vary depending upon the desired effects and the subject to be treated.

The cartilage disorder or arthritis does not need to be completely eliminated for the method to be effective. For example, a disclosed method of treating or inhibiting a cartilage disorder or arthritis can decrease the cartilage disorder or arthritis by a desired amount, for example by at least 10%, at least 20%, at least 50%, at least 60%, at least 70%, at least 80%, at least 90%, at least 95%, at least 98%, or even at least 100% (elimination of all signs and symptoms of the cartilage disorder or arthritis), as compared to the cartilage disorder or arthritis in the absence of the treatment.

In some embodiments, a disclosed method of treating or inhibiting a cartilage disorder can increase the longitudinal growth of a subject with a cartilage disorder as compared the longitudinal growth in the absence of the treatment, such as an increase of at least at least 10%, at least 20%, at least 50%, at least 60%, at least 70%, at least 80%, at least 90%, at least 100%, at least 150%, at least 200%, at least 300%, at least 400, or at least 500% in the longitudinal growth of the subject as compared to the longitudinal growth in the absence of the treatment.

In some embodiments, a method of increasing chondrogenesis in cartilage tissue is provided. The methods include contacting the cartilage tissue with a therapeutically effective amount of an antibody or antigen binding fragment that specifically binds matrilin-3, or conjugate thereof (such as a conjugate including a chondrogenic agent), or a nucleic acid molecule or vector encoding such a molecule, or a composition including such molecules. In one non-limiting example, the cartilage tissue is contacted with a conjugate including a chondrogenic agent linked to an antibody or antigen binding fragment that specifically binds matrilin-3. The cartilage tissue can also be contacted with one or more additional agents, such as described herein for combination therapies. The cartilage tissue can be in vivo or in vitro. In some embodiments, chondrogenesis in the cartilage tissue is increased by at least 10%, at least 20%, at least 50%, at least 60%, at least 70%, at least 80%, at least 90%, at least 100%, at least 200%, at least 300%, at least 400% or even at least 500% compared to control conditions.

Also provided is a method of detecting matrilin-3 expression in vitro or in vivo. In one example, expression of matrilin-3 is detected in a biological sample, and can be used to detect cartilage tissue in a subject or in a sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. The method of detection can include contacting a cell or sample, or administering to a subject, an antibody or antigen binding fragment that specifically binds to matrilin-3, or conjugate there of (e.g. a conjugate including a detectable marker) under conditions sufficient to form an immune complex, and detecting the immune complex (e.g., by detecting a detectable marker conjugated to the antibody or antigen binding fragment.

Dosages and Frequency of Dosing

A therapeutically effective amount of an antibody or antigen binding fragment that specifically binds matrilin-3, or conjugate thereof (such as a conjugate including a chondrogenic agent or anti-arthritis agent), or a nucleic acid molecule or vector encoding such a molecule, or a composition including such molecules, can be readily ascertained by one skilled in the art, using publicly available materials and procedures. For example, the amount of an agent used for therapy should induce an increase in chondrogenesis and/or longitudinal growth of the patient compared to control conditions. In some embodiments, the therapy induces an increase in longitudinal growth compared to established growth patterns of children ages 0-17 years with a skeletal dysplasia, or short stature, or other cartilage disorder. Established growth patterns of such subjects are known, and can be obtained, for example, from established height for age, head circumference, and segmental growth (Horton et al., Standard growth curves for achondroplasia, J. Pediatr., 93: 435-8 (1978, incorporated by reference herein)).

The dosing frequency for a particular individual may vary depending upon various factors, including the disorder being treated and the condition and response of the individual to the therapy. In certain embodiments, a pharmaceutical composition containing the antibody or antigen binding fragment that specifically binds matrilin-3, or conjugate thereof (such as a conjugate including a chondrogenic agent), or a nucleic acid molecule or vector encoding such a molecule, is administered to a subject about one time per day, one time per two days, one time per three days, or one time per week. In one embodiment, for treatment of cartilage disorders (e.g., skeletal dysplasias, including achondroplasia and short stature), a daily or weekly dose of such therapeutic agents is administered to patients until and/or through adulthood.

Data obtained from cell culture assays and animal studies can be used to formulate a range of dosage for use in humans. The dosage normally lies within a range of circulating concentrations that include the $ED_{50}$, with little or minimal toxicity. The dosage can vary within this range depending upon the dosage form employed and the route of administration utilized. The therapeutically effective dose can be determined from cell culture assays and animal studies.

In certain embodiments, the antibody or antigen binding fragment that specifically binds matrilin-3, or conjugate thereof (such as a conjugate including a chondrogenic agent), or a nucleic acid molecule or vector encoding such a molecule, or a composition including such molecules, is administered at a dose in the range of from about 5 or 10 nmol/kg to about 300 nmol/kg, or from about 20 nmol/kg to about 200 nmol/kg, or at a dose of about 5, 10, 15, 20, 25, 30, 35, 40, 45, 50, 55, 60, 65, 70, 75, 80, 85, 90, 95, 100, 110, 120, 125, 130, 140, 150, 160, 170, 175, 180, 190, 200, 210, 220, 230, 240, 250, 260, 270, 280, 290, 300, 350, 400, 450, 500, 750, 1000, 1250, 1500, 1750 or 2000 nmol/kg, or at a dose of about 5, 10, 20, 30, 40, 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950 or 1000 ug/kg, or about 1, 1.25, 1.5, 2, 2.5, 3, 3.5, 4, 4.5, 5, 5.5, 6, 6.5, 7, 7.5, 8, 8.5, 9, 9.5 or 10 mg/kg, or other dose deemed appropriate by the treating physician. The doses described herein can be administered according to the dosing frequency/frequency of administration described herein, including without limitation daily, 2 or 3 times per week, weekly, every 2 weeks, every 3 weeks, monthly, etc.

In some embodiments, a disclosed therapeutic agent is administered so as to allow for periods of growth (e.g., chondrogenesis), followed by a recovery period (e.g., osteogenesis). For example, the therapeutic agent may be administered intravenously, subcutaneously or by another mode daily or multiple times per week for a period of time, followed by a period of no treatment, then the cycle is repeated. In some embodiments, the initial period of treatment (e.g., administration of the therapeutic agent daily or multiple times per week) is for 3 days, 1 week, 2 weeks, 3 weeks, 4 weeks, 5 weeks, 6 weeks, 7 weeks, 8 weeks, 9 weeks, 10 weeks, 11 weeks or 12 weeks. In a related embodiment, the period of no treatment lasts for 3 days, 1 week, 2 weeks, 3 weeks or 4 weeks. In certain embodiments, the dosing regimen of the therapeutic agent is daily for 3 days followed by 3 days off; or daily or multiple times per week for 1 week followed by 3 days or 1 week off; or daily or multiple times per week for 2 weeks followed by 1 or 2 weeks off; or daily or multiple times per week for 3 weeks followed by 1, 2 or 3 weeks off; or daily or multiple times per week for 4, 5, 6, 7, 8, 9, 10, 11 or 12 weeks followed by 1, 2, 3 or 4 weeks off.

Modes of Administration

An antibody or antigen binding fragment that specifically binds matrilin-3, or conjugate thereof (such as a conjugate including a chondrogenic agent or anti-arthritis agent), or a nucleic acid molecule or vector encoding such a molecule, or a composition including such molecules, as well as additional agents, can be administered to subjects in various ways, including local and systemic administration, such as, e.g., by injection subcutaneously, intravenously, intra-arterially, intraperitoneally, intramuscularly, intradermally, or intrathecally. In an embodiment, a therapeutic agent are administered by a single subcutaneous, intravenous, intra-arterial, intraperitoneal, intramuscular, intradermal or intrathecal injection once a day.

The therapeutic agent can also be administered by direct injection at or near the site of disease. Further, the therapeutic agent can be administered by implantation of a depot at the target site of action (e.g., an abnormal or dysplasic cartilage). The therapeutic agent may also be administered orally in the form of microspheres, microcapsules, liposomes (uncharged or charged (e.g., cationic)), polymeric microparticles (e.g., polyamides, polylactide, polyglycolide, poly(lactide-glycolide)), microemulsions, and the like.

A further method of administration is by osmotic pump (e.g., an Alzet pump) or mini-pump (e.g., an Alzet mini-osmotic pump), which allows for controlled, continuous and/or slow-release delivery of the therapeutic agent or pharmaceutical composition over a pre-determined period. The osmotic pump or mini-pump can be implanted subcutaneously, or near the target site (e.g., the long bones of limbs, the growth plate, etc.).

It will be apparent to one skilled in the art that the therapeutic agent or compositions thereof can also be administered by other modes. Determination of the most effective mode of administration of the therapeutic agent or compositions thereof is within the skill of the skilled artisan. The therapeutic agent can be administered as pharmaceutical formulations suitable for, e.g., oral (including buccal and sublingual), rectal, nasal, topical, pulmonary, vaginal or parenteral (including intramuscular, intraarterial, intrathecal, subcutaneous and intravenous) administration, or in a form suitable for administration by inhalation or insufflation. Depending on the intended mode of administration, the pharmaceutical formulations can be in the form of solid, semi-solid or liquid dosage forms, such as tablets, suppositories, pills, capsules, powders, liquids, suspensions, emulsions, creams, ointments, lotions, and the like. The formulations can be provided in unit dosage form suitable for single administration of a precise dosage. The formulations comprise an effective amount of a therapeutic agent, and one or more pharmaceutically acceptable excipients, carriers and/or diluents, and optionally one or more other biologically active agents.

Combination Therapy

In one embodiment, the antibody or antigen binding fragment that specifically binds matrilin-3, or conjugate thereof (such as a conjugate including a chondrogenic agent), or a nucleic acid molecule or vector encoding such a molecule, or a composition including such molecules can be used in combination with one or more other active agents useful for treating, ameliorating or preventing a cartilage disorder such as, e.g., short stature. The other active agent(s) can enhance the effects of the therapeutic agent and/or exert other pharmacological effects in addition to those of the therapeutic agent. Non-limiting examples of active agents that can be used in combination with the therapeutic agent described herein are natriuretic peptides (e.g., BNP) and inhibitors (e.g., antagonists) of peptidases and proteases (e.g., NEP and furin), NPR-C and tyrosine kinases (e.g., FGFR-3).

Co-use of a tyrosine kinase inhibitor can accentuate the therapeutic effects by inhibiting the tyrosine kinase receptor FGFR-3, a negative regulator of chondrogenesis. Non-limiting examples of tyrosine kinase inhibitors include those disclosed in U.S. Pat. Nos. 6,329,375 and 6,344,459, which are incorporated by reference herein.

To achieve the appropriate therapeutic outcome in the combination therapies, one would generally administer to the subject the antibody or antigen binding fragment that specifically binds matrilin-3, or conjugate thereof (such as a conjugate including a chondrogenic agent), or a nucleic acid molecule or vector encoding such a molecule, or a composition including such molecules and other therapeutic(s) in a combined amount effective to produce the desired therapeutic outcome (e.g., chondrogenesis and/or increased linear growth). This process may involve administering the antibody or antigen binding fragment that specifically binds matrilin-3, or conjugate thereof (such as a conjugate including a chondrogenic agent), or a nucleic acid molecule or vector encoding such a molecule, or a composition including such molecules, and other therapeutic agent(s) at the same time. Simultaneous administration can be achieved by administering a single composition or pharmacological formulation that includes multiple agent(s). Alternatively, the other therapeutic agent(s) can be taken separately at about the same time as a pharmacological formulation (e.g., tablet, injection or drink) of the antibody or antigen binding fragment that specifically binds matrilin-3, or conjugate thereof (such as a conjugate including a chondrogenic agent), or a nucleic acid molecule or vector encoding such a molecule, or a composition including such molecules.

In other alternatives, administration of the antibody or antigen binding fragment that specifically binds matrilin-3, or conjugate thereof (such as a conjugate including a chondrogenic agent), or a nucleic acid molecule or vector encoding such a molecule, or a composition including such molecules can precede or follow administration of the other therapeutic agent(s) by intervals ranging from minutes to hours. In embodiments where the other therapeutic agent(s) and the antibody or antigen binding fragment that specifically binds matrilin-3, or conjugate thereof (such as a conjugate including a chondrogenic agent), or a nucleic acid molecule or vector encoding such a molecule, or a composition including such molecules are administered separately, one would generally ensure that the multiple agents are administered within an appropriate time of one another so that each agent can exert, synergistically or additively, a beneficial effect on the patient. For example, one can administer the antibody or antigen binding fragment that specifically binds matrilin-3, or conjugate thereof (such as a conjugate including a chondrogenic agent), or a nucleic acid molecule or vector encoding such a molecule, or a composition including such molecules within about 0.5-6 hours (before or after) of the other therapeutic agent(s). In one embodiment, the antibody or antigen binding fragment that specifically binds matrilin-3, or conjugate thereof (such as a conjugate including a chondrogenic agent), or a nucleic acid molecule or vector encoding such a molecule, or a composition including such molecules is administered within about 1 hour (before or after) of the other therapeutic agent(s).

The combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the compounds are administered or delivered sequentially, for example by different injections in separate syringes. In general, during alternation, an effective dosage of each active ingredient is administered sequentially, i.e. serially, whereas in combination therapy, effective dosages of two or more active ingredients are administered together.

Identifying and Monitoring Patient Populations

Protocols can be established to identify subjects suitable for therapy using the antibody or antigen binding fragment that specifically binds matrilin-3, or conjugate thereof (such as a conjugate including a chondrogenic agent or an anti-arthritis agent), or a nucleic acid molecule or vector encoding such a molecule, or a composition including such molecules and to determine whether a given patient is responsive to such therapy. For example, for treatment of cartilage disorders, indicators of growth can be measured, such as height, long bone growth measurements in utero or postnatal. The ameliorating effect on skeletal deformity can be assessed by physical examination and clinical imaging methods, such as radiographs, CT scans, MRI scans, and ultrasounds. In addition, measurements of bone growth biomarkers such as CNP, cGMP, Collagen II, osteocalcin, and Proliferating Cell Nuclear Antigen (PCNA) may serve as a useful marker for efficacy.

Cartilage-specific analytes (or cartilage-associated markers) can also be measured to assess therapeutic efficacy. For example, fragments of cleaved collagen type II are a cartilage-specific marker for cartilage turnover. Type II collagen is the major organic constituent of cartilage and fragments of type II collagen (cleaved collagen) are released into circulation, and subsequently secreted into the urine, following cartilage turnover. Cartilage turnover precedes new bone formation.

A biomarker for bone formation which can be measured is N-terminal propeptides of type I procollagen (PINP). The synthesis of type I collagen is an important step in bone formation, as type I collagen is the major organic component in bone matrix. During collagen synthesis, propeptides are released from the procollagen molecule and can be detected in serum. Other potential biomarkers for cartilage formation and growth include aggrecan chondroitin sulfate (cartilage-specific marker for cartilage turnover), and propeptides of type TT collagen (cartilage-specific marker for cartilage formation). Cartilage-associated biomarkers can be measured, e.g., in serum from efficacy/pharmacodynamic in vivo studies and from the conditioned media of ex vivo studies, using commercially available kits.

In one embodiment, the level of at least one cartilage-associated biomarker is assayed or measured in a subject that has been administered the antibody or antigen binding fragment that specifically binds matrilin-3, or conjugate thereof (such as a conjugate including a chondrogenic agent), or a nucleic acid molecule or vector encoding such a molecule, or a composition including such molecules in order to monitor the effects of the therapeutic agent on bone and cartilage formation and growth in vivo. For example, an increase in the level of at least one cartilage-associated biomarker may indicate that administration of the therapeutic agent has a positive effect on chondrogenesis or bone growth and is a useful treatment for skeletal dysplasias and other cartilage disorders. Exemplary bone- or cartilage-associated biomarkers include, but are not limited to, CNP (e.g, endogenous levels of CNP), cGMP, propeptides of collagen type II and fragments thereof, collagen type II and fragments thereof, osteocalcin, proliferating cell nuclear antigen (PCNA), propeptides of type I procollagen (PINP) and fragments thereof, collagen type I and fragments thereof, aggrecan chondroitin sulfate, and alkaline phosphatase.

In an embodiment, biomarkers are measured by obtaining a biological sample from a subject who will be administered, is being administered or has been administered one or more of an antibody or antigen binding fragment that specifically binds matrilin-3, or conjugate thereof (such as a conjugate including a chondrogenic agent), or a nucleic acid molecule or vector encoding such a molecule, or a composition including such molecules. Biomarkers can be measured using techniques known in the art, including, but not limited to, Western Blot, enzyme linked immunosorbant assay (ELISA), and enzymatic activity assay. The biological sample can be blood, serum, urine, or other biological fluids.

Additional aspects and details of the disclosure will be apparent from the following examples, which are intended to be illustrative rather than limiting.

Compositions

Compositions are provided that include one or more antibodies, antigen binding fragments (such as an antibody or antigen binding fragment that specifically binds to matrilin-3), or conjugates thereof (such as a conjugate including a chondrogenic agent or anti-arthritis agent linked to an antibody or antigen binding fragment that specifically binds matrilin-3), or nucleic acid molecules or vectors encoding such molecules in a carrier (such as a pharmaceutically acceptable carrier). The compositions can be prepared in unit dosage forms for administration to a subject. The amount and timing of administration are at the discretion of the treating clinician to achieve the desired outcome. The compositions can be formulated for systemic (such as intravenous) or local (such as intra-cartilage) administration. In one example, a disclosed antibody, antigen binding fragment, or conjugate, is formulated for parenteral administration, such as intravenous administration. Compositions including a conjugate, antibody or antigen binding fragment as disclosed herein are of use, for example, for the treatment of cartilage disorders as well as for the detection of cartilage. In some examples, the compositions are useful for the treatment of a cartilage disorder such as a skeletal dysplasia, short stature, or osteoarthritis.

In some embodiments, the compositions comprise an antibody, antigen binding fragment, or conjugate thereof, in at least about 70%, 75%, 80%, 85%, 90%, 95%, 96%, 97%, 98% or 99% purity. In certain embodiments, the compositions contain less than about 10%, 5%, 4%, 3%, 2%, 1% or 0.5% of macromolecular contaminants, such as other mammalian (e.g., human) proteins.

The compositions for administration can include a solution of the conjugate, antibody or antigen binding fragment dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody or antigen binding fragment or conjugate in these formulations can vary widely, and will be selected primarily based on fluid volumes, viscosities, body weight and the like in accordance with the particular mode of administration selected and the subject's needs. Actual methods of preparing such dosage forms are known, or will be apparent, to those skilled in the art.

A typical composition for intravenous administration includes about 0.01 to about 30 mg/kg of antibody or antigen binding fragment or conjugate per subject per day (or the corresponding dose of a conjugate including the antibody or antigen binding fragment). Actual methods for preparing administrable compositions will be known or apparent to those skilled in the art and are described in more detail in such publications as *Remington's Pharmaceutical Science*, 19th ed., Mack Publishing Company, Easton, Pa. (1995). In some embodiments, the composition can be a liquid formulation including one or more antibodies, antigen binding fragments (such as an antibody or antigen binding fragment that specifically binds to matrilin-3), or conjugates thereof (such as a conjugate including a chondrogenic agent linked to an antibody or antigen binding fragment that specifically binds matrilin-3), or nucleic acid molecules or vectors encoding such molecules in a concentration range from about 0.1 mg/ml to about 20 mg/ml, or from about 0.5 mg/ml to about 20 mg/ml, or from about 1 mg/ml to about 20 mg/ml, or from about 0.1 mg/ml to about 10 mg/ml, or from about 0.5 mg/ml to about 10 mg/ml, or from about 1 mg/ml to about 10 mg/ml.

Therapeutic agents such as antibodies, antigen binding fragments, or conjugates may be provided in lyophilized form and rehydrated with sterile water before administration, although they are also provided in sterile solutions of known concentration. The antibody or antigen binding fragment or conjugate solution is then added to an infusion bag containing 0.9% sodium chloride, USP, and in some cases administered at a dosage of from 0.5 to 15 mg/kg of body weight. Considerable experience is available in the art in the administration of antibody or antigen binding fragment and conjugate drugs; for example, antibody drugs have been marketed in the U.S. since the approval of RITUXAN® in 1997. The agents can be administered by slow infusion, rather than in an intravenous push or bolus. In one example, a higher loading dose is administered, with subsequent, maintenance doses being administered at a lower level. For example, an initial loading dose of 4 mg/kg antibody or antigen binding fragment (or the corresponding dose of a conjugate including the antibody or antigen binding fragment) may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the antibody or antigen binding fragment or conjugate compositions disclosed herein. Various degradable and nondegradable polymeric matrices for use in controlled drug delivery are known in the art (Langer, *Accounts Chem. Res.* 26:537-

542, 1993). For example, the block copolymer, poloxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

F. Kits

Kits are also provided. For example, kits for treating a subject with one or more antibodies, antigen binding fragments (such as an antibody or antigen binding fragment that specifically binds to matrilin-3), or conjugates thereof (such as a conjugate including a chondrogenic agent linked to an antibody or antigen binding fragment that specifically binds matrilin-3), nucleic acid molecules or vectors encoding such molecules, or compositions including such molecules. The kits will typically include a disclosed antibody, antigen binding fragment, conjugate, nucleic acid molecule, or composition as disclosed herein. More than one of the disclosed antibodies, antigen binding fragments, conjugates, nucleic acid molecules, or compositions can be included in the kit.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, or compositions. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of the antibodies, antigen binding fragments, conjugates, nucleic acid molecules, or compositions included in the kit. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

EXAMPLES

The following examples are provided to illustrate particular features of certain embodiments, but the scope of the claims should not be limited to those features exemplified.

Example 1

Human Monoclonal Antibodies and Fragments Thereof Targeting Matrilin-3 in Growth Plate Cartilage This example illustrates monoclonal antibodies and antigen binding fragments thereof for targeting therapeutics to growth plate cartilage.

Abstract

Growth plate function can be severely impaired in many acquired systemic disorders, and in genetic disorders, including skeletal dysplasias, in which the bones are typically short and malformed, causing disability. Current medical therapies have limited efficacy for severe disease, with doses limited by effects on tissues other than growth plate cartilage. Recent studies have identified many paracrine factors that act in the growth plate to positively regulate chondrogenesis, and therefore might be used therapeutically if they could be targeted to growth plate cartilage. Similarly, targeting growth-promoting endocrine factors, such as growth hormone and insulin-like growth factor-I, specifically to the growth plate could potentially enhance therapeutic efficacy while diminishing adverse effects on non-target tissues. Using yeast display technology, single-chain variable antibody fragments were identified that bind with high affinity to human and mouse matrilin-3, a protein expressed specifically in cartilage tissue. They also bound with high specificity to cartilage homogenates and to cartilage structures in mouse embryo sections. When injected intravenously in mice, these antibody fragments homed to cartilage and were not detectable in other tissues. Coupling these cartilage-binding antibodies to endocrine and paracrine signaling molecules that promote chondrogenesis can allow therapy targeted specifically to growth plate, and also articular cartilage, thereby opening up broad new pharmacological approaches to targeted drug delivery to deliver drugs to the growth plate or articular cartilage, for example to increase height and/or to treat cartilage disorders, such as skeletal dysplasias, including achondroplasia, short stature, and joint diseases such as osteoarthritis.

Introduction

The growth plate is a specialized cartilage structure present near the ends of tubular bones and vertebrae. The primary function of the growth plate is to generate new cartilage, which is then remodeled into bone tissue, resulting in bone elongation. In this process, termed endochondral bone formation, chondrocytes in the growth plate undergo rapid proliferation followed by terminal differentiation into hypertrophic chondrocytes. The newly formed cartilage is invaded by blood vessels and bone cells, which convert the cartilage into bone tissue. The net result is that new bone is formed adjacent to the growth plate, leading to longitudinal bone growth. Because body length is largely determined by the lengths of long bones and vertebrae, endochondral bone formation at the growth plates is the underlying mechanism responsible for increasing height during childhood.

Longitudinal bone growth is a complex process which requires multiple intracellular, endocrine, and paracrine pathways to function normally. Consequently, mutations in hundreds of genes that are required for growth plate function give rise to disorders of skeletal growth, including the skeletal dysplasias, in which the bones are typically short and malformed, often causing major disability. In addition to genetic disorders, acquired endocrine, nutritional, or inflammatory disorders can also impair bone growth at the growth plate, resulting in severe short stature.

Current treatment options for growth disorders are limited. Recombinant human growth hormone (GH) is used for both GH-deficiency and certain non-GH-deficient causes of short stature (Richmond, *Current Indications for Growth Hormone Therapy* Vol. 18, Karger, 2010). However, the efficacy of GH treatment is often suboptimal. Even for growth hormone deficiency, the reported adult heights achieved in the majority of patients after GH supplementation remain below the normal range (Ranke, et al. *Horm Res Paediatr,* 51-67, 2013). In non-GH deficient conditions, including skeletal dysplasias, the efficacy is typically even more partial (Ranke. Pediatrician 14, 178-182, 1987). Moreover, GH treatment carries a risk of increased intracranial pressure (Wilson, et al. *J Pediatr* 143, 415-421, 2003), slipped capital femoral epiphysis (Wang, et al. *J Formos Med Assoc* 106, S46-50, 2007; and Darendeliler, et al. *Horm Res* 68 Suppl 5, 41-47, 2007), insulin resistance (Yuen, et al. *Diabet Med,* 30.6, 651-663, 2013; and Canete, et al. *Eur J Endocrinol* 167, 255-260, 2012), and possibly type II diabetes mellitus (Cutfield, et al. *Lancet* 355, 610-613, 2000). Endogenous GH excess increases the risk of colon cancer; whether or not childhood growth hormone treatment raises cancer risk in adulthood is not known (Swerdlow, et al. *Lancet* 360, 273-277, 2002). Because systemic administration of GH has limited efficacy and significant known and potential adverse effects, better treatments for growth plate disorders are needed.

Recent studies have identified many paracrine factors that positively regulate growth plate chondrogenesis and therefore might be used therapeutically, including Indian Hedgehog (IHH) (Chau, et al. *J Mol Endocrinol* 47, 99-107, 2011; Kobayashi, et al. *J Clin Invest* 115, 1734-1742, 2005; Kronenberg. *Ann N Y Acad Sci* 1068, 1-13, 2006; Maeda, et al. *Proc Natl Acad Sci USA* 104, 6382-6387, 2007; Long, et al. *Dev Biol* 298, 327-333, 2006; Amizuka, et al. *J Cell Biol* 126, 1611-1623, 1994; Long, et al. *Development* 128, 5099-5108, 2001; Mak, et al. *Development* 135, 1947-1956, 2008), bone morphogenetic proteins (BMPs) (De Luca, et al. *Endocrinology* 142, 430-436, 2001; Nilsson, et al. *J Endocrinol* 193, 75-84, 2007; Kobayashi, et al. *Proc Natl Acad Sci USA* 102, 18023-18027, 2005; Yoon, et al. *Development* 133, 4667-4678, 2006; Wu, et al. *J Biol Chem* 286, 24726-24734, 2011; Yoon, et al. *Proc Natl Acad Sci USA* 102, 5062-5067, 2005), C-type natriuretic peptide (CNP) (Mericq, et al. *Pediatr Res* 47, 189-193, 2000; Agoston, et al. *BMC Dev Biol* 7, 18, 2007; Olney, et al. *J Clin Endocrinol Metab* 92, 4294-4298, 2007; Olney, et al. *J Clin Endocrinol Metab* 91, 1229-1232, 2006; Teixeira, et al. *Dev Biol* 319, 171-178, (2008); Woods, et al. *Endocrinology* 148, 5030-5041, 2007), and WNTs (Andrade, et al. *Bone* 40, 1361-1369, 2007; Hartmann, et al. *Development* 127, 3141-3159, 2000; Yates, et al. *DNA Cell Biol* 24, 446-457, 2005; Yang, et al. *Development* 130, 1003-1015, 2003; Akiyama, et al. *Genes Dev* 18, 1072-1087, 2004). However, the development of these molecules into effective treatment has been hampered by their mechanism of action; these growth factors are produced locally and act locally in the growth plate, and thus do not lend themselves to systemic therapeutic approaches. Disclosed herein are methods of targeting these locally-acting molecules to the growth plate by linking them to cartilage-binding proteins, such as antibody fragments.

When administered systemically, these hybrid molecules would be preferentially taken up by growth plate cartilage, and thus augment the therapeutic effect on the target organ while diminishing adverse effects due to action on other tissues.

Similarly, growth-promoting endocrine factors, such as GH and insulin-like growth factor-I can be linked to cartilage-binding polypeptides and thereby targeted to the growth plate. Targeted endocrine therapy could potentially enhance the therapeutic effects on chondrogenesis or bone growth and reduce effects on non-target tissues, thereby decreasing risks such as malignancy and diabetes mellitus. Besides treating growth plate disorders, cartilage-targeting polypeptides might also be applied to improve treatment of articular cartilage disorders.

As described below, proteins that home to cartilage tissue were identified. A yeast-displayed library of human antibody fragments was screened for high affinity binders to matrilin-3, a protein expressed with high tissue specificity in cartilage. Several antibody fragments were identified that bind with high affinity both to human and mouse matrilin-3, as well as to cartilage tissue in vitro. When these antibody fragments were administered to mice by tail-vein injection, they homed specifically to cartilage tissue. Coupling these antibody fragments to endocrine and paracrine factors that stimulate chondrogenesis could be used to direct these potent molecules specifically to cartilage tissue, providing important new therapeutic approaches to the treatment of growth plate and articular cartilage disorders.

Material and Methods

Selection of Extracellular Matrix Protein-Binding Antibody Fragments

Recombinant human and mouse matrilin-3 proteins (R&D Systems, Minneapolis, Minn.) that were biotinylated using an Avi-tag Specific Biotinylation kit (Aurora, Colo.) were used as the target for selection. In the first round of selection, approximately $5 \times 10^{10}$ cells from the naïve antibody library were incubated with 10 μg of biotinylated human matrilin-3 in 50 ml 0.1% bovine serum albumin (BSA)-phosphate-buffered saline (PBS), called PBSA, at room temperature for two hours with gentle rotation. Then, the mixture was washed three times with 0.1% PBSA to remove unbound antibody fragments. Biotinylated matrilin-3 together with bound antibody fragments were subsequently incubated with 100 μl of strepatavidin-conjugated microbeads (Milenvi Biotec, Auburn, Calif.) and loaded onto the AutoMACS system for sorting. Cells which display antibody fragments with high affinity to matrilin-3 were collected and later amplified in SDCAA Medium (20 g Dextrose, 6.7 g Difco yeast nitrogen base without amino acids, 5 g Bacto casamino acids, 5.4 g $Na_2HPO_4$ and 8.56 g $NaH_2PO_4$. $H_2O$ dissolved in 1 L of distilled water) at 250 rpm at 30° C. for 24 hours. After that, the culture was induced in SGCAA Medium (20 g Galactose, 20 g Raffinose, 1 g Dextrose, 6.7 g Difco yeast nitrogen base without amino acids, 5 g Bacto casamino acids, 5.4 g $Na_2HPO_4$ and 8.56 g $NaH_2PO_4$. $H_2O$ dissolved in 1 L of distilled water) at 250 rpm at 20° C. for 18 hours. The pool obtained was subjected to another round of selection for binding to human matrilin-3. To ensure sufficient diversity of antibody fragments for second and third rounds of screening, the input cell number was increased by 100 fold compared to the prior round of sorting.

For the third round of selection, His-Tagged recombinant mouse matrilin-3 was employed. The screening was carried out in a similar way to the previous two rounds of selection toward human matrilin-3. Finally, antibody fragments that bound to mouse matrilin-3 were pulled down by anti-His-tag antibody-conjugated microbeads. The yeast cells expressing antibody fragments that possess high binding affinity to human and mouse matrilin-3 proteins were collected.

Cloning of Extracellular Matrix Protein-Binding Antibody Fragments in Mammalian Vectors After the final round of sorting, DNA plasmids were extracted from the yeast cells using Yeast Plasmid Extraction kit (Zymo Research, Irvine, Calif.) and then transformed into 10G chemical competent *E. coli* (Lucigen, Middleton, Wis.) for further amplification. The scFv-encoding DNA inserts were double-digested with restriction enzyme SfiI and ligated to a modified pSecTagB vector, which bears the same set of SfiI sites and a downstream Fc-Avi tag.

Cell Culture

HEK293T cells were obtained from ATCC (Manassas, Va.), and maintained in Dulbecco's modified Eagle's Medium (DMEM) (Gibco, Grand Island, N.Y.) supplemented with 10% fetal calf serum (FCS) (v/v) (Gibco) and 1% penicillin-streptomycin (PS) (v/v) (Gibco) at 37° C. in a humidified atmosphere of 5% $CO_2$. FreeStyle 293-F cells (Invitrogen, Grand Island, N.Y.) were cultured in suspension in FreeStyle 293 Expression Medium (Gibco) shaking at 125 rpm at 37° C. in a humidified atmosphere of 8% $CO_2$.

Small-Scale Expression of Antibody Fragments in HEK293T Cells

HEK293T cells were seeded in 24-well plates at a density of $5\times10^4$ cells/well, and cultured at 37° C. in 5% $CO_2$ overnight. On the next day, 0.5 μg of DNA and 5 μl of PolyFect reagent (Qiagen, Valencia, Calif.) were suspended in serum-free, antibiotic-free DMEM to give a final volume of 30 μl, which was allowed to stand at room temperature for 10 minutes. Then, the mixture was introduced to the wells containing cultured cells and 375 μl of fresh medium. At 48 hours post-transfection, supernatant containing the secreted antibody fragments was collected for subsequent experiments.

Assessment of the Binding Ability and Specificity of Antibody Fragments

To assess the ability of the 36 selected clones of antibody fragments to bind to purified matrilin-3, 100 μl of human or mouse matrilin-3 protein (2 μg/ml) was coated onto 96-well plates at 4° C. overnight. To assess binding to cartilage and non-cartilaginous tissues, heart, liver, lung, kidney, spleen, small intestine, muscle, and distal femoral and proximal tibial growth plate were dissected from 4-day-old C57BL/6 mice and homogenized in protein lysis buffer (150 mM NaCl, 10 mM Tris-HCl, 5 mM EDTA (pH8.0), 1% Triton X-100, 0.1% SDS) at 4° C. Tissue debris was removed by centrifugation. 100 μl of tissue lysate was coated onto 96-well plates at 4° C. overnight. Each antibody clone was tested in triplicate wells. After blocking with 3% non-fat milk (200 μl/well), 50 μl of the culture supernatant was introduced to each well and incubated at room temperature for two hours. Supernatant from cells transfected with a non-specific antibody fragment was included as a negative control, while commercial anti-matrilin-3 antibody polyclonal antibody recognizing a 13-amino acid peptide from near the center of human matrilin-3 (Thermo Scientific, Rockford, Ill.) served as a positive control. The wells were then washed with 0.05% Tween-phosphate-buffered saline (PBST) four times and incubated with 50 μl of horseradish peroxidase (HRP)-conjugated anti-Fc antibody (Millipore, Temecula, Calif.) (diluted 1:5000 in 3% non-fat milk) at room temperature for one hour. Finally, tetramethybezidine (TMB) substrate reagent (eBioscience, San Diego, Calif.) was added for color development and absorbance was read at 450 nm.

Examination of Binding of Selected Antibody Fragments in Mouse Embryo Sections

10 μm cryosections of frozen E15 mouse embryos were equilibrated to room temperature for 30 minutes, fixed in acetone for 15 minutes, air-dried for 30 minutes, and then blocked with 1% FCS in PBS at room temperature for 1 hour. The sections were then incubated for 1 hour with 100 μl of the supernatant from transfected HEK293T cells expressing antibody fragments, washed with PBS for 5 minutes three times, incubated for 1 hour with 100 μl of HRP-conjugated anti-Fc antibody (1:2000 dilution in PBS containing 1% FCS), and washed with PBS for 5 minutes three times, all at room temperature. Binding of the selected antibody fragments to sections was detected using DAB substrate kit (Abcam, Cambridge, Mass.). An antibody fragment selected for binding to a protein of Dengue virus served as a negative control.

Large-Scale Expression of Selected Antibody Fragments in 293 FreeStyle-F Cells

For production and purification, antibody fragments were expressed in 293 FreeStyle-F, a suspension cell line which is adapted to serum-free medium and thus avoids serum IgG which may interfere with antibody fragment purification. Twenty-four hours before transfection, $3\times10^7$ 293 FreeStyle-F cells were resuspended in 28 ml FreeStyle 293 Expression Medium in a 250 ml Erlenmeyer flask on an orbital shaker rotating at 125 rpm, at 37° C. in 8% $CO_2$. On the day of transfection, 30 μg of DNA and 60 μl of 293fectin reagent (Qiagen) were diluted in 2 ml of Opti-MEM, and the mixture was incubated at room temperature for 20 minutes. Afterward, the mixture was introduced to a flask containing the 293 FreeStyle-F cells in 28 ml medium and shaken for 3 days to express soluble protein fragments. Supernatant was subsequently collected for antibody purification using protein A columns.

Purification of Antibody Fragments by Protein a Column

Protein A resin (GenScript, Piscataway, N.J.) slurry (2 ml) was packed into a glass column, and equilibrated with 50 ml of binding/washing buffer (0.15 M NaCl, 20 mM $Na_2HPO_4$, pH 8.0). Culture supernatant was loaded onto the column. Unbound proteins were washed away with 100 ml of binding/washing buffer. Bound antibodies were then eluted with 8 ml of elution buffer (100 mM acetic acid, pH 3.0). The eluate was neutralized by 1/10 volume of neutralization buffer (1 M Tris-HCl, pH 9.0) and dialyzed against 100 volumes of PBS at 4° C. overnight. The purity of the antibodies was checked by SDS-PAGE.

Measurement of the Binding Affinity of Antibody Fragments

To assess the binding affinity of the purified antibody fragments, 100 μl of human or mouse matrilin-3 protein (2 μg/ml) was coated onto 96-well plates at 4° C. overnight. Then, the wells were blocked with 200 μl of 3% non-fat milk in PBS at room temperature for 2 hours. 50 μl of different concentrations of antibody fragments 13, 22, and 26 (230 nM, 57.5 nM, 14.375 nM, 3.594 nM, 0.899 nM, 0.225 nM, 0.056 nM, 0.014 nM) was added to incubate with the target at room temperature for 2 hours. Duplicates were performed for each concentration of the selected antibody fragments. After binding, the wells were washed with 0.05% PBST 4 times and incubated with 50 μl of HRP-conjugated anti-Fc antibody (diluted 1:5000 in 3% non-fat milk) at room temperature for 1 hour. Lastly, TMB substrate reagent was introduced and absorbance was read at 450 nm.

Investigation of the In Vivo Homing Ability of Antibody Fragments

In order to evaluate whether the selected antibodies were able to home to growth plate cartilage, 50 µg of purified antibody fragments, diluted in 100 µl of sterile saline, was injected in 3-week-old C57BL/6 male mice intravenously. As control experiments, two groups of mice were injected with 100 µl of sterile saline or 50 µg (in 100 µl of sterile saline) of purified non-specific antibody fragment (selected for binding to a protein of Dengue virus). After 24 hours, tissues were harvested and homogenized in protein lysis buffer. Tissue debris was removed by centrifugation, and supernatant was collected for ELISA to check for the localization of the antibody fragments. Briefly, 100 µl of tissue lysate was coated in triplicate wells in 96-well plates at 4° C. overnight. Subsequent to blocking with 200 µl of 3% non-fat milk per well, 50 µl of HRP-conjugated anti-Fc antibody (diluted 1:5000 in 3% non-fat milk) was added to each well and incubated at room temperature for 1 hour. TMB substrate reagent was then introduced and the absorbance was read at 450 nm. For each organ or tissue in a particular group, statistical significance was assessed by ANOVA, followed by pairwise comparison the growth plate signal to other tissues, with Holm-Sidak correction for multiple comparisons. Comparison of the growth plate signal between different groups were done by Student t-test.

Results

Selection of Extracellular Matrix Protein-Specific Antibody Fragments

Antibody fragments were selected from a large yeast display single-chain fragment variable (scFv) library for binding to matrilin-3, an extracellular matrix protein specifically expressed in cartilage (Wagener, et al. *FEBS Lett* 413, 129-134, 1997; Burnam, et al. *J Abnorm Psychol* 84, 76-79, 1975; Klatt, et al. *J Biol Chem* 275, 3999-4006, 2000). The sorting was carried out against human recombinant matrilin-3 protein in the first two rounds and mouse recombinant matrilin-3 protein in the third round of panning to increase the likelihood that the resulting antibody fragments would bind both to mouse cartilage matrix for preclinical safety and efficacy evaluations and human cartilage matrix, for clinical applications. After three rounds of selection, the enriched library exhibited a striking increase in binding to matrilin-3 proteins of both species by flow cytometric analysis (FIG. 1A).

Binding of Antibody Fragments to Cartilage Matrix In Vitro

Figure 1B:
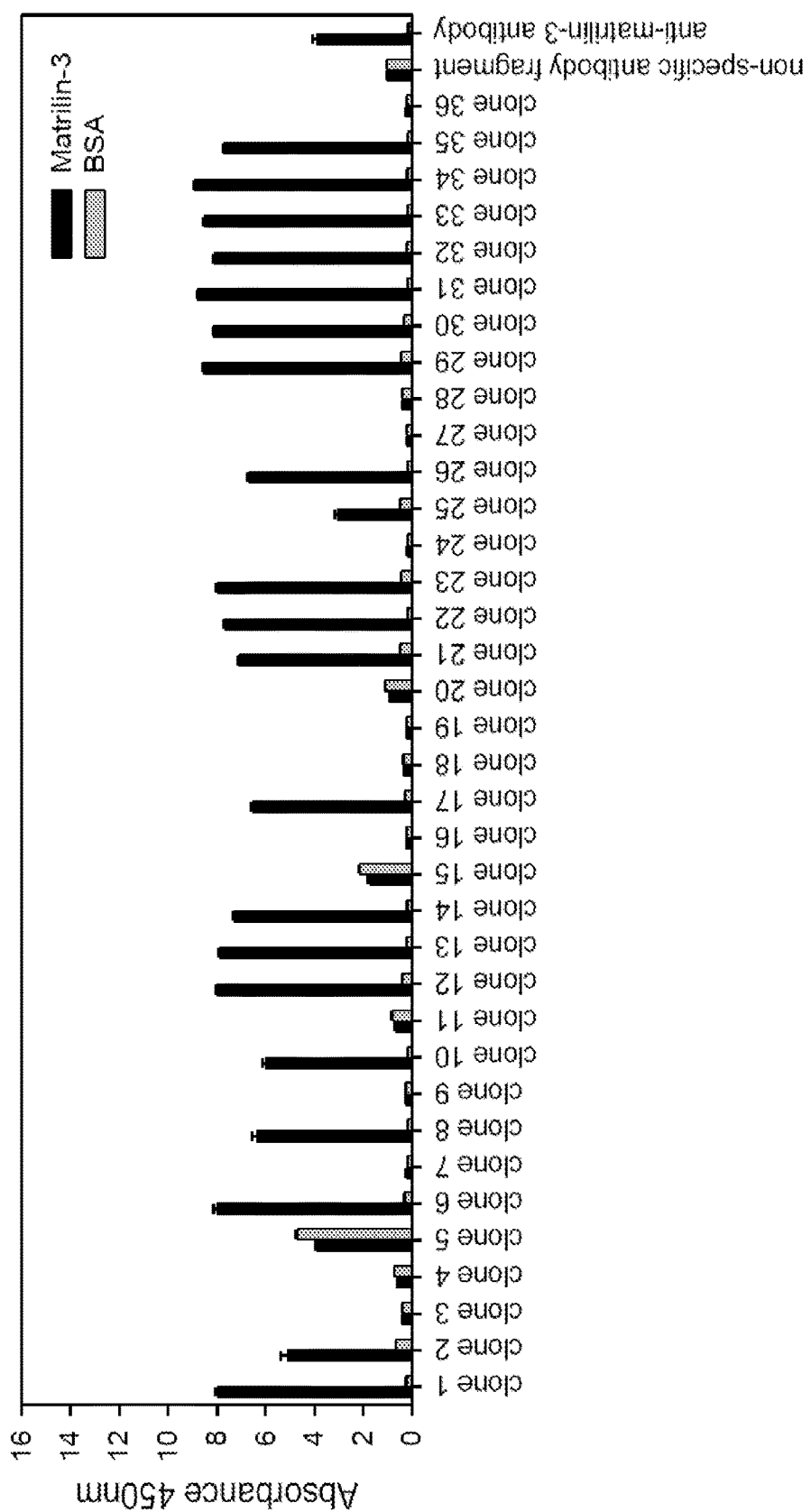
Figure 1C:
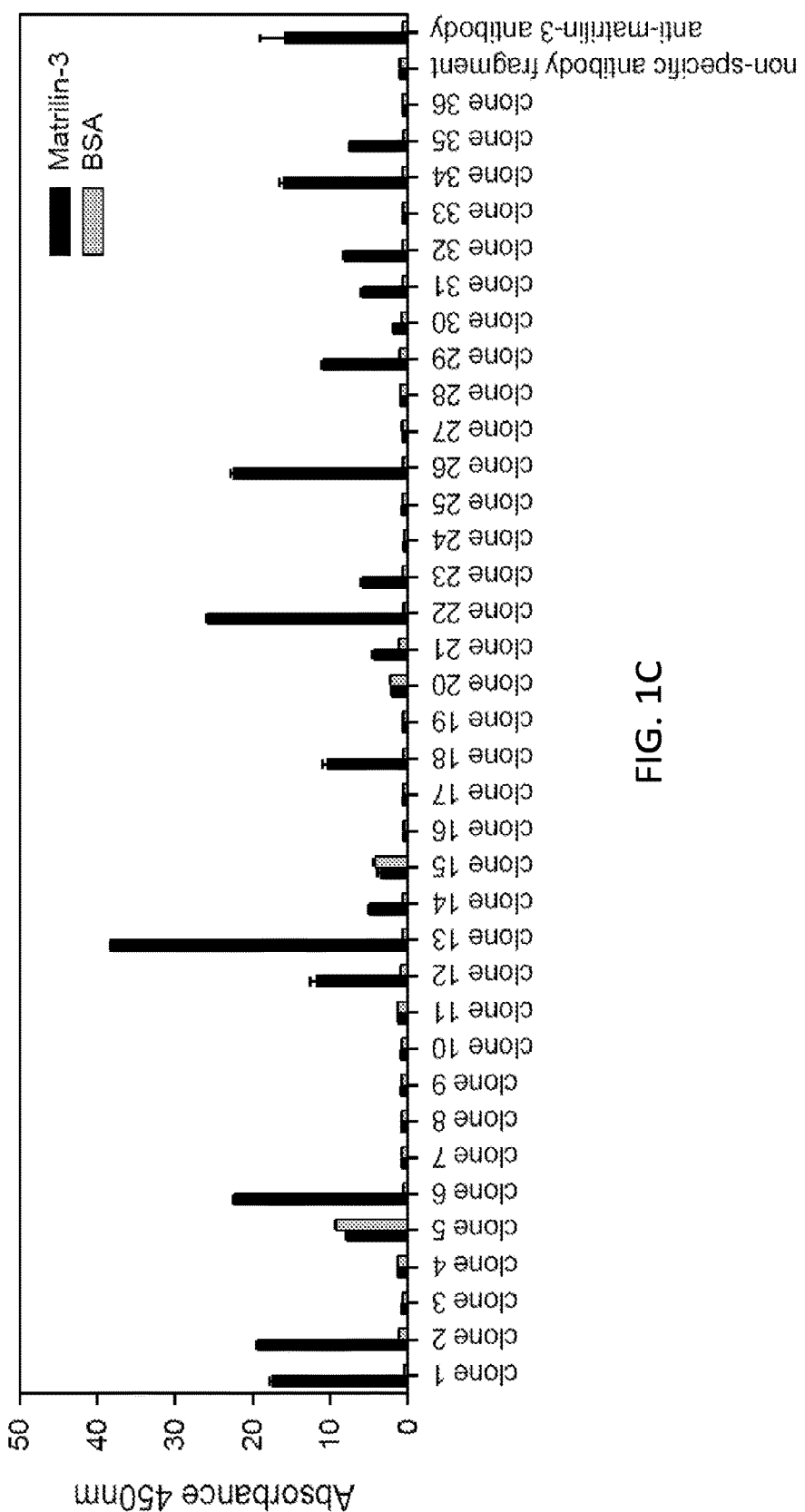

After the final round of selection, 36 yeast clones were randomly selected and the expression plasmids were isolated. The DNA sequences encoding the scFvs were then excised and subcloned into a mammalian expression vector pSecTagB, which was previously engineered to include a human Fc fragment-coding DNA sequence. The resulting construct consisted of a scFv antibody fragment fused with human IgG1 Fc fragment. This construct was subsequently transfected into HEK293T cells for 48 hours to express scFv-Fc proteins, and the ability of these 36 proteins to bind both human and mouse recombinant matrilin-3 was assessed by ELISA. Of these, 21 bound to human recombinant matrilin-3 (FIG. 1B), and 17 bound to mouse matrilin-3 (FIG. 1C), compared to bovine serum albumin and to a non-specific antibody fragment.

Binding of Antibody Fragments to Cartilage Extracts In Vitro

Figure 1D:
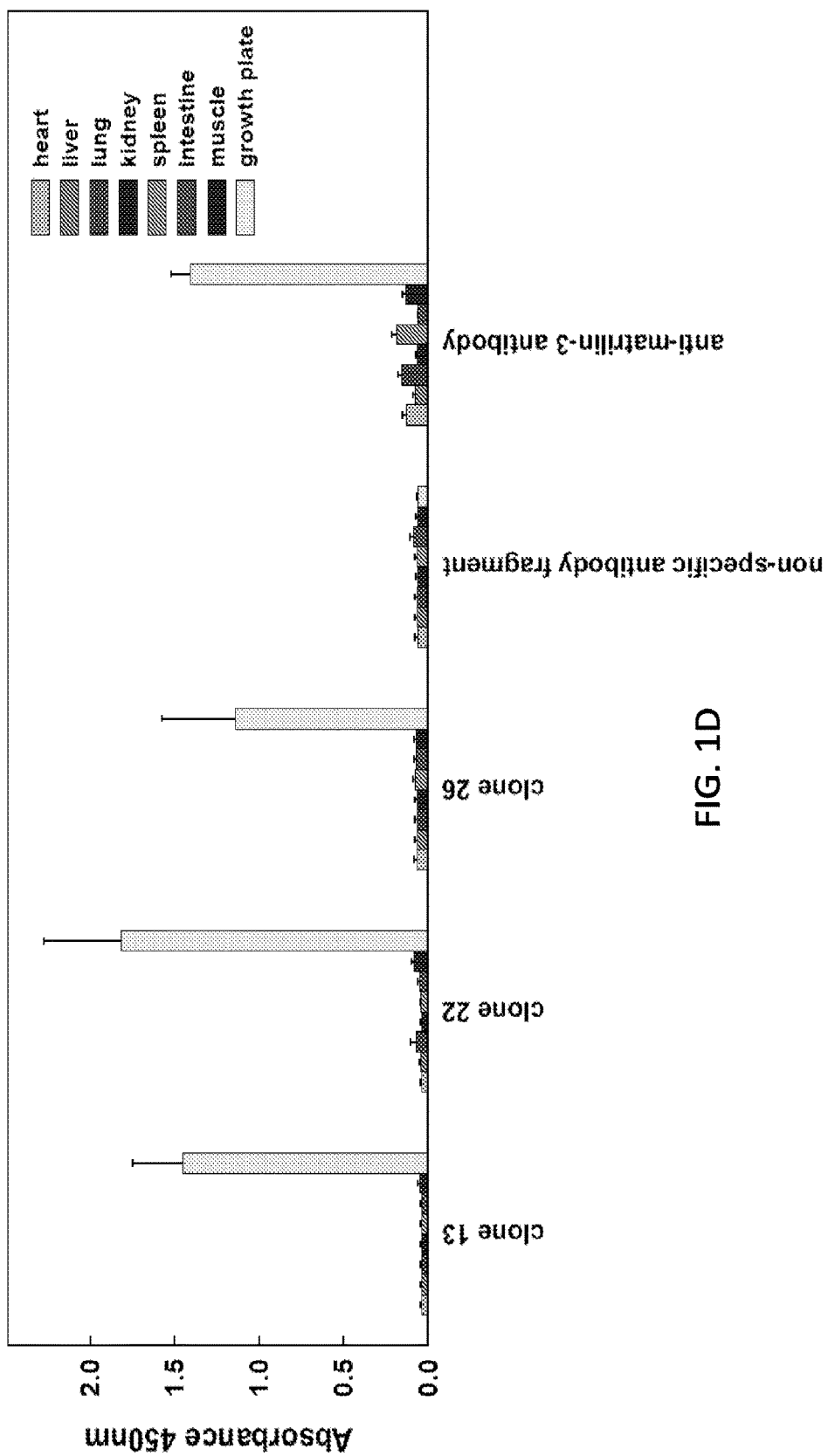

The selected antibody fragments were tested for tissue-specific binding to cartilage, where matrilin-3 is predominantly expressed (Wagener, et al. *FEBS Lett* 413, 129-134, 1997; Burnam, et al. *J Abnorm Psychol* 84, 76-79, 1975; Klatt, et al. *J Biol Chem* 275, 3999-4006, 2000). To examine the tissue specificity of the antibody fragments, homogenized tissue was used from growth plate cartilage, brain, heart, liver, lung, kidney, spleen, small intestine, and muscle from 4-day old mice to coat plastic wells and the binding of the antibody fragments was assessed by ELISA. Fifteen antibody fragments that exhibited increased binding to matrilin-3 of both species were examined for their specificity toward cartilage tissue. While some antibody fragments demonstrated poor tissue binding specificity, antibody fragments 13, 22, and 26 were found to preferentially bind to growth plate cartilage over other tissues (FIG. 1D), and thus were chosen for further studies. A non-specific antibody fragment showed binding to cartilage or other tissues.

Immunohistochemical Localization of Matrilin-3-Binding Antibody Fragments

Figure 2:
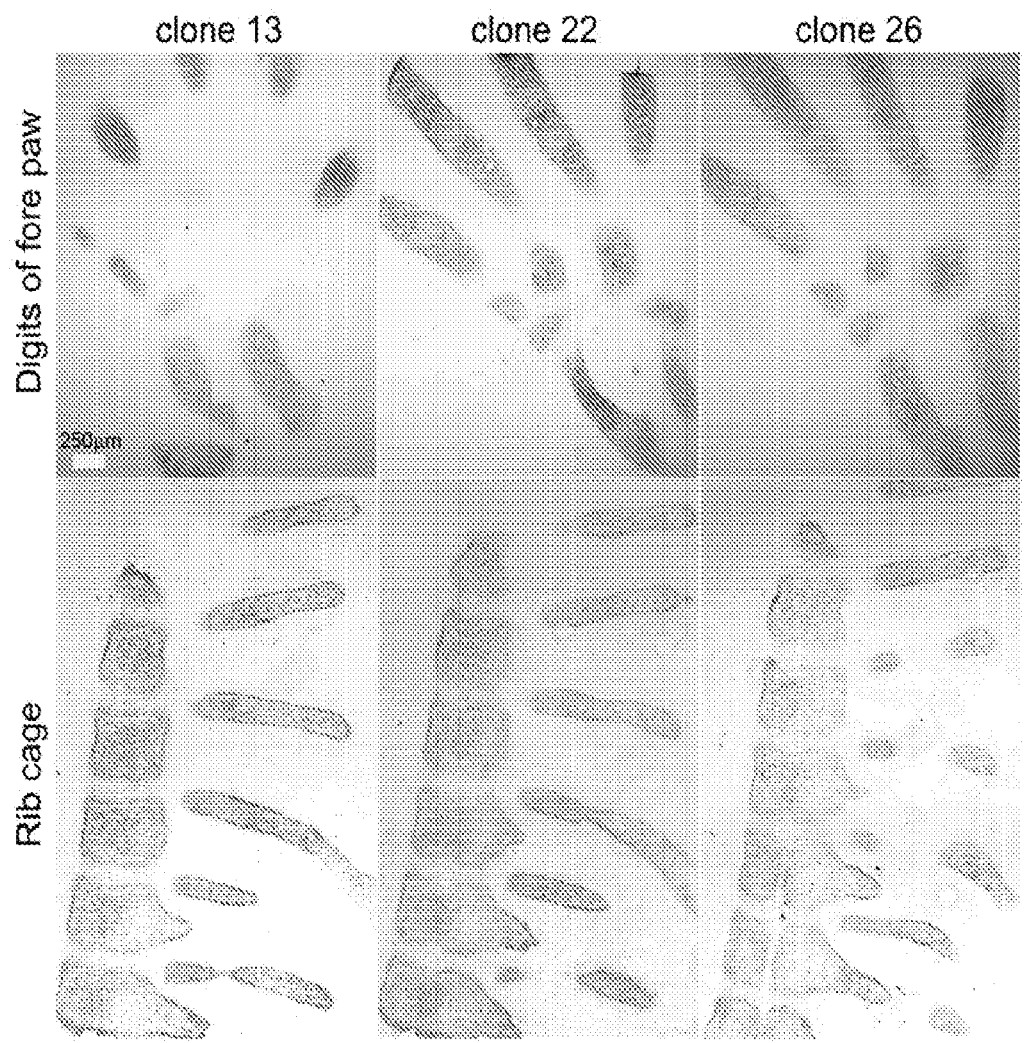
FIG. 2 is a set of digital images showing binding of antibody fragments to tissues in frozen mouse embryo sections. Antibody fragments 13, 22, and 26 were incubated with frozen E15 mouse embryo sections, then detected with HRP-conjugated anti-Fc antibody and stained with DAB substrate to produce a brown color. Immunostaining was observed in cartilage tissues, including digits of forepaw (top row) and rib cages (bottom row), but not in non-cartilaginous structures.

To further characterize the ability and specificity of the antibody fragments to bind to cartilage tissue, the antibody fragments were used to perform immunohistochemical staining on frozen sections of C57BL/6 mouse embryos at embryonic day (E) 15. The three antibody fragments (13, 22 and 26) stained various cartilage structures, such as the cartilaginous anlagen of the bones of the forelimb, but there was no significant staining in non-cartilaginous tissues (FIGS. 2A-C). In contrast, a non-specific antibody fragment failed to show any staining in the cartilage tissues.

Figure 3A:
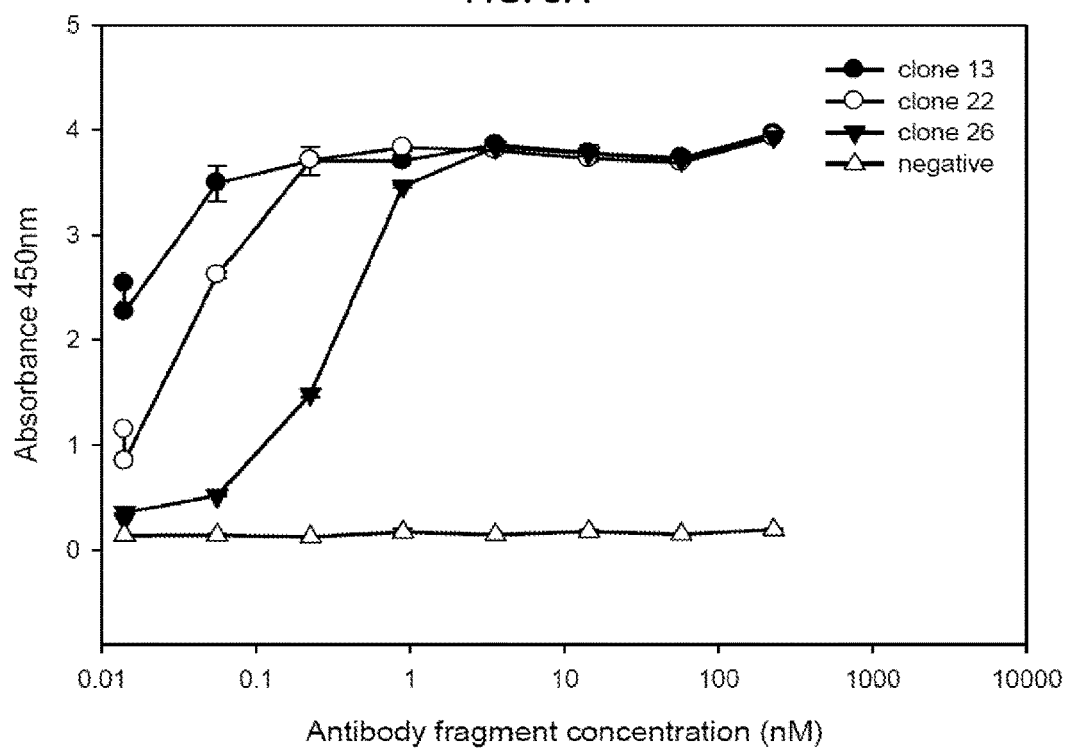
FIGS. 3A and 3B are a set of graphs showing assessment of the binding affinity of purified matrilin-3-binding antibody fragments. The three selected antibody fragments, 13, 22 and 26, were expressed and purified using protein A columns. Various concentrations of each antibody fragment were incubated with recombinant human (A) and mouse (B) matrilin-3 proteins, and binding was measured by ELISA. The negative control (background) lacked an antibody fragment.
Figure 3B:
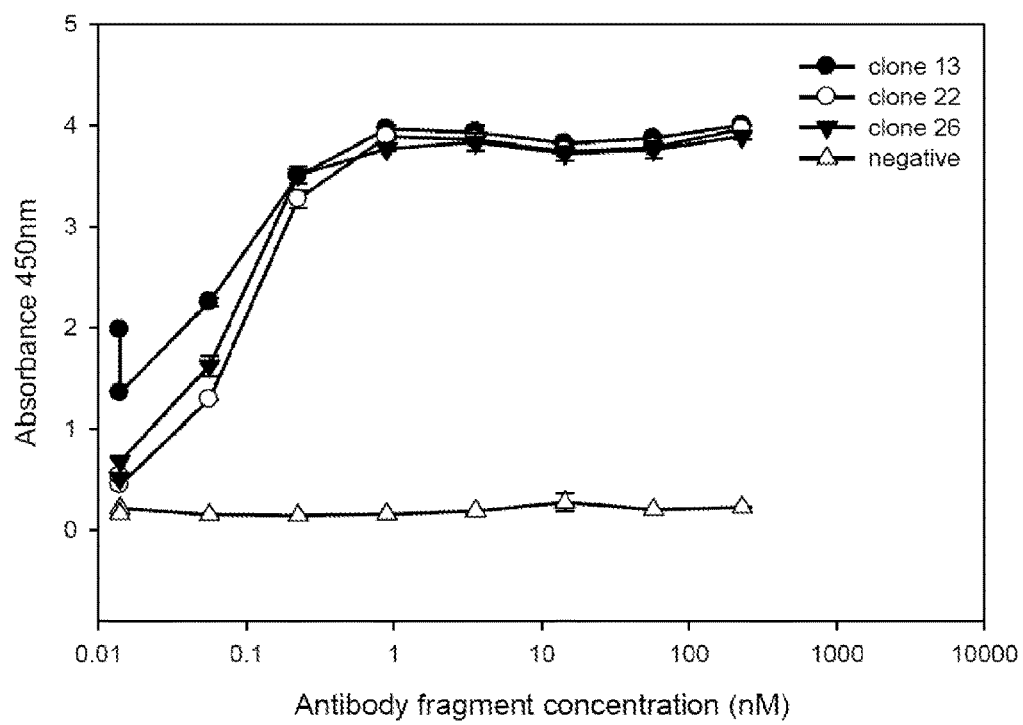

Assessment of the Binding Affinity of Purified Matrilin-3-Binding Antibody Fragments To measure binding affinity quantitatively, different concentrations of antibody fragments 13, 22 and 26 were used to test binding to matrilin-3 proteins, both human and mouse. All three antibody fragments possessed high affinity towards both recombinant human and mouse matrilin-3 proteins with $EC_{50}$ values less than 1 nM (FIGS. 3A and 3B).

Homing of Matrilin-3-Binding Antibody Fragments to Cartilage In Vivo

Figure 4:
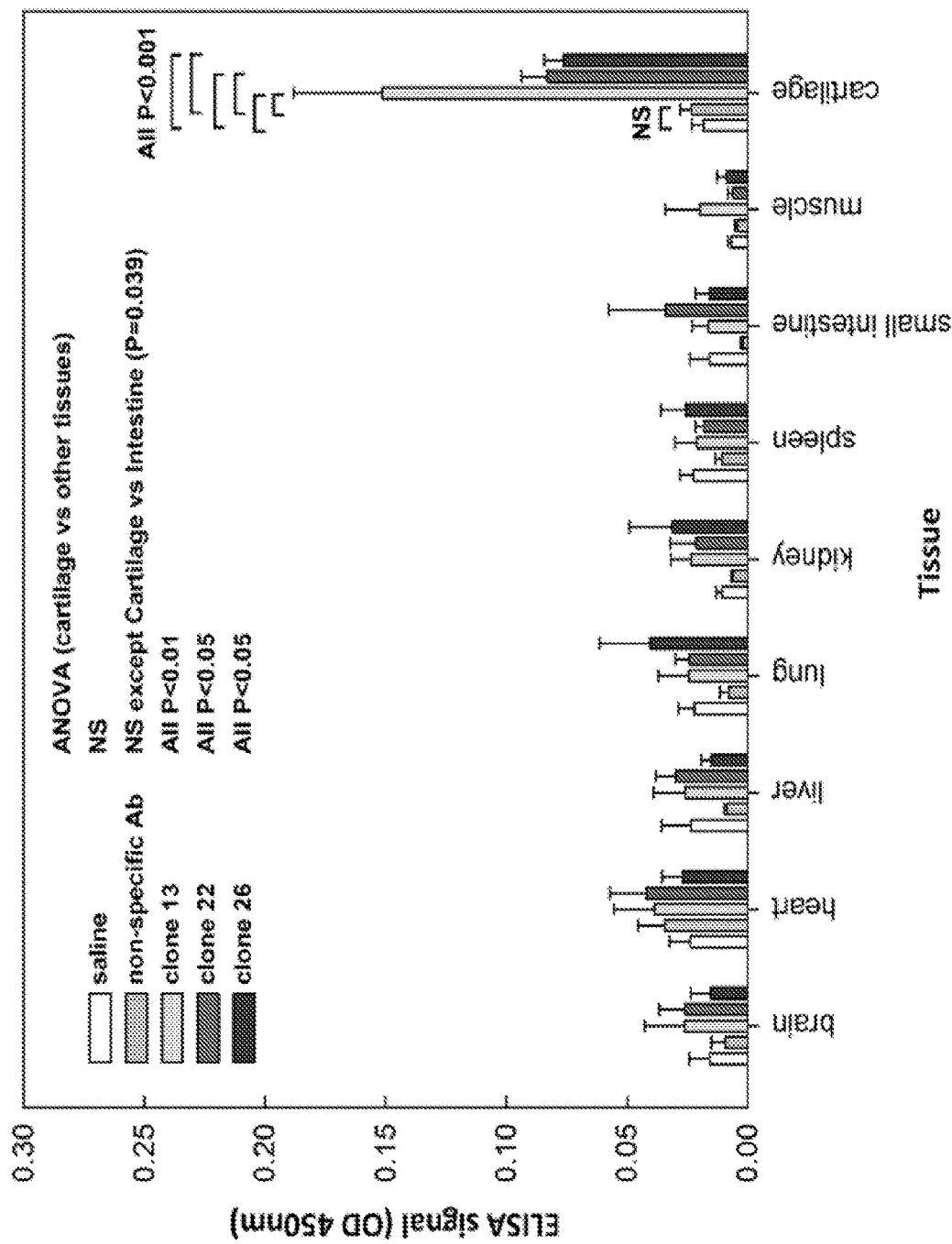
FIG. 4 is a graph showing homing of selected matrilin-3-binding antibody fragments 13, 22 and 26 to cartilage in vivo. Saline, non-specific antibody fragment, or purified antibody fragments were injected intravenously in 3-week old mice. After 24 hours, various organs were collected and homogenized, and tissue lysates were used to coat plastic wells. The presence of antibody fragments was detected by ELISA with an anti-Fc antibody. All three antibody fragments were detected in cartilage, but not in non-cartilaginous organs. Saline and non-specific antibody served as negative controls. Data represent mean±SEM from five independent experiments.

Purified antibody fragments were injected into mice via a tail vein. After 24 hours, distal femoral and proximal tibial growth plate cartilage and various non-cartilaginous organs were isolated, homogenized and used to coat plastic wells. ELISA was performed using anti-human Fc antibody to detect the presence of antibody fragments delivered in vivo. For both the saline-injected and the non-specific antibody fragment-injected controls, the signals in the growth plate and other non-cartilaginous organs were similar. In contrast, for the three antibody fragments tested (13, 22 and 26), the signals for saline or for non-specific antibody fragments (FIG. 4). Furthermore, for these three antibody fragments, the signals were significantly greater in cartilage than in non-cartilaginous organs (FIG. 4), suggesting that the selected antibody fragments homed to cartilage in vivo with high specificity.

Discussion

Antibody fragments that bind to cartilage with high affinity and specificity were identified, and can be used to target therapeutic molecules to growth plate cartilage. A naïve human scFv yeast display library was used for selection of binders to matrilin-3, an extracellular matrix protein primarily expressed in growth plate cartilage. A sequential antigen panning approach (Zhang, et al. *J Immunol Methods* 283, 17-25, 2003) was used, with the first two rounds of panning against human matrilin-3 and the last round against mouse matrilin-3 protein. The resulting pool of clones was significantly enriched for binders to both human and mouse matrilin-3, compared to the naïve library. Individual clones that expressed antibody fragments that bound to both human and mouse matrilin-3 were identified. Of these, three antibody fragments showed specific binding in vitro to homogenates of cartilage tissue, but not homogenates of brain, heart, liver, lung, kidney, spleen, small intestine or muscle. These three fragments also showed tissue-specific binding to cartilage structures in sections of mouse embryos. Binding affinities of the selected antibody fragments (12, 22, and 26) were then measured, demonstrating that all three purified antibody fragments exhibited high affinity for both human and mouse matrilin-3 proteins. After these purified antibody fragments were injected intravenously in mice it was found that they were localized in cartilage and were not detectable in other tissues, including brain, heart, liver, lung, kidney, spleen, small intestine or muscle, indicating that the antibody fragments were capable of specifically targeting cartilage tissue in vivo.

The development of cartilage-targeting proteins opens up new potential approaches to treat growth plate disorders, including skeletal dysplasias, severe short stature due to systemic disease, and severe idiopathic short stature, by targeting growth-regulating endocrine factors specifically to the growth plate. Current growth plate therapy generally involves the manipulation of systemic hormone levels, such as GH, IGF-1, estrogens, and androgens. However, these approaches have limited therapeutic efficacy for the more severe growth plate disorders, including many skeletal dysplasias, and exhibit undesirable effects due to actions on sites other than the growth plate. For instance, in achondroplasia, the most common type of skeletal dysplasia, growth hormone increases bone length, and therefore height, only modestly, and dose is limited by adverse effects on other tissues (Horton, et al. *Lancet* 370, 162-172, 2007). Coupling growth-regulating endocrine factors to cartilage-binding antibody fragments has the potential to direct endocrine therapeutic agents to cartilage. The results presented herein suggest that when administered systemically, the targeting antibody fragment-endocrine factor conjugates would be preferentially taken up by the growth plate cartilage, thereby creating a local depot which might allow sustained high local concentrations of molecules to improve efficacy at the growth plate and decrease adverse effects on other tissues.

In addition to endocrine factors, paracrine factors that stimulate growth plate chondrogenesis, including IHH (Chau, et al. *J Mol Endocrinol* 47, 99-107, 2011; Kobayashi, et al. *J Clin Invest* 115, 1734-1742, 2005; Kronenberg. *Ann N Y Acad Sci* 1068, 1-13, 2006; Maeda, et al. *Proc Natl Acad Sci USA* 104, 6382-6387, 2007; Long, et al. *Dev Biol* 298, 327-333, 2006; Amizuka, et al. *J Cell Biol* 126, 1611-1623, 1994; Long, et al. *Development* 128, 5099-5108, 2001; Mak, et al. *Development* 135, 1947-1956, 2008), BMPs (De Luca, et al. *Endocrinology* 142, 430-436, 2001; Nilsson, et al. *J Endocrinol* 193, 75-84, 2007; Kobayashi, et al. *Proc Natl Acad Sci USA* 102, 18023-18027, 2005; Yoon, et al. *Development* 133, 4667-4678, 2006; Wu, et al. *J Biol Chem* 286, 24726-24734, 2011; Yoon, et al. *Proc Natl Acad Sci USA* 102, 5062-5067, 2005), and CNP (Mericq, et al. *Pediatr Res* 47, 189-193, 2000; Agoston, et al. *BMC Dev Biol* 7, 18, 2007; Olney, et al. *J Clin Endocrinol Metab* 92, 4294-4298, 2007; Olney, et al. *J Clin Endocrinol Metab* 91, 1229-1232, 2006; Teixeira, et al. *Dev Biol* 319, 171-178, (2008); Woods, et al. *Endocrinology* 148, 5030-5041, 2007), can be coupled to growth plate targeting antibody fragments. Because these paracrine factors are normally expressed and exert their action in the growth plate, targeted therapy would serve to localize these factors to their physiological site of action. For example, CNP is an important positive regulator of growth plate chondrogenesis (Mericq, et al. *Pediatr Res* 47, 189-193, 2000; Agoston, et al. *BMC Dev Biol* 7, 18, 2007; Olney, et al. *J Clin Endocrinol Metab* 92, 4294-4298, 2007; Olney, et al. *J Clin Endocrinol Metab* 91, 1229-1232, 2006; Teixeira, et al. *Dev Biol* 319, 171-178, (2008); Woods, et al. *Endocrinology* 148, 5030-5041, 2007). In mice, overexpression of CNP in growth plate compensates for mutations that cause achondroplasia (Yasoda, et al. *Nat Med* 10, 80-86, 2004). However, systemic administration of CNP in humans leads to natriuresis (Igaki, et al. *Hypertens Res* 21, 7-13, 1998). CNP linked to a cartilage-targeting polypeptide is believed to increase the skeletal growth-promoting effect and reduce the effect on renal sodium handling, and thereby presents an effective therapeutic strategy to treat human achondroplasia. Similarly, targeting IHH or BMPs to growth plate cartilage might provide novel treatments for skeletal dysplasias or other causes of growth plate failure, such as systemic inflammatory diseases, renal failure, glucocorticoid therapy or radiation damage.

Apart from treating growth plate disorders, cartilage-targeting polypeptides could also be applied to improve treatment of articular cartilage disorders. For instance, osteoarthritis, a disorder caused by gradual mechanical degradation of articular cartilage with inadequate repair, affects 30-50% of older adults (Loeser. *Clin Geriatr Med* 26, 371-386, 2010). Currently, there is no specific pharmacologic therapy that can prevent the progression of joint damage due to osteoarthritis. Cartilage-targeting antibody fragments, which direct chondrogenic growth factors to articular cartilage, can facilitate regeneration of degrading joint surfaces.

Methods of fusing a chondrogenic agent to the disclosed antibody fragments can be similar to previously described fusion techniques involving the biologically active polypeptide, a linker, and an antibody fragment. For example, multiple cytokine-antibody fusion proteins designed to target malignant tissues and therefore enhance efficacy and diminish systemic side effects are under investigation, including some in clinical trials (Pasche, et al. *Drug Discov Today* 17, 583-590, 2012). A similar strategy has been employed to link alkaline phosphatase to peptides that bind to bone matrix, thereby successfully targeting bone tissue and treating hypophosphatasia in mice and humans (Millan, et al. *J Bone Miner Res* 23, 777-787, 2008; and Yadav, et al. *Bone* 49, 250-256, 2011). Similar techniques can be used to fuse proteins containing the cartilage matrix-binding antibody fragments and biologically active polypeptides, such as GH, IGF-1 and CNP. Additionally, steroids, such as estradiol, can be coupled to the disclosed antibodies to treat growth disorders and/or increase height using known techniques (Yokogawa, et al. *Endocrinology* 142, 1228-1233, 2001).

There have been prior attempts to develop cartilage-binding peptides or polypeptides with the specific goal of targeting drugs to articular cartilage, for example to treat articular cartilage disorders. A linear peptide of six amino acids was reported to bind to collagen IIαI and direct nanoparticles to articular cartilage (Rothenfluh, et al. *Nat Mater* 7, 248-254, 2008), when given locally by intraarticular injection. A scFv antibody fragment was identified that recognized reactive oxygen species-modified type II collagen, which is specifically present in inflamed joints (Hughes, et al. *Arthritis Rheum* 62, 1007-1016, 2010). This scFv was then coupled to soluble tumor necrosis factor receptor II and administered systemically to reduce inflammation of articular cartilage in a murine arthritis model. Because the first study involves local joint administration and the second study targets inflamed cartilage, neither would be expected to target growth plate cartilage. A prior study used a 12-amino acid peptide to target growth plate cartilage (Cheung, J. C. Lui, and Baron, *J Orthop Res.*, 31:1053-1058, 2013), but no high affinity and specificity for cartilage comparable to that achieved in the current study using antibody fragments was identified.

In conclusion, antibody fragments were identified that bind to cartilage matrix with high affinity and specificity and, when administered systemically in vivo, home specifically to cartilage structure. Coupling these cartilage-binding polypeptides to endocrine and paracrine signaling molecules that promote chondrogenesis can allow therapy targeted specifically to growth plate and articular cartilage, and thus open up broad new pharmacological approaches to treat skeletal dysplasias, other severe forms of linear growth failure, and joint diseases. Similarly, targeting such molecules (such as growth hormone) to the antibody fragments can increase the efficacy of the agent and reduce unwanted side effects at tissues where the biological activity of the agent is not desired. For example, growth hormone can be delivered to the desired site of action at the growth plate while minimizing unwanted activity elsewhere in the body that could lead to tumorgenesis.

Example 2

Matril-3 Specific Antibodies Conjugated to a Chondrogenic Agent

This example illustrates construction of matrilin-3 specific antibodies that are conjugated to a chondrogenic agent, IGF-1.

Two approaches were taken to engineer the mAb-IGF-1 conjugates, generating dimeric conjugate and monomeric IGF-1/matrilin-3 scFv/Fc domain conjugates. First, a wild-type Fc domain was used to construct a dimeric fusion protein including two scFv-based matrilin-3 binding domains, two Fc domains and two IGF-1 domains (see FIG. 5A). The wildtype Fc domain forms a dimer and is linked to a single IGF-1 molecule and a single matrilin-3 specific scFv. Second, a mutant (non-dimerizing) Fc domain was used to construct an antibody-conjugate including a single Fc domain linked to a single scFv-based matrilin-3 binding domain and a single IGF-1 molecule (see FIG. 5B). Plasmid DNA expression vectors were constructed encoding the IGF-1-antibody-Fc conjugates (see FIGS. 5A and 5B).

The order of the domains in each conjugate is as follows:
Dimeric Conjugates:
IGF-1-linker-matrilin-3 specific scFv (based on clone 13, 22, or 26)-linker-dimeric Fc domain
Monomeric Conjugates:
IGF-1-linker-monomeric Fc domain-linker-matrilin-3 specific scFv (based on clone 13, 22, or 26)

Figure 5B:
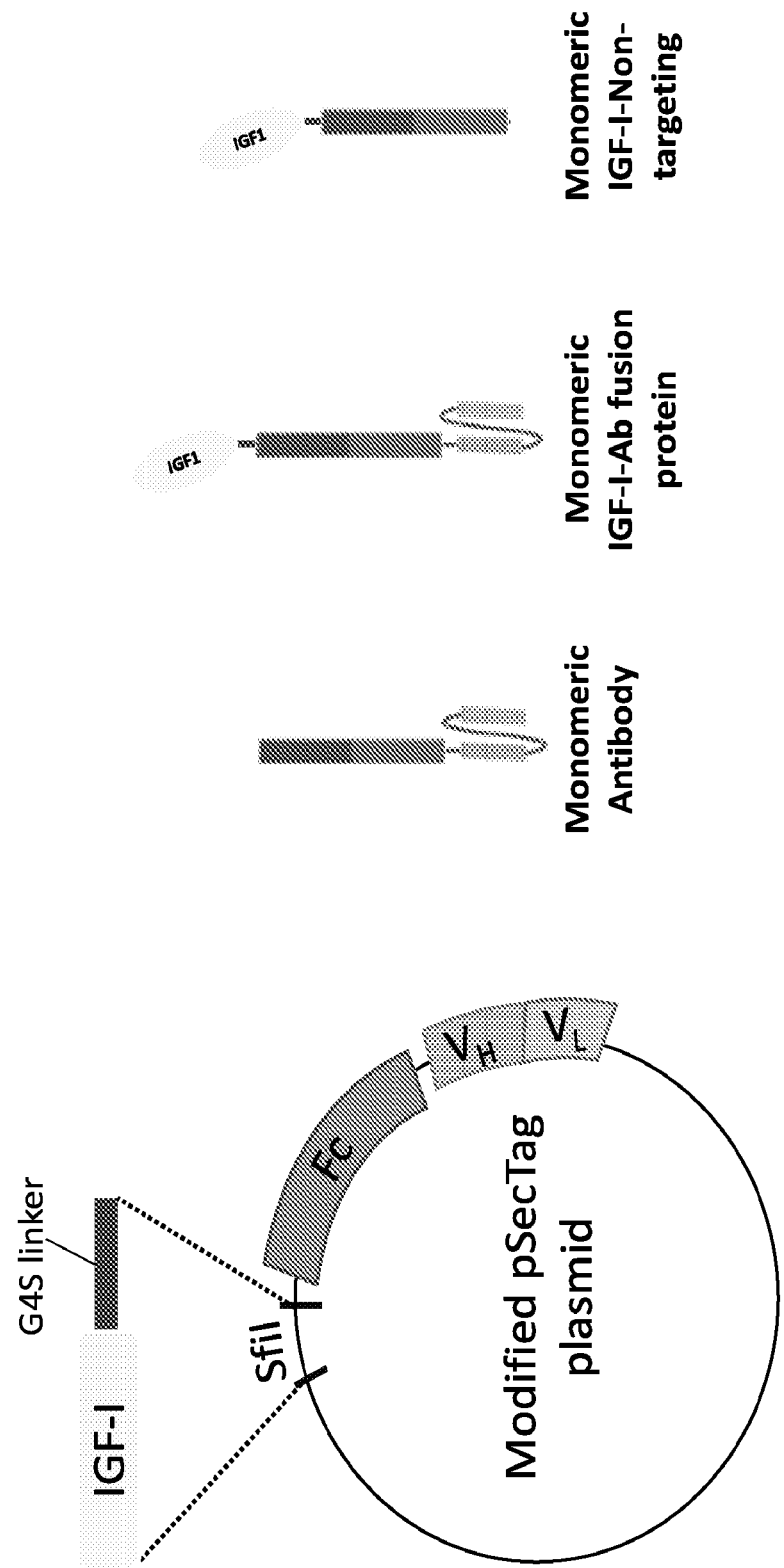

Exemplary amino acid sequences of fusion proteins including IGF-1 linked to a clone 13-, 22-, or 26-based scFv linked to a native Fc domain (dimeric IGF-1-scFv-Fc conjugates) as shown in FIG. 5A are provided as SEQ ID NOs: 41-43, which include scFvs based on the clone 13, clone 22 or clone 26 antibodies, respectively. Exemplary amino acid sequences of fusion proteins including IGF-1 linked to a mutant Fc domain linked to a clone 13-, 22-, or 26-based scFv (monomeric IGF-1-Fc-scFv conjugates) as shown in FIG. 5B are provided as SEQ ID NOs: 44-46, which include scFvs based on the clone 13, clone 22 or clone 26 antibodies, respectively.

Figure 6:
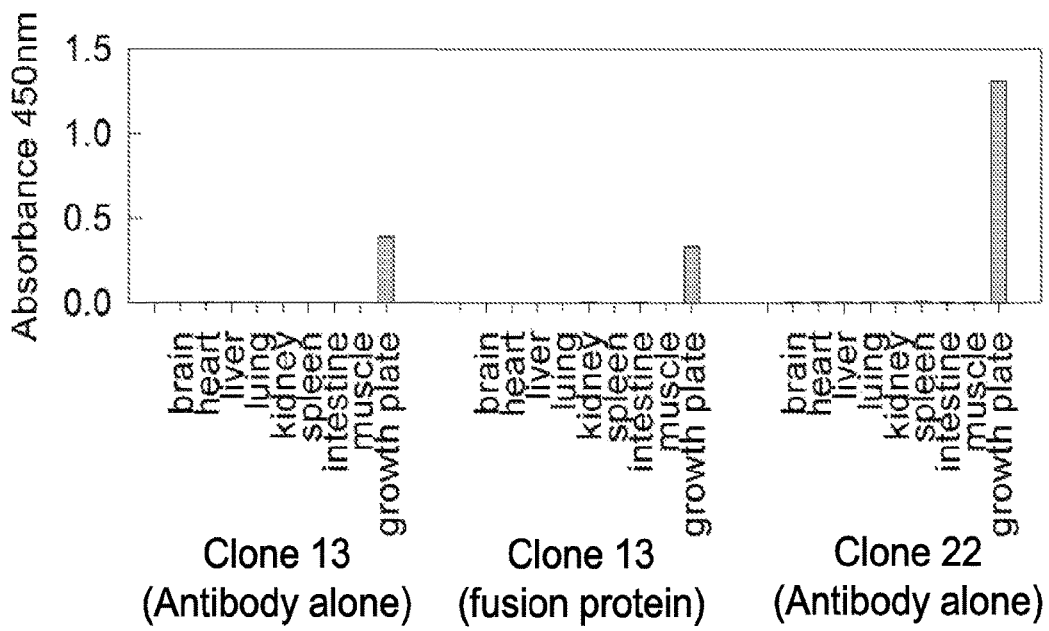
FIG. 6 shows a series of graphs illustrating in vitro binding to cartilage by clone 13, 22, or 26 scFvs or corresponding fusion proteins including an IGF-1 domain linked to a clone 13, 22, or 26 scFv and a Fc domain. ELISA plates were coated with the indicated panel of organ lysates and assayed for binding to clone 13, 22, or 26 scFvs or clone 13, 22, or 26 scFv-IGF-1-Fc fusion proteins.
Figure 6:
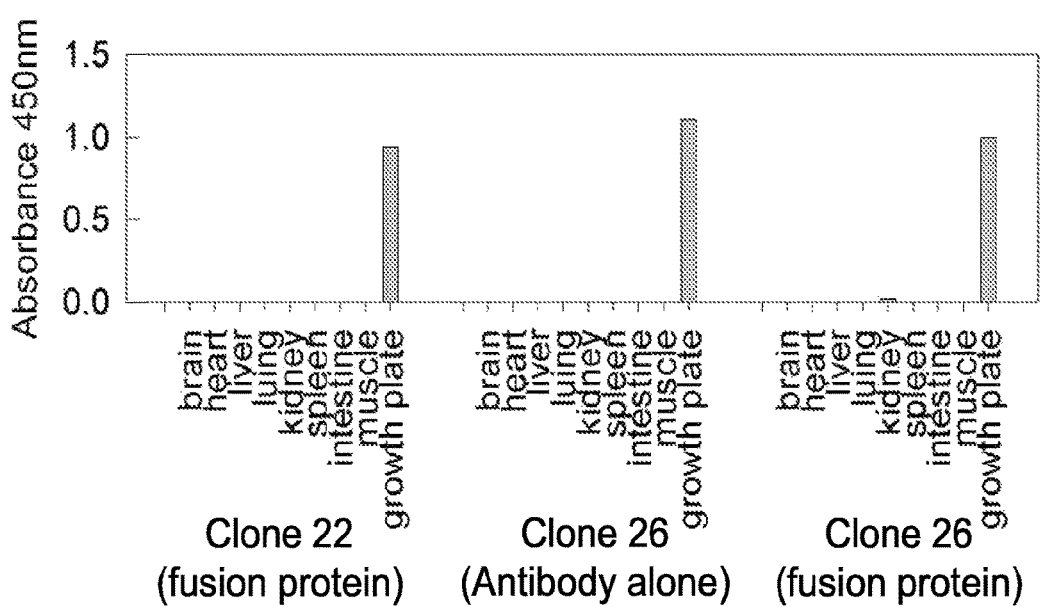

The IGF-1-scFv conjugates were produced by expression in 293 FreeStyle F cells, purified, and tested for binding to lysates from several different tissue types by ELISA. The conjugates were produces using similar methods s those described for production of antibody alone, above. The ELISA plates were coated with the panel of organ lysates listed in FIG. 6 and incubated with clone 13, 22, or 26 scFv, or the corresponding IGF-1-scFv-Fc fusion proteins. The results shown were from assays using dimeric conjugates. As shown in FIG. 6, the IGF-1-scFv-Fc conjugates demonstrated binding affinity and specificity towards growth plate cartilage comparable of that of the unconjugated clone 13, 22, and 26 scFvs, suggesting that addition of IGF-1 and Fc domains did not significantly alter the ability of the scFv domains to recognize matrilin-3.

Figure 7:
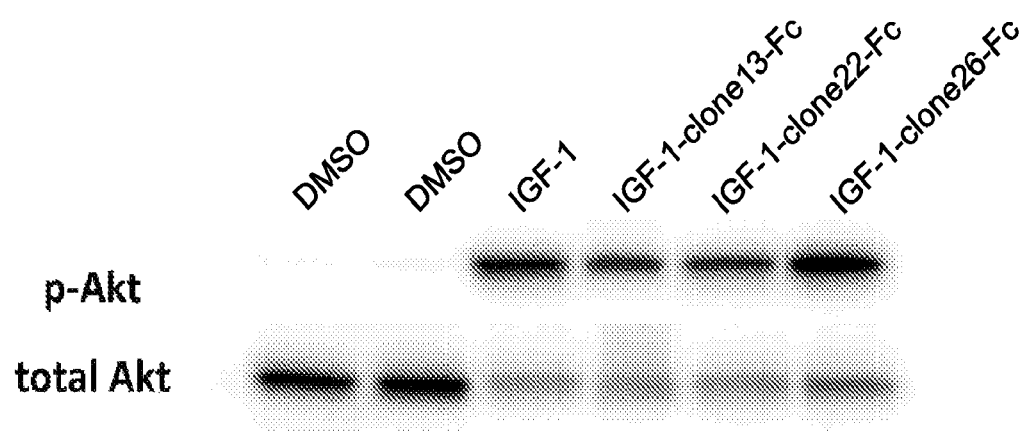
FIG. 7 shows a Western blot illustrating that the biological activity of IGF-1 is not altered by conjugation to a matrilin-3 specific scFv and an Fc domain. The IGF-1-induced Erk and Akt phosphorylation in MCF-7 cells was assayed in the context of IGF-1 alone and the IGF-1-matrilin-3 scFv-Fc conjugates using an established assay. MCF-7 cells were incubated with the IGF-1 alone (10 μM) or IGF-1 conjugated to matrilin-3 specific scFV and Fc domains for 30 minutes, lysed, and total Akt and phospho-AKT were measured by Western blot with Akt-specific and phosph-Akt specific antibodies. DMSO was used as solvent control, GAPDH was used as loading control.

IGF-1 treatment of MCF-7 cells is known to induce Erk and Akt phosphorylation in the MCF-7 breast cancer cell line (Zhang et al. J Mol. Endocrinol., 35:433-447, 2005; Walsh and Damjanovski, Cell Commun. Signal., 9:10, 2011). Therefore, to verify that fusion with a matrilin-3 specific scFv does not interfere with the biological activity of IGF-1, the IGF-1-induced Erk and Akt phosphorylation in MCF-7 cells was assayed in the context of IGF-1 alone and the IGF-1-matrilin-3 scFv-Fc conjugates using an established assay (Zhang et al. J Mol. Endocrinol., 35:433-447, 2005; Walsh and Damjanovski, Cell Commun. Signal., 9:10, 2011). Briefly, MCF-7 cells were incubated with the IGF-1 alone (10 µM) or IGF-1 conjugated to matrilin-3 specific scFV and Fc domains for 30 minutes, lysed, and total Akt and phospho-AKT were measured by Western blot with Akt-specific and phosph-Akt specific antibodies. As shown in FIG. 7, there was no substantial difference in phosphorylation of Akt between the treatment with IGF-1 alone condition compared to treatment with the IGF-1-matrilin specific scFv-Fc fusion proteins. DMSO was used as solvent control, GAPDH was used as loading control.

Example 3

Clinical Evaluation of Therapeutic Agents

The following example provides guidance on the parameters to be used for the clinical evaluation of a conjugate including a monoclonal antibody or matrilin-3 binding fragment thereof that specifically binds to matrilin-3 linked to a chondrogenic agent (such as a CNP polypeptide) in the therapeutic methods of the present disclosure. As discussed herein, the conjugate will be used in the treatment of a cartilage disorder, such as short stature or a skeletal dysplasia. Clinical trials will be conducted which will provide an assessment of doses of the conjugate for safety, pharmacokinetics, and initial response of both surrogate and defined clinical endpoints. The trial will be conducted for a minimum, but not necessarily limited to, twenty-four weeks to collect sufficient safety information on about 10 evaluable patients. The initial dose for the trials will vary from about 0.001 to about 1.0 mg/kg/week, or any of the doses described herein. In the event that the initial dose in this range does not produce a significant direct clinical benefit, the dose should be increased within this range or beyond this range as necessary, and maintained for an additional minimal period of, but not necessarily limited to, 24 weeks to establish safety and to evaluate efficacy further.

Measurements of safety will include adverse events, allergic reactions, complete clinical chemistry panel (including kidney and liver functions), urinalysis, and complete blood count with differential. In addition, other parameters relevant to clinical benefit are monitored. The present example also includes the determination of pharmacokinetic parameters of the conjugate, including absorption, distribution, metabolism, excretion, and half-life and bioavailability in the blood. Such analyses will help refine dose to clinical response.

Methods

Patients undergo a baseline medical history and physical exam, and a standard set of clinical laboratory tests (including CBC, Panel 20, CHSO, and UA). The patients are followed closely with weekly visits to the clinic. The patients return to the clinic for a complete evaluation one week after completing the treatment period. Should dose escalation be required, the patients follow the same schedule outlined above. Safety is monitored throughout the trial.

Diagnosis and Inclusion Criteria

The patients may be male or female, with a documented diagnosis of a condition to be treated, such as a cartilage disorder. A specific example of a cartilage disorder is achondroplasia, which may be confirmed by genetic testing and other evidence of an FGFR-3 mutation or dysfunction. The ideal age range of achondroplasia patients is from infant (<1 year of age) to pre-adolescent (<13 years of age). A patient is excluded from this study if the patient is pregnant or lactating; has received an investigational drug within 30 days prior to study enrollment; or has a medical condition, serious intercurrent illness, or other extenuating circumstance that may significantly decrease study compliance.

Safety

Therapy with the conjugate will be determined to be safe if no significant acute or chronic drug reactions occur during the course of the study. The longer-term administration of the drug will be determined to be safe if no significant abnormalities are observed in the clinical examinations, clinical labs, or other appropriate studies.

It is understood that every embodiment of the disclosure described herein may optionally be combined with any one or more of the other embodiments described herein. It will be apparent that the precise details of the methods or compositions described may be varied or modified without departing from the spirit of the described embodiments. We claim all such modifications and variations that fall within the scope and spirit of the claims below.

We claim:

1. An isolated monoclonal antibody, comprising a heavy chain variable region comprising a heavy chain complementarity determining region (HCDR)1, a HCDR2, and a HCDR3, and a light chain variable region comprising a light chain complementarity determining region (LCDR)1, a LCDR2, and a L-CDR3, of the amino acid sequences set forth as:
SEQ ID NO: 5 and SEQ ID NO: 6, respectively (clone 26); and
wherein the monoclonal antibody specifically binds to matrilin-3.

2. The isolated monoclonal antibody of claim 1, wherein:
the heavy chain variable region comprises an amino acid sequence at least 80% identical to SEQ ID NO: 5 and comprises the CDR sequences of SEQ ID NO: 5;
the light chain variable region comprises an amino acid sequence at least 80% identical to SEQ ID NO: 6 and comprises the CDR sequences of SEQ ID NO: 6; or
the heavy chain variable region and the light chain variable region comprise amino acid sequences at least 80% identical to SEQ ID NO: 5 and SEQ ID NO: 6, respectively, and comprise the CDR sequences of SEQ ID NO: 5 and SEQ ID NO: 6, respectively.

3. The antibody of claim 1, wherein the heavy chain variable region comprises the amino acid sequence set forth as SEQ ID NO: 5.

4. The antibody of claim 1, wherein the light chain variable region comprises the amino acid sequence set forth as SEQ ID NO: 6.

5. The antibody of claim 1, wherein the heavy and light chain variable regions comprise the amino acid sequences set forth as:
SEQ ID NO: 5 and SEQ ID NO: 6, respectively.

6. The antibody of claim 1, comprising a human framework region.

7. The antibody of claim 1, wherein the antibody is an IgG.

8. The antibody of claim 1, conjugated to a heterologous detectable marker.

9. The antibody of claim 8, wherein the detectable marker is a fluorescent, enzymatic, heavy metal, or radioactive marker.

10. The antibody of claim 1, conjugated to a heterologous effector molecule.

11. The antibody of claim 10, wherein the effector molecule is a chondrogenic agent.

12. The antibody of claim 11, wherein the chondrogenic agent is one of a growth hormone, an insulin-like growth factor-1, an Indian hedgehog, a bone morphogenetic protein, a C-type natriuretic protein, or a Wnt protein, or a biologically active fragment thereof that induces chondrogenesis; or
a steroid.

13. The antibody of claim 12, wherein the chondrogenic agent is insulin-like growth factor-1.

14. A method of increasing chondrogenesis in cartilage tissue, comprising:
contacting cartilage tissue with a therapeutically effective amount of the antibody conjugated to the chondrogenic agent of claim 11 under conditions sufficient to form an immune complex, thereby increasing chondrogenesis in the cartilage tissue.

15. A method of targeting a chondrogenic agent to cartilage tissue in a subject, comprising:
administering to the subject an amount of the antibody conjugated to the chondrogenic agent of claim 11 under conditions sufficient to form an immune complex, wherein formation of the immune complex targets the chondrogenic agent to the cartilage tissue in the subject.

16. The method of claim 15, wherein the subject has a cartilage disorder.

17. The method of claim 16, wherein the cartilage disorder is a skeletal dysplasia.

18. The method of claim 17, wherein the skeletal dysplasia is achondroplasia, hypochondroplasia, or short stature homeobox gene (SHOX) deficiency.

19. The method of claim 16, wherein the cartilage disorder is osteoarthritis.

20. The method of claim 16, wherein the method comprises an increase in linear growth of the subject compared to a control treatment.

21. The method of claim 16, wherein the method comprises an increase in chondrogenesis in the subject compared to a control treatment.

22. The method of claim 15, wherein the subject has short stature.

23. The method of claim 22, wherein the short stature is idiopathic short stature, short stature due to systemic disease, short stature associated with a dysmorphic syndrome, short stature due to chromosomal abnormalities, iatrogenic short stature, short stature due to radiation or medications, short stature in children born small for gestational age, and short stature due to undernutrition.

24. The antibody of claim 10, wherein the effector molecule is an anti-arthritis agent.

25. The antibody of claim 24, wherein the anti-arthritis agent is a parathyroid hormone (PTH) or biologically active fragment thereof.

26. A method of targeting an effector molecule to cartilage tissue in a subject, comprising:
administering to the subject an amount of the antibody conjugated to the effector molecule of claim 10 under conditions sufficient to form an immune complex, wherein formation of the immune complex targets the effector molecule to the cartilage tissue in the subject.

27. The method of claim 26, wherein the subject has arthritis.

28. The method of claim 27, wherein the subject has osteoarthritis.

29. The method of claim 26, wherein the subject has a cartilage disorder.

30. The method of claim 29, wherein the cartilage disorder is a skeletal dysplasia.

31. The method of claim 30, wherein the skeletal dysplasia is achondroplasia, hypochondroplasia, or short stature homeobox gene (SHOX) deficiency.

32. The method of claim 29, wherein the subject has short stature.

33. A composition, comprising a pharmaceutically acceptable carrier and an the antibody of claim 1.

34. A kit for treating a cartilage disorder in a subject, comprising a container comprising the antibody of claim 1, and instructions for using the kit.

35. An isolated monoclonal antibody, comprising:
a heavy chain variable region comprising a heavy chain complementarity determining region (HCDR1), a HCDR2, and a HCDR3 comprising the amino acid sequences set forth as residues 26-33, 51-58, 97-108 of SEQ ID NO: 5, respectively, and a light chain variable region comprising a light chain complementarity determining region (LCDR1), a LCDR2, and a LCDR3 comprising the amino acid sequence set forth as residues 26-33, 51-53, and 90-100 of SEQ ID NO: 6, respectively;
wherein the monoclonal antibody specifically binds to matrilin-3.

36. The monoclonal antibody of claim 35, wherein:
the heavy chain variable region comprises an amino acid sequence at least 80% identical to SEQ ID NO: 5 and comprises the CDR sequences of SEQ ID NO: 5;
the light chain variable region comprises an amino acid sequence at least 80% identical to SEQ ID NO: 6 and comprises the CDR sequences of SEQ ID NO: 6; or
the heavy chain variable region and the light chain variable region comprise amino acid sequences at least 80% identical to SEQ ID NO: 5 and SEQ ID NO: 6, respectively, and comprise the CDR sequences of SEQ ID NO: 5 and SEQ ID NO: 6, respectively.

37. The monoclonal antibody of claim 35, wherein the heavy chain variable region comprises the amino acid sequence set forth as SEQ ID NO: 5.

38. The monoclonal antibody of claim 35, wherein the light chain variable region comprises the amino acid sequence set forth as SEQ ID NO: 6.

39. The monoclonal antibody of claim 35, comprising a human framework region.

40. The monoclonal antibody of claim 35, wherein the antibody is an IgG.

41. The monoclonal antibody of claim 35, conjugated to a heterologous detectable marker.

42. The monoclonal antibody of claim 35, wherein the detectable marker is a fluorescent, enzymatic, heavy metal, or radioactive marker.

43. The monoclonal antibody of claim 35, conjugated to a heterologous effector molecule.

44. The monoclonal antibody of claim 43, wherein the effector molecule is a chondrogenic agent.

45. The monoclonal antibody of claim 44, wherein the chondrogenic agent is one of a growth hormone, an insulin-like growth factor-1, an Indian hedgehog, a bone morphogenetic protein, a C-type natriuretic protein, or a Wnt protein, or a biologically active fragment thereof that induces chondrogenesis; or
a steroid.

46. The monoclonal antibody of claim 45, wherein the chondrogenic agent is insulin-like growth factor-1.

47. The monoclonal antibody of claim 43, wherein the effector molecule is an anti-arthritis agent.

48. The monoclonal antibody of claim 47, wherein the anti-arthritis agent is a parathyroid hormone (PTH) or biologically active fragment thereof.

49. A kit for treating a cartilage disorder in a subject, comprising a container comprising the antibody of claim 35, and instructions for using the kit.

50. An antigen binding molecule, comprising:
a heavy chain variable region comprising a heavy chain complementarity determining region (HCDR)1, a HCDR2, and a HCDR3, and a light chain variable region comprising a light chain complementarity determining region (LCDR)1, a LCDR2, and a LCDR3, of the amino acid sequences set forth as SEQ ID NO: 5 and SEQ ID NO: 6, respectively; and
wherein the antigen binding molecule specifically binds to matrilin-3.

51. The antigen binding molecule of claim 50, wherein the antigen binding molecule is a Fv, a Fab, a F(ab')$_2$, an scFv, or an scFV$_2$.

52. A conjugate, comprising the antigen binding molecule of claim 50 linked to a chondrogenic agent or an anti-arthritis agent.

53. The conjugate of claim 52, further comprising an Fc domain.

54. The conjugate of claim 53, comprising, from N- to C-terminus,
the chondrogenic agent, the antigen binding molecule, and the Fc domain; or
the chondrogenic agent, the Fc domain, and the antigen binding molecule.

55. The conjugate of claim 52, wherein the antigen binding molecule is an scFv.

56. The conjugate of claim 52, wherein:
(a) the chondrogenic agent is IGF-1;
(b) the antigen binding molecule is an scFv;
(c) the conjugate comprises an Fc domain, and the Fc domain is an Fc IgG domain that can form a dimer under physiological conditions;
(d) the conjugate comprises an Fc domain, and the Fc domain is a mutant Fc IgG domain that does not dimerize under physiological conditions; or
(e) a combination of two or more of (a), (b), and (c), or a combination of two or more of (a), (b), and (d).

57. The conjugate of claim 56, wherein
(a) the IGF-1 comprises the amino acid sequence set forth as SEQ ID NO: 49
(b) the scFv comprises the amino acid sequence set forth as SEQ ID NO: 12;
(c) the Fc domain comprises the amino acid sequence set forth as SEQ ID NO: 47;
(d) the Fc domain comprises the amino acid sequence set forth as SEQ ID NO: 48 respectively.

58. The conjugate of claim 57, comprising an amino acid sequence set forth as SEQ ID NO: 43 or SEQ ID NO: 46.

59. The antigen binding molecule of claim 50, wherein:
the heavy chain variable region comprises an amino acid sequence at least 80% identical to SEQ ID NO: 5 and comprises the CDR sequences of SEQ ID NO: 5;
the light chain variable region comprises an amino acid sequence at least 80% identical to SEQ ID NO: 6 and comprises the CDR sequences of SEQ ID NO: 6; or
the heavy chain variable region and the light chain variable region comprise amino acid sequences at least 80% identical to SEQ ID NO: 5 and SEQ ID NO: 6, respectively, and comprise the CDR sequences of SEQ ID NO: 5 and SEQ ID NO: 6, respectively.

60. The antigen binding molecule of claim 50, wherein the heavy chain variable region comprises the amino acid sequence set forth as SEQ ID NO: 5.

61. The antigen binding molecule of claim 50, wherein the light chain variable region comprises the amino acid sequence set forth as SEQ ID NO: 6.

62. The antigen binding molecule of claim 50, wherein the heavy and light chain variable regions comprise the amino acid sequences set forth as SEQ ID NO: 5 and SEQ ID NO: 6, respectively.

63. The antigen binding molecule of claim 50, comprising a human framework region.

64. The antigen binding molecule of claim 50, conjugated to a heterologous detectable marker.

65. The antigen binding molecule of claim 64, wherein the detectable marker is a fluorescent, enzymatic, heavy metal, or radioactive marker.

66. The antigen binding molecule of claim 50, conjugated to a heterologous effector molecule.

67. The antigen binding molecule of claim 66, wherein the effector molecule is a chondrogenic agent.

68. The antigen binding molecule of claim 67, wherein the chondrogenic agent is one of a growth hormone, an insulin-like growth factor-1, an Indian hedgehog, a bone morphogenetic protein, a C-type natriuretic protein, or a Wnt protein, or a biologically active fragment thereof that induces chondrogenesis; or
a steroid.

69. The antigen binding molecule of claim 68, wherein the chondrogenic agent is insulin-like growth factor-1.

70. The antigen binding molecule of claim 66, wherein the effector molecule is an anti-arthritis agent.

71. The antigen binding molecule of claim 70, wherein the anti-arthritis agent is a parathyroid hormone (PTH) or biologically active fragment thereof.

72. An antigen binding molecule of an antibody, comprising:
a heavy chain variable region comprising a heavy chain complementarity determining region (HCDR1), a HCDR2, and a HCDR3 comprising the amino acid sequences set forth as residues 26-33, 51-58, 97-108 of SEQ ID NO: 5, respectively, and the a light chain variable region comprising a light chain complementarity determining region (LCDR1), a LCDR2, and a LCDR3 comprising the amino acid sequence set forth as residues 26-33, 51-53, and 90-100 of SEQ ID NO: 6, respectively; and
wherein the antigen binding molecule specifically binds to matrilin-3.

73. The antigen binding molecule of claim 72, wherein:
the heavy chain variable region comprises an amino acid sequence at least 80% identical to SEQ ID NO: 5 and comprises the CDR sequences of SEQ ID NO: 5;
the light chain variable region comprises an amino acid sequence at least 80% identical to SEQ ID NO: 6 and comprises the CDR sequences of SEQ ID NO: 6; or
the heavy chain variable region and the light chain variable region comprise amino acid sequences at least 80% identical to SEQ ID NO: 5 and SEQ ID NO: 6, respectively, and comprise the CDR sequences of SEQ ID NO: 5 and SEQ ID NO: 6, respectively.

74. The antigen binding molecule of claim 72, wherein the heavy chain variable region comprises the amino acid sequence set forth as SEQ ID NO: 5.

75. The antigen binding molecule of claim 72, wherein the light chain variable region comprises the amino acid sequence set forth as SEQ ID NO: 6.

76. The antigen binding molecule of claim 72, comprising a human framework region.

77. The antigen binding molecule of claim 72, wherein the antigen binding molecule is a Fv, a Fab, a F(ab')$_2$, an scFv, or an scFV$_2$ fragment.

78. The antigen binding molecule of claim 72, conjugated to a heterologous detectable marker.

79. The antigen binding molecule of claim 78, wherein the detectable marker is a fluorescent, enzymatic, heavy metal, or radioactive marker.

80. The antigen binding molecule of claim 72, conjugated to a heterologous effector molecule.

81. The antigen binding molecule of claim 80, wherein the effector molecule is a chondrogenic agent.

82. The antigen binding molecule of claim 81, wherein the chondrogenic agent is one of a growth hormone, an insulin-like growth factor-1, an Indian hedgehog, a bone morphogenetic protein, a C-type natriuretic protein, or a Wnt protein, or a biologically active fragment thereof that induces chondrogenesis; or a steroid.

83. The antigen binding molecule of claim 82, wherein the chondrogenic agent is insulin-like growth factor-1.

84. The antigen binding molecule of claim 80, wherein the effector molecule is an anti-arthritis agent.

85. The antigen binding molecule of claim 84, wherein the anti-arthritis agent is a parathyroid hormone (PTH) or biologically active fragment thereof.

86. A method of targeting an effector molecule to cartilage tissue in a subject, comprising:

administering to the subject an amount of the antigen binding molecule conjugated to the effector molecule of claim 80 under conditions sufficient to form an immune complex, wherein formation of the immune complex targets the effector molecule to the cartilage tissue in the subject.

87. The method of claim 86, wherein the subject has arthritis.

88. The method of claim 87, wherein the subject has osteoarthritis.

89. The method of claim 86, wherein the subject has a cartilage disorder.

90. The method of claim 89, wherein the cartilage disorder is a skeletal dysplasia.

91. The method of claim 90, wherein the skeletal dysplasia is achondroplasia, hypochondroplasia, or short stature homeobox gene (SHOX) deficiency.

92. The method of claim 90, wherein the subject has short stature.

93. A conjugate, comprising the antigen binding molecule of claim 72 linked to a chondrogenic agent or an anti-arthritis agent.

94. The conjugate of claim 93, further comprising an Fc domain.

95. The conjugate of claim 94, comprising, from N- to C-terminus, the chondrogenic agent, the antigen binding molecule, and the Fc domain; or the chondrogenic agent, the Fc domain, and the antigen binding molecule.

96. The conjugate of claim 93, wherein the antigen binding molecule is an scFv.

97. The conjugate of claim 93, wherein:

(a) the chondrogenic agent is IGF-1;

(b) the antigen binding molecule is an scFv;

(c) conjugate comprises an Fc domain, wherein the Fc domain is an Fc IgG domain that can form a dimer under physiological conditions;

(d) the conjugate comprises an Fc domain, wherein the Fc domain is a mutant Fc IgG domain that does not dimerized under physiological conditions; or (e) a combination of two or more of (a), (b), and (c), or a combination of two or more of (a), (b), and (d).

98. A single chain variable molecule (scFv) comprising the amino acid sequence set forth as SEQ ID NO: 12, wherein the scFv specifically binds to matrilin-3.

* * * * *

UNITED STATES PATENT AND TRADEMARK OFFICE
CERTIFICATE OF CORRECTION

PATENT NO. : 10,323,083 B2  
APPLICATION NO. : 15/111773  
DATED : June 18, 2019  
INVENTOR(S) : Jeffery Baron et al.

It is certified that error appears in the above-identified patent and that said Letters Patent is hereby corrected as shown below:

In the Claims

Claim 33, Column 157, Lines 55-56: "A composition, comprising a pharmaceutically acceptable carrier and an the antibody of claim 1" should read -- A composition, comprising a pharmaceutically acceptable carrier and the antibody of claim 1 --.

Signed and Sealed this  
Sixteenth Day of February, 2021

Drew Hirshfeld  
*Performing the Functions and Duties of the*  
*Under Secretary of Commerce for Intellectual Property and*  
*Director of the United States Patent and Trademark Office*